(12) United States Patent
Wang et al.

(10) Patent No.: US 7,253,341 B2
(45) Date of Patent: Aug. 7, 2007

(54) DENATURANT STABLE AND/OR PROTEASE RESISTANT, CHAPERONE-LIKE OLIGOMERIC PROTEINS, POLYNUCLEOTIDES ENCODING SAME, THEIR USES AND METHODS OF INCREASING A SPECIFIC ACTIVITY THEREOF

(75) Inventors: Wangxia Wang, Rehovot (IL); Dan Pelah, Rehovot (IL); Tal Alegrand, Gedera (IL); Yehonathan Pouny, Givat Shmuel (IL); Ira Marton, Rehovot (IL); Amnon Wolf, Herzliah Pituach (IL); Oded Shoseyov, Karme Yosef (IL); Arie Altman, Rehovot (IL)

(73) Assignees: Yissum Research Development Company of the Hebrew University of Jerusalem, Jerusalem (IL); Fulcrum SP Ltd., Herzlia Pituach (IL)

( * ) Notice: Subject to any disclaimer, the term of this patent is extended or adjusted under 35 U.S.C. 154(b) by 126 days.

(21) Appl. No.: 10/233,409

(22) Filed: Sep. 4, 2002

(65) Prior Publication Data

US 2003/0092624 A1 May 15, 2003

Related U.S. Application Data

(63) Continuation-in-part of application No. PCT/IL02/00174, filed on Mar. 5, 2002.

(60) Provisional application No. 60/272,771, filed on Mar. 5, 2001.

(51) Int. Cl.
*C12N 15/79* (2006.01)
*C12N 15/82* (2006.01)
*A01H 5/00* (2006.01)

(52) U.S. Cl. ............... 800/298; 435/320.1; 435/252.3; 435/254.2; 435/419; 435/348

(58) Field of Classification Search ............... 536/23.4, 536/23.6; 435/320.1, 419, 468, 252.3; 800/13, 800/278
See application file for complete search history.

(56) References Cited

U.S. PATENT DOCUMENTS

| | | | |
|---|---|---|---|
| 5,097,025 A * | 3/1992 | Benfey et al. | ......... 536/23.6 |
| 2003/0092624 A1 | 5/2003 | Wang et al. | |
| 2005/0074763 A1 | 4/2005 | Wang et al. | |

FOREIGN PATENT DOCUMENTS

| | | |
|---|---|---|
| EP | 0774512 | 5/1997 |
| WO | WO 02/070647 | 9/2002 |
| WO | WO 2004/022697 | 3/2004 |

OTHER PUBLICATIONS

Basler et al. ,GenBank Accession No. 14054, Apr. 27, 1993, Hampster (Syrian golden) PrP gene, complete cds.*

Prusiner et al. Prion protein biology. Cell May 1, 1998, vol. 93, pp. 337-348.*

Liautard JP. Prions and molecular chaperones. Arch. Virol. Suppl. 1993, vol. 7, pp. 227-243.*

Sun et al. Conformational and functional differences between recombinant human lens alphaA- and alphaB-crystallin. J Biol Chem. Mar. 7, 1997;272(10):6220-5.*

Sun et al. Thermodynamic stability of human lens recombinant alphaA- and alphaB-crystallins. J Biol Chem. Nov. 26, 1999;274(48):34067-71.*

Broun et al. Catalytic plasticity of fatty acid modification enzymes underlying chemical diversity of plant lipids.1998, Science, Vo 282, pp. 1315-1317.*

Liu et al. Two transcription factors, DREB1 and DREB2, with an EREBP/AP2 DNA binding domain separate two cellular signal transduction pathways in drought- and low-temperature-responsive gene expression, respectively . . . Plant Cell. Aug. 1998;10(8):1391-406.*

Florack et al. Expression of giant silkmoth cecropin B genes in tobacco.Transgenic Research, Mar. 1995, vol. 4, No. 2, p. 132-141.*

Fladung M. et al. Excision of the maize transposable element Ac in periclinal chimeric leaves of 35S-Ac-rolC transgenic aspen-Populus. Plant Mol Biol. Apr. 1997;33(6):1097-103.*

Shpigel E. et al. Immobilization of recombinant heparinase I fused to cellulose-binding domain. Biotechnol Bioeng. Oct. 5, 1999;65(1):17-23.*

Bradshaw et al. GenBank Accession No. M18538, Populus x generosa pop3 peptide mRNA, complete cds, Nov. 30, 2000.*

Doerks T. et al. Protein annotation: detective work for function prediction. Trends Genet. Jun. 1998;14(6):248-50.*

Florack D. et al. Expression of giant silkmoth cecropin B genes in tobacco. Transgenic Res. Mar. 1995;4(2):132-41.*

Mittler R. et al. Inhibition of Programmed Cell Death in Tobacco Plants during a Pathogen-Induced Hypersensitive Response at Low Oxygen Pressure. Plant Cell. Nov. 1996;8(11):1991-2001.*

Anderson W.F. Human gene therapy. Nature. Apr. 30, 1998;392(6679 Suppl):25-30. Review.*

Liu et al, "Two Transcription Factors, DREB1 and DREB2, With an EREBP/AP2 DNA Binding Domain Separate Two Cellular Signal Transduction Pathways in Drought- and Low-Temperature-Responsive Gene Expression, Respectively, in *Arabidopsis*", *The Plant Cell*, 10:1391-1406, 1998.

(Continued)

*Primary Examiner*—Cynthia Collins

(57) ABSTRACT

Novel denaturant-stable, protease resistant, homo-oligomeric proteins, also referred to herein as stable proteins (SPs), having chaperone-like activity; methods of production and purification of SPs; nucleic acids encoding SPs; methods of isolating nucleic acids encoding SPs; antibodies recognizing SPs; the use of SPs for stabilizing, refolding, repairing, preventing aggregation and de-aggregating macromolecules such as proteins; fusion proteins including SPs; nucleic acid constructs encoding the fusion proteins; and their uses in a variety of methods and applications.

45 Claims, 18 Drawing Sheets

OTHER PUBLICATIONS

Wang et al, "Plant Tolerance to Water and Salt Stress: The Expression Pattern of a Water Stress Responsive Protein (BspA) in Transgenic Aspen Plants", *Plant Biotechnology and In Vitro Biology in the 21st Century*, p. 561-565, 1999.

Wang et al, "Characterization of Sp1, A Stress-Responsive, Boiling Soluble, Homo-Oligomeric Protein From Aspen", *Plant Physiology*, 130: 865-875, 2002. Esp. p. 866, Fig.1, p. 867, Fig.2, p. 871, Fig.8.

Soto et al. "Heterologous Expression of A Plant Small Heat-Shock Protein Enhances *Escherichia coli* Viability Under Heat and Cold Stress", Plant Physiology, 120: 521-528, 1999.

Lee et al. "Structure and In Vitro Molecular Chaperone Activity of Cytosolic Small Heat Shock Proteins From Pea", Journal of Biological Chemistry, 270(18): 10432-10438, 1995.

Basler et al. "Hamster (Syrian Golden) PrP Gene, Complete Cds: Scrapie and Cellular PrP Isoforms Are Encoded by the Same Chromosomal Gene", GenBank Accession No. 14054, 1993.

Prusiner et al. "Prion Protein Biology", Cell, 93: 337-348, 1998.

Liautard "Prions and Molecular Chaperones", Arch. Vir., 7(Suppl.): 227-243, 1993.

Sun et al. "Conformational and Functional Differences Between Recombinant Human Lens αA- and αB-Crystallin", Journal of Biological Chemistry, 272(10): 6220-6225, 1997.

Sun et al. "Thermodynamic Stability of Human Lens Recombinant αA- and αB-Crystallins", Journal of Biological Chemistry, 274(48): 34067-34071, 1999.

Broun et al. "Catalytic Plasticity of Fatty Acid Modification Enzymes Underlying Chemical Diversity of Plant Lipids", Science, 282: 1315-1317, 1998.

Florack et al. "Expression of Giant Silkmoth Cecropin B Genes in Tobacco", Transgenic Research, 4(2): 132-141, 1995.

Pelah et al. "Characterization of BspA, A Major Boiling-Stable, Water-Stress-Responsive Protein in Aspen (*Populus tremula*)", Tree Physiology, 15(10): 673-678, 1995.

Altman et al. "Molecular Biology of Drought Tolerance and Transformation of Populus and Pinus at the Hebrew University of Jerusalem", Dendrome, 3(2): 5-7, 1996. p. 6, 1-h Col., § First, Full.

* cited by examiner

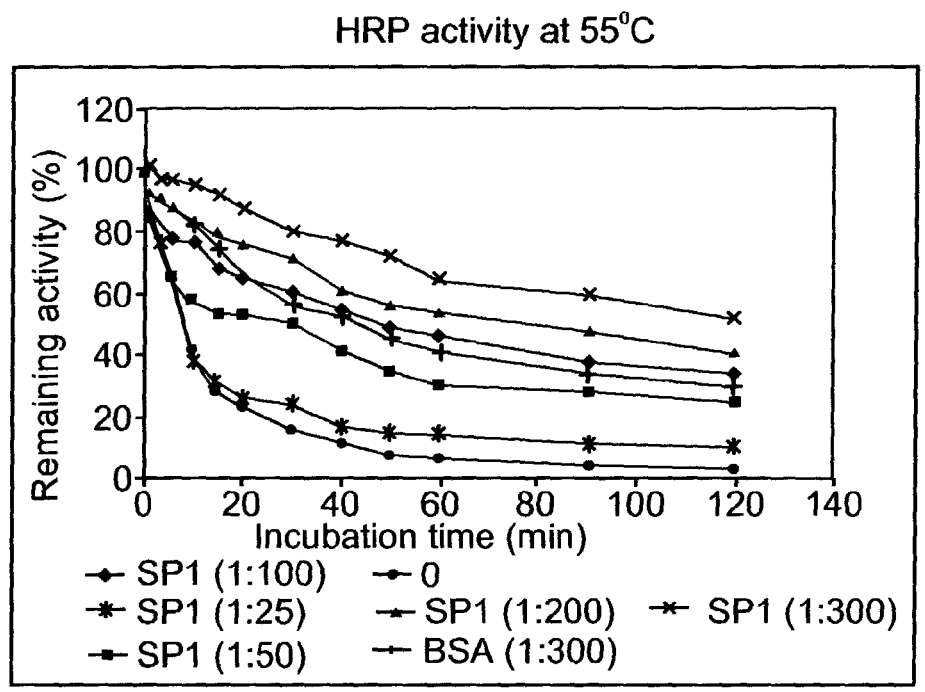

Fig. 4

```
atccacagagagaaagggaagacatggcaaccagaactccaaagcttgtg
                      M  A  T  R  T  P  K  L  V
aagcacacattgttgactcggttcaaggatgagatcacacgagaacagat
 K  H  T  L  L  T  R  F  K  D  E  I  T  R  E  Q  I
cgacaactacattaatgactataccaatctgctcgatctcattccaagca
 D  N  Y  I  N  D  Y  T  N  L  L  D  L  I  P  S  M
tgaagagtttcaattggggcacggatctgggcatggagtctgcggagcta
 K  S  F  N  W  G  T  D  L  G  M  E  S  A  E  L
aaccgaggatacactcatgcctttgaatctacatttgagagcaagtctgg
 N  R  G  Y  T  H  A  F  E  S  T  F  E  S  K  S  G
tttgcaagagtacctcgattctgctgctcttgctgcatttgcagaagggt
 L  Q  E  Y  L  D  S  A  A  L  A  A  F  A  E  G  F
ttttgcctactttgtcacagcgtcttgtgatagactactttctctactaa
 L  P  T  L  S  Q  R  L  V  I  D  Y  F  L  Y  *
acgctcaggagtaacgacttcggccgggctatttcatggtaataaagtaa
tgtaatgttcaataaatgctggttttgaaccactgaatgttcgtgtcttg
atttcttgtctgtgctaagtgaagggagtgctgctattcctttaaaaata
aagcccttgggggttgagttgtagtttttcaatctttttccccgatttatt
tcggtcttggtgttgtt
```

Fig. 5

Plurality: 10.00
Threshold: 4
AveWeight 1.00
AveMatch 2.91
AvMisMatch -2.00

```
                                                                          SEQ ID NO:
         Amino acid:1                                                         50
est.msf{est-whe1}    --------VVK HLVIVQFKED VTPERLDGLI RGYAGLV... DKVPSMKAFH  7
est.msf{est-whe2}    --------VVK HLVIVQFKED VTPERLDGLI RGYAGLV... DKVPSMKAFH  8
est.msf{est-whe3}    --------VVK HLVIVQFKED VTPERLEGLI RGYAGLV... DKVPSMKAFH  9
est.msf{est-ma1}     --------VVK HILLASFKEE VTQERLDELI RGYAALV... GVVPSMKAFH 10
est.msf{est-ri1}     --------VVK HILLARFKED VAPERLDQLI RGYAGLV... DLVPSMKAFH 11
est.msf{est-whe4}    --------VVK HLVLARFKEE ATPEALDXLI RRYAGLV... DAVPSMKAFH 12
     est.msf{est1}   -MEEAKGPVK  HVLLASFKDG VSPEKIEELI KGYANLV... NLIEPMKAFH 13
est.msf{est-at3}     ---------- ---------- ---------- ---------- ----------  14
est.msf{est-so1}     --------VVK HVLLAKFKDD VTPERIEELI KDYANLV... NLIPPMKSFH 15
est.msf{est-to1}     --------VVK HILLAKFKDG IPPEQIDQLI KDYANLV... NLVEPMKAFO 16
est.msf{est-so2}     ---------- HVLLPKLKDY FTPERIE*LM VDYANLV... NLMPRMKSFH 17
     est.msf{Bspp1}  MATRTPKLVK  HTLATRFKDE ITREQIDNYI NDYTNLL... DLIPSMKSFN 18
est msf{est-whe5}    ---------K  HLCLVRFKEG VVVEDIXXXI EELTKLAAEL DTV...KFFG 19
est.msf{est-whe6}    ---------K  HLCLVRFKEG VVVEDIXXXI EELTKLAAEL DTV...KFFG 20
est.msf{est-whe7}    ---------K  HLCMAKFKEG VVVEDIXXXI QELTKLAAEL DTV...KYFG 21
est.msf{est-ri2}     --------VK  HLCLVKFKEE VLXXXVDDIL QCMTKLVSEM DMV...KSFE 22
est.msf{est-sor1}    -RRPTMGEVK  HLCLVKFKEG VV...VEDVL KGMTDLVAGM DMVXXXKSFE 23
est.msf{est-ma2}     ---------- ---------- -------E    STFESTEGIK EYIEHPAHVE 24
est.msf{est-to2}     ---------K  HLVLVKFKED VVVEDILKEL ERLVQEMDIV XXX...KSFV 25
est.msf{est-po1}     ---------- --LLVKFKQD VVEEDVLKQI EQLVNEIDLI XXX...KSFV 26
est.msf{est-so3}     ----------  HYVIVKFKDG VAXXXVDDLI QGLEKMVFCI DHV...KSFE 27
est.msf{est-so5}     ----------  HYVIVKFKDG VAXXXVDELL QGLEKMVSGI DHV...KSFE 28
est.msf{est-so4}     ---------K  HFVIVKFKEG VAXXXVDELT KGMEKLVTEI GAV...KSFE 29
est.msf{est-so7}     ---------- ---------- --------E  ------LVSEI HAV...KSFE 30
     est.msf{est2}   ---MATSGFK  HLVVVKFKED T...KVDEIL KGLENLVSQI DTV...KSFE 31
est.msf{est-so6}     -------KTVE HIVLFKVKEE TEPSKVSDMV NGLGSLVSLD PVLHXLSV.. 32

Consensus            --------VK  HLVLVKFKE- V-PE--D-LI -GYA-LV--- D-V--MKSF- 33

51                                                    100
est.msf{est-whe1}    WGTDVSIENX X.MHQGFTHV FESTFESTEG VKEYVYHPAH VEFATDF.LG
est.msf{est-whe2}    WGTDVSIENX X.MHQGFTHV FESTFESTEG VKEYVYHPAH VEFATDF.LG
est.msf{est-whe3}    WGTDVSIENX X.MHQGFTHV FESTFESTEG VKEYVYHPAH VEFATDF.LG
est.msf{est-ma1}     WGTDVSIENX X.MHQGFTHV FESTFESTEG IKEYIEHPAH VEFAK-----
est.msf{est-ri1}     WGTDVSIENX X.MHQGFTHV FESTFESTEG VKEYIEHPAH VEFANEF.LP
est.msf{est-whe4}    WGTDVTVXXL D.THEGFTHV FESTFESAEG VKEYIAHPSH VEFVDEF.LA
     est.msf{est1}   WGKDVSIEN. ..LHQGYTHI FESTFESKEA VAEYIAHPAH VEFATIF.LG
est.msf{est-at3}     ---------- --LHQGYTHI LESTFESKEA VAEYIAHPAH VEFATIF.LG
est.msf{est-so1}     WGKDVSAENX X.LHQGFTHV FESTFESPEC VAEYVAHPAH VEYANLF.LS
est.msf{est-to1}     WGKDVSIENX X.LHQGFTHV FESTFDSLEG VAEYIAHPVH VEYANTL.LP
est.msf{est-so2}     SGRDVSAEYL H.LXXGCTHV YESTFDSP*G VAEYVAHAAH VEYANQD.LS
     est.msf{Bspp1}  WGTDLGMESA E.LNRGYTHA FESTFESKSG LQEYLDSAAL AAFAEGF.LP
est.msf{est-whe5}    WGKDVLNQE. AXLTQGFTHV FSMSFASAED LAAYMGHEKH SAFAATF.MA
est.msf{est-whe6}    WGKDVLNQE. AXLTQGFTHV FSMSFASAED LAACMGHEKH SAFAATF.MA
est.msf{est-whe7}    WGKDVLNQE. AXLTQGFTHV FVMTFASAED LAACMGHEKH TAFAATF.MA
est.msf{est-ri2}     WGKDVKLNQ. EMLTQGFTHV FSLTFASSED LTTYMSHERH QEFAGTF.MA
est.msf{est-sor1}    WGQDVXLNQ. EMLTQGFTHV FSLTFAFADD LATYMGHDRH AAFAATF.MA
est.msf{est-ma2}     FAKXL..NQ. EMLTQGFTHV FSLTFATAAD LAAYMAHDSH TAFAATF.MA
est.msf{est-to2}     WGKDVXXESH EMLRQGFTHA IIMTFNSKED YQTFANHPNH VGFSATF.AT
est.msf{est-po1}     WGKDTXXESN EMVTQGYTHA MIMTFNSKED YEACVVKEVX XEFSAIF.VT
est.msf{est-so3}     WGKDIXXESH DMLRQGFTHA FLMTFNGKEE FNAFQTHPNH LEFSGVF.SP
est.msf{est-so5}     WGKDIXXESH DMLRQGFTHA FLMAFNGKFE FNAFQTHPNH LEFTGVF.SP
est.msf{est-so4}     WGQDIXXESL DVLRQGFTHA FLMTFNKKED FVAFQSHPNH VEFSTKF.SA
est.msf{est-so7}     WGQDIXXESL DVLRQGFTHA FLMTFNKKRR L--------- ----------
     est.msf{est2}   WGED..KESH DMLRQGFTHA FSMTFENKDG YVAFTSHPLH VEFSAAF.TA
est.msf{est-so6}     ..GPLLRNRS SALTXXFTHM LHSRYKSKED LEAYSAHPSH VSVVKGYVLP Consensus            WGKDV--E-- --LHQGFTHV FESTFESKEG VAEY--HPAH VEFA--F-L-
```

Fig. 12

```
                         101                123
est.msf(est-whe1)   STEKVLIIDF ~~~~~~~~~~ ~~~
est.msf(est-whe2)   STEKVLIIDF ~~~~~~~~~~ ~~~
est.msf(est-whe3)   STEKVLIIDF ~~~~~~~~~~ ~~~
est.msf(est-ma1)    ~~~~~~~~~~ ~~~~~~~~~~ ~~~
est.msf(est-ri1)    VLEKTLIIDY ~~~~~~~~~~ ~~~
est.msf(est-whe4)   LAEKMLIVDY ~~~~~~~~~~ ~~~
est.msf(est-whe4)   LAEKMLIVDY ~~~~~~~~~~ ~~~
est.msf(est1)       SLDKVLVIDY KPTSVSL~~~ ~~~
est.msf(est-at3)    SLDKVLVIDY ~~~~~~~~~~ ~~~
est.msf(est-so1)    CLEKVIVIDY ~~~~~~~~~~ ~~~
est.msf(est-to1)    QLEKFLIVDY ~~~~~~~~~~ ~~~
est.msf(est-so2)    CLEKVIAIDY ---------- ---
est.msf(Bspp1)      TLSQRLVIDY FLY~~~~~~~ ~~~
est.msf(est-whe5)   VLDKVVVLDF ~~~~~~~~~~ ~~~
est.msf(est-whe6)   VLDKVVVLDF ~~~~~~~~~~ ~~~
est.msf(est-whe7)   ALDKVVVMDF ~~~~~~~~~~ ~~~
est.msf(est-ri2)    AIDKVVVVDF ~~~~~~~~~~ ~~~
est.msf(est-sor1)   ALDKVVVIDF ~~~~~~~~~~ ~~~
est.msf(est-ma2)    AIDKVLVVDF ~~~~~~~~~~ ~~~
est.msf(est-to2)    VTDKAVLLDF ~~~~~~~~~~ ~~~
est.msf(est-po1)    VVEKILVLNF ~~~~~~~~~~ ~~~
est.msf(est-so3)    AIEKIVVLDF ~~~~~~~~~~ ~~~
est.msf(est-so5)    AIEKIVVLDF ---------- ---
est.msf(est-so4)    AIENIVLLDF ~~~~~~~~~~ ~~~
est.msf(est-so7)    ~~~~~~~~~~ ~~~~~~~~~~ ~~~
est.msf(est2)       VIDKIVLLDF PVAAVKSSVV ATP
est.msf(est-so6)    IDDDIMSVDW ~~~~~~~~~~ ~~~

Consensus           -LEKVLVIDF ---------- ---
```

Fig. 12(Continued)

```
  1 MATRTPKLVKHTLATRFKDEITREQIDNYINDYTNLLDLIPSMKS..FNW  48 SEQ ID NO:2
    ||||||||||||| ||||||||||||||||||||||||||||||.|||  |||
  1 MATRTPKLVKHTLLTRFKDEITREQIDNYINDYTNLLDLIPTMKSFTFNW  50 SEQ ID NO:35

49 GTDLGMESAELNRGYTHAFESTFESKSGLQEYLDSAALAAFAEGFLPTLS  98
    |||||||||||||||||||||||||||||||||||||||||||||||||
 51 GTDLGMESAELNRGYTHAFESTFESKSGLQEYLDSAALAAFAEGFLPTLS 100

99 QRLVID..YFLY 108
    ||||||  ||||
101 QRLVIDFTYFLY 112
```

Fig. 13

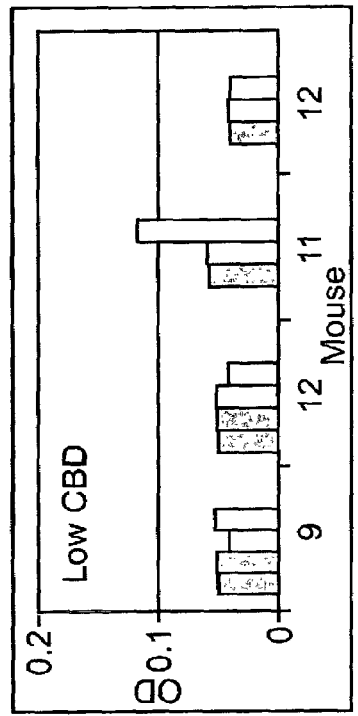
Fig. 20b(i)
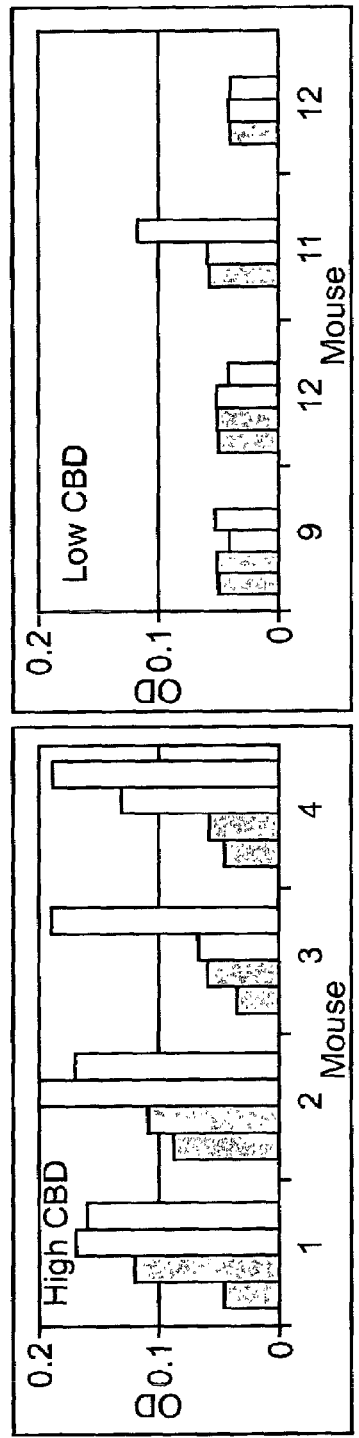
Fig. 20b(iii)
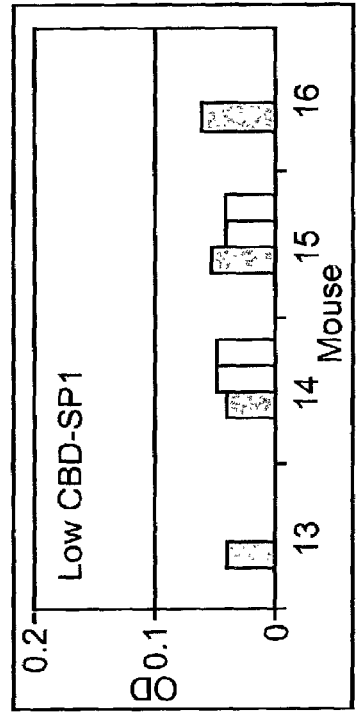
Fig. 20b(ii)
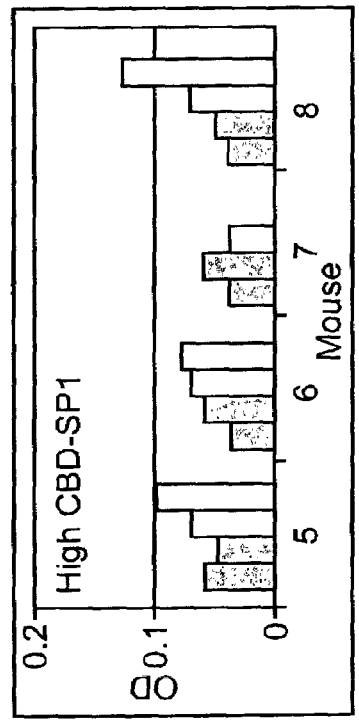
Fig. 20b(iv)

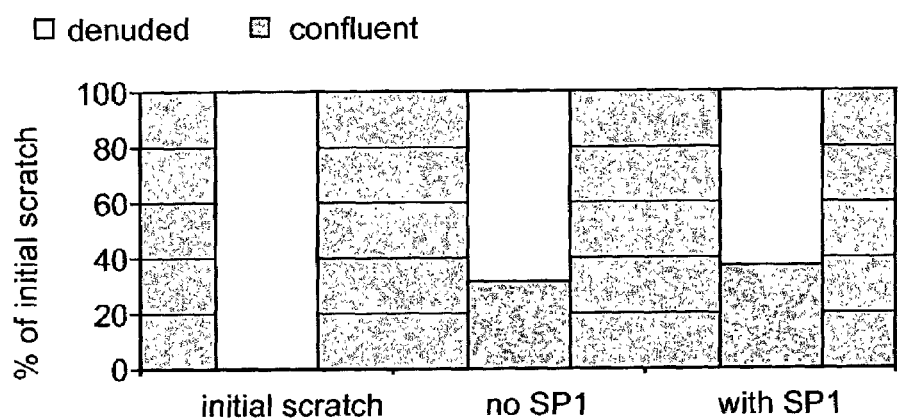
Fig. 22
Fig. 23a
| Protein | HRP protection Units/mg protein |
| --- | --- |
| Recombinant SP1 | 457 |
| CBD-SP1 fusion protein | 274 |
Fig. 23b

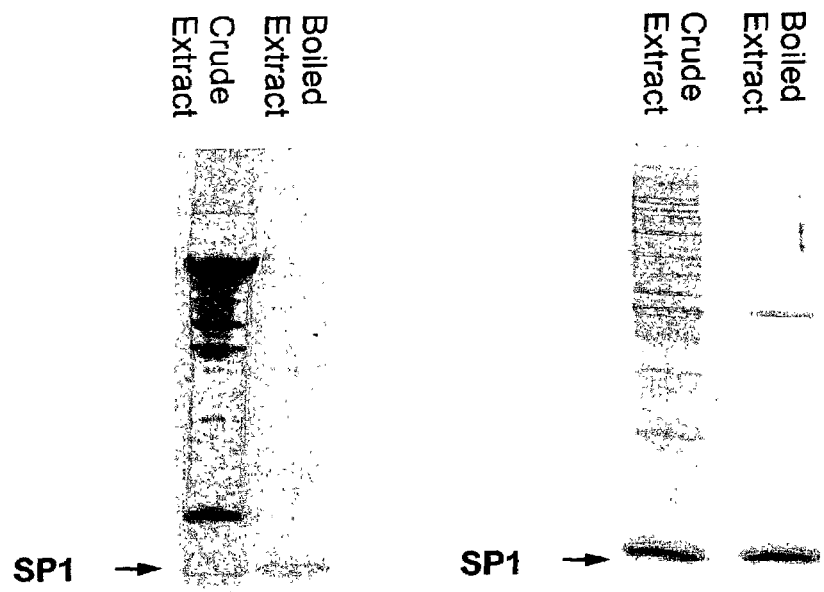
Fig. 24a(i)    Fig. 24a(ii)
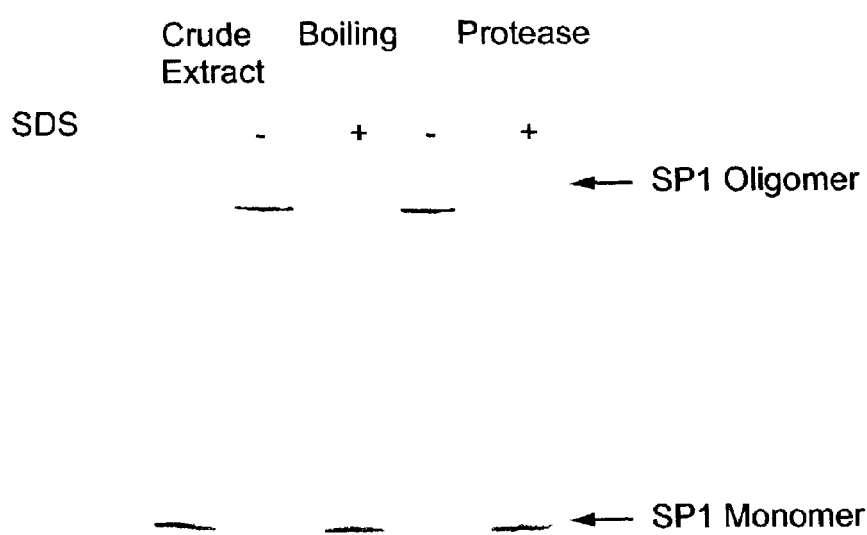
Fig. 24b

DENATURANT STABLE AND/OR PROTEASE RESISTANT, CHAPERONE-LIKE OLIGOMERIC PROTEINS, POLYNUCLEOTIDES ENCODING SAME, THEIR USES AND METHODS OF INCREASING A SPECIFIC ACTIVITY THEREOF

This is a Continuation-In-Part of PCT/IL02/00174, filed Mar. 5, 2002, which claims priority from U.S. Provisional Patent Application No. 60/272,771, filed Mar. 5, 2001.

FIELD AND BACKGROUND OF THE INVENTION

The present invention relates to denaturat (e.g., boiling, detergent, other denaturants) stable and/or protease resistant, chaperone-like oligomeric proteins polynucleotides encoding same, uses thereof and methods of increasing the specific activity thereof. More particularly, the present invention relates to novel denaturat-stable, protease resistant, homo-oligomeric proteins composed of homo-monomers, which proteins are referred to hereinbelow as stable proteins (SPs), methods of production and purification of SPs, nucleic acid constructs encoding SPs, antibodies recognizing SPs, the use of SPs for stabilizing, refolding and de-aggregating, in other words, chaperoning, macromolecules such as proteins, fusion proteins including SPs, nucleic acid constructs encoding these fusion proteins, their use in immunization and/or formation of homogenous or heterogeneous complex structures, methods of increasing the specific activity of the stable proteins and other applications.

Molecular Chaperones:

Molecular chaperones are characterized by their remarkable ability to recognize selectively and bind unstable, non-natively organized (herein after non-native) proteins. The interactions of chaperones with such proteins addresses multiple (diverse) functions that are specific to different chaperones, and include: facilitating and promoting folding of nascent proteins to their final conformation, holding substrates in an unstructured form that is competent for membrane transport, maintaining proteins in specific conformations, preventing aggregation of unfolded proteins, and promoting renaturation of aggregated proteins. The last two functions are particularly important for cells experiencing high temperature and other stresses. It is therefore not surprising that many molecular chaperones were first identified as heat shock proteins (Hsps).

Heat Shock Protein (Hsps):

Hsps are a group of proteins found in all organisms exposed to stress temperatures. It has been clearly shown that many Hsps posses the activities of molecular chaperones that are involved in the proper folding of nascent polypeptides and help damaged proteins regain their biologically active conformation (Hartl, 1996). Small Hsps (sHsps) are Hsps having a molecular size ranging from 12-40 kDa in different organisms, and which are found abundantly in plants. Plant shsp like other sHsp and alpha crystallins tend to form large oligomeric complexes that are believed to be their functional form (Chen et al., 1994; Lee et al., 1995; Collada et al., 1997). Suzuki et al. (1998) provided the evidence that chloroplast-localized Hsp21 from pea exists as a complex and does not dissociate during heat stress and recovery. In contrast to plant sHsps, mammalian cytosolic sHsps undergo complex dissociation to monomers by phosphorylation during heat stress (Rogalla et al., 1999). A recent paper by Haslbeck et al., (1999) demonstrated that the dissociation of Hsp26 complex from yeast is temperature-regulated and is a prerequisite for efficient chaperone activity. It has been shown that in vitro, shsps bind to non-native proteins (Lee et al., 1995, Ehrnsperger et al., 1997, Veinger et al., 1998), therefore preventing the aggregation of non-native proteins, allowing subsequent refolding by chaperone network (Ehrnsperger et al., 1997, Veinger et al., 1998; Haslbeck et al. 1999).

In general, Hsps are stable at moderate temperatures but not at temperatures exceeding 80° C. Accumulation of pea Hsp18.1 remains stable with a half life of 38 hours at 38° C. At 55° C., the effect of Hsp18.1 on preventing aggregation of heat denatured LDH was less than that at 45° C. (Lee et al., 1995). Hsp25 oligomer was stable at 43° C. up to 60 minutes (Ehrnsperger et al., 1997). Exposure of Hsp21 to temperatures above 70° C. led to irreversible aggregation (Hmdahl et al. 1999). The only report of a highly heat stable Hsp is HSP 12 from yeast (Praekelt and Meacock, 1990). Based on its physico-chemical properties and similarity of amino acid composition, Mtwisha et al. (1998) suggested that HSP 12 is a LEA-like protein. It has not been reported that any oligomeric complex of sHsps is stable under SDS denaturation. All the reported sHsps are verified as monomer in SDS-PAGE, unless the protein has been cross-linked.

Uses of Hsp and Chaperone-like Molecules:

The unique ability of stress proteins to stabilize protein and peptide structures has been employed to modify the antigenicity of peptides, to protect cells from oxidative and thermal stress, to alter protein aggregation and to promote in vitro protein folding.

The ability of Hsps to effect the conformation of antigens has led to a number of proposed applications, including the incorporation of Hsp 70, Hsp 90 and gp 76 into vaccinations using non-antigenic tumor antigens (U.S. Pat. No. 6,162,436 to Srivastava), for eliciting immunity to agents of infectious disease (U.S. Pat. No. 6,139,841 to Srivastava) and the suppression of allograft and xenograft rejection through modulation of tissue graft immune response (U.S. Pat. No. 5,891,653 to Attfield).

High level expression of cloned DNA sequences encoding Hsps has been employed to confer novel stress resistance in the transformed cells. Overexpressed human Hsp 27 protected transformed 1929 and 13.S. 1.24 cells from oxidative stress (Rogalla, T., et al. JBC (1999) 274, 18947-56). The plant-derived sHsp Cs Hsp 17.5 (from chestnut cotyledons), when overexpressed in transformed *E. coli*, protected the bacteria against extremes of cold (4° C.) and heat (50° C.) (Soto-A, et al. Plant Physiology (1999) 120, 521-528).

Alpha-beta lens crystallin is also considered a sHsp protein. When a DNA sequence encoding the crystallin protein was expressed in cells prone to amyloid aggregate formation, the shsp prevented in vitro fibril formation. However, this de-aggregation increased rather than decrease the toxicity of the amyloid beta protein. (Stege, G. J. et al., Biochem. and Biophys. Res. Comm. (1999) 262 (1): 152-6).

Scaffolding proteins have been successfully employed in the in-vitro assembly of viral capsid proteins (Newcomb, W W. et al., Journal of Virology (1999) 73, 4231-50); to promote accurate protein folding in-vitro and in heterologous expression systems (see, U.S. Pat. No. 5,561,221 to Yoshida et al.) and to promote immunological response by displaying a plurality of antigens on the same particle (Gonzalo et al. J. Mol. Biol (2001) 305, 259-267.

None of the known Hsp or sHsp, however, is stable under harsh denaturing conditions such as boiling or exposure to high SDS concentration or is resistant to proteolytic cleavage.

Boiling-Stable Proteins from Plants:

Pelah et al. (1995) teaches an attempt of purifying a boiling stable protein from water-stressed aspen shoots. A boiling-stable proteins extract was separated on a 10% SDS-PAGE, yielding a dominant band having a 66 kDa molecular mass. When micro-sequenced, the N-terminal sequence of the 66 kDa protein exhibited high homology with wheat germins GF-2.8 and GF-3.8. Germins and germin-like proteins are ubiquitous, water-soluble, homo-oligomeric extracellular glycoproteins, exhibiting extreme thermal-, pH- and detergent-stability and protease resistance, and having oxalate oxidase activity, however they lack any chaperone-like activity.

SUMMARY OF THE INVENTION

According to one aspect of the present invention there is provided an isolated nucleic acid comprising a first polynucleotide encoding a denaturant (e.g., boiling and/or detergent) stable and/or protease resistant protein (herein, stable protein, SP), the stable protein having a chaperone-like activity; and a second polynucleotide including a promoter sequence being operably linked to the first polynucleotide for directing an expression of the stable protein.

According to a further feature in preferred embodiments of the invention described below, the promoter sequence is a eukaryote promoter.

According to a still further feature in the described preferred embodiments the eukaryote promoter is a constitutive promoter.

According to a yet further feature in the described preferred embodiments the promoter is a plant promoter, such as a constitutive plant promoter, a tissue specific plant promoter and an inducible plant promoter.

According to a yet further feature in the described preferred embodiments (i) the constitutive plant promoter is selected from the group consisting of CaMV35S plant promoter, CaMV19S plant promoter, FMV34S plant promoter, sugarcane bacilliform badnavirus plant promoter, CsVMV plant promoter, *Arabidopsis* ACT2/ACT8 actin plant promoter, *Arabidopsis* ubiquitin UBQ1 plant promoter, barley leaf thionin BTH6 plant promoter, and rice actin plant promoter; (ii) the tissue specific plant promoter is selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from *Arabidopsis*, napA plant promoter from *Brassica napus* and potato patatin gene plant promoter; and (iii) the inducible plant promoter is selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

According to a yet further feature in preferred embodiments the promoter sequence is a prokaryotic promoter.

According to further features in preferred embodiments of the invention described below, the first polynucleotide has a sequence at least 60% identical with SEQ ID NOs:1, 5, 6, 34, 39 or 40, as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the stable protein has a sequence at least 60% homologous to SEQ ID NOs:2 or 35, as determined using the BestFit software of the Wisconsin sequence analysis package, utilizing the Smith and Waterman algorithm, where gap creation penalty equals 8 and gap extension penalty equals 2.

According to still further features in the described preferred embodiments the stable protein is natively an oligomer.

According to still further features in the described preferred embodiments the chaperone-like activity includes heat stabilization of proteins.

According to still further features in the described preferred embodiments the isolated nucleic acid further comprising a third polynucleotide encoding an additional protein, the third polynucleotide being adjacent and in frame, either at the 5' or the 3', to the first polynucleotide, the first and third polynucleotides encoding, in combination, a fusion protein of the stable protein and the additional protein, wherein the additional protein may be positioned C or N terminally to the stable protein and the fusion protein may also include a spacer peptide of, say 1-100 amino acids between the stable protein and the additional protein.

According to another aspect of the present invention there is provided a nucleic acid construct comprising the nucleic acid described herein.

According to yet another aspect of the present invention there is provided a cell or organism transformed with the nucleic acid described herein.

According to still another aspect of the present invention there is provided a method of isolating a gene encoding a stable protein having chaperone-like activity from a biological source, the method comprising screening an expression library with the polynucleotide described herein or a portion thereof of at least 20, preferably at least 30, more preferably at least 50, still preferably at least 100 contiguous bases.

According to an additional aspect of the present invention there is provided a denaturant (e.g., boiling and/or detergent) stable and/or protease resistant polypeptide having a chaperone-like activity effective, for example, in stabilizing proteins.

According to further features in preferred embodiments of the invention described below, the polypeptide is encoded by a polynucleotide as described herein.

According to still further features in the described preferred embodiments the polypeptide has a sequence at least 60% homologous to SEQ ID NOs:2 or 35, as determined using the BestFit software of the Wisconsin sequence analysis package, utilizing the Smith and Waterman algorithm, where gap creation penalty equals 8 and gap extension penalty equals 2.

According to still further features in the described preferred embodiments the polypeptide is natively an oligomer, preferably a homo-oligomer of at least 10 subunits.

According to yet an additional aspect of the present invention there is provided an antibody, either polyclonal or monoclonal antibody, recognizing at least one epitope of the polypeptide described herein.

According to still an additional aspect of the present invention there is provided a method of preventing an aggregating protein from aggregating into an aggregate comprising causing an effective amount of the polypeptide described herein to become in contact with the aggregating protein.

According to a further aspect of the present invention there is provided a method of de-aggregating aggregates of an aggregating protein comprising causing an effective amount of the polypeptide described herein to become in contact with the aggregate.

Hence, the present invention provides a method of treating a disease associated with protein aggregation of an aggregating protein, the method comprising administering to a subject in need thereof a denaturant stable and/or protease resistant protein, the denaturant stable and/or protease resistant protein having a chaperone-like activity, in an amount sufficient for de-aggregating and/or preventing aggregation of the aggregating protein, the aggregating protein is, for example, beta-amyloid or prion.

According to yet a further aspect of the present invention there is provided a method of stabilizing a protein against denaturing conditions comprising causing an effective amount of the polypeptide described herein to become in contact with the protein.

According to still a further aspect of the present invention there is provided a method of enriching or isolating a denaturant (e.g., boiling and/or detergent) stable and/or protease resistant protein having chaperone-like activity from a biological source, the method comprising (a) extracting total proteins from the biological source, so as to obtain a proteins extract; (b) boiling the proteins extract; (c) collecting soluble proteins; and optionally (d) assaying for chaperone-like activity of the soluble proteins and enriching or isolating the stable protein having the chaperone-like activity. Preferably, the method further comprises size fractionating the soluble proteins.

According to another aspect of the present invention there is provided a method of isolating a gene encoding a denaturant (e.g., boiling and/or detergent) stable, and/or protease resistant protein having chaperone-like activity from a biological source, the method comprising screening an expression library with a polynucleotide encoding a polypeptide as herein described.

According to yet another aspect of the present invention there is provided a method of isolating a gene encoding a denaturant (e.g., boiling and/or detergent) stable and/or protease resistant protein having chaperone-like activity from a biological source, the method comprising (a) extracting total proteins from the biological source, so as to obtain a proteins extract; (b) boiling the proteins extract; (c) collecting soluble proteins; (d) assaying for chaperone-like activity of the soluble proteins and isolating a stable protein having chaperone-like activity; (e) raising antibodies recognizing the stable protein having the chaperone-like activity; and (f) screening an expression library with the antibodies.

According to yet another aspect of the present invention there is provided a method of isolating a gene encoding a denaturant (e.g., boiling and/or detergent) stable and/or protease resistant protein having chaperone-like activity from a biological source, the method comprising (a) extracting total proteins from the biological source, so as to obtain a proteins extract; (b) boiling the proteins extract; (c) collecting soluble proteins; (d) assaying for chaperone-like activity of the soluble proteins and enriching or isolating a stable protein having chaperone-like activity; (e) microsequencing the stable protein so as to obtain at least a partial amino acid sequence thereof; (f) designing an oligonucleotide corresponding to the amino acid sequence; and (g) screening a library with the oligonucleotide.

According to a further aspect of the present invention there is provided a method of isolating a nucleic acid potentially encoding a denaturant (e.g., boiling and/or detergent) stable and/or protease resistant protein having chaperone-like activity, the method comprising screening a cDNA or genomic library with a polynucleotide of at least 17 bases at least 60% identical to a contiguous portion of SEQ ID NOs:1, 5, 6, 34, 39 or 40.

According to yet a further aspect of the present invention there is provided a method of identifying a nucleic acid potentially encoding a denaturant (e.g., boiling and/or detergent) stable and/or protease resistant protein having chaperone-like activity, the method comprising searching an electronic library containing a plurality of nucleic acid and/or amino acid sequences for sequences having a predetermined degree of identity or homology to any of SEQ ID NOs:1, 2, 5-35 or 39-40 or portions thereof of, or corresponding to, at least 15 bases.

According to still another aspect of the present invention there is provided a method of isolating a nucleic acid potentially encoding a denaturant (e.g., boiling and/or detergent) stable and/or protease resistant protein having chaperone-like activity, the method comprising (a) providing at least one pair of oligonucleotides each being at least 15 bases in length, the at least one pair of oligonucleotides including at least one oligonucleotide corresponding to SEQ ID NOs:1, 2, 5-35 or 39-40, the at least one pair of oligonucleotides being selected for amplifying a nucleic acid having a degree of identity with, or encoding proteins homologous, to SEQ ID NOs:1, 2, 5-35 or 39-40; (b) contacting the at least one pair of oligonucleotides with a sample of nucleic acid and amplifying the nucleic acid having the degree of identity with, or encoding proteins homologous to, SEQ ID NOs:1, 2, 5-35 or 39-40; and (c) using the nucleic acid having the degree of identity with or encoding proteins homologous to SEQ ID NOs:1, 2, 5-35 or 39-40 for isolating a nucleic acid potentially encoding a denaturant (e.g., boiling and/or detergent) stable and/or protease resistant protein.

According to still another aspect of the present invention there is provided a method of detergent-free isolation of a protease-resistant protein having chaperone-like activity from a biological source, the method comprising (a) extracting total proteins from the biological source, so as to obtain a proteins extract; (b) contacting the protein extract with a protease; (c) isolating a protease-resistant protein; and optionally (d) assaying the protease-resistant protein for chaperone-like activity.

According to another aspect of the present invention there is provided a fusion protein comprising a denaturant (e.g., boiling and/or detergent) stable and/or protease resistant polypeptide having a chaperone-like activity fused to an additional polypeptide, preferably the fusion protein acquires an oligomeric form.

In one embodiment, the denaturant stable and/or protease resistant polypeptide having the chaperone-like activity is fused to the additional polypeptide via a peptide bond. In another embodiment, the denaturant stable and/or protease resistant polypeptide having the chaperone-like activity is fused to the additional polypeptide via a cross-linker.

According to yet an additional aspect of the present invention there is provided a method of immunization comprising subjecting an immune system of a mammal to the fusion protein described herein.

According to another aspect of the present invention there is provided a method of protecting an enzyme preparation from reduction in enzymatic activity, the method comprising adding to the enzyme preparation a denaturant stable and/or protease resistant protein, the denaturant stable and/or protease resistant protein having a chaperone-like activity, in an amount sufficient for protecting the enzyme preparation from reduction in enzymatic activity.

According to yet another aspect of the present invention there is provided a method of repairing at least a portion of lost enzymatic activity of an enzyme preparation, the method comprising adding to the enzyme preparation a denaturant stable and/or protease resistant protein, the denaturant stable and/or protease resistant protein having a chaperone-like activity, in an amount sufficient for repairing at least the portion of the lost enzymatic activity of the enzyme preparation.

According to still another aspect of the present invention there is provided a method of administering to an animal having an immune system a polypeptide, while reducing an immune response against the polypeptide, the method comprising administering the polypeptide to the animal, the polypeptide being fused to a denaturant stable and/or protease resistant protein, the denaturant stable and/or protease resistant protein having a chaperone-like activity, thereby reducing the immune response against the polypeptide, as compared to an immune response that develops by administering to the animal the polypeptide alone.

According to an additional aspect of the present invention there is provided a transgenic plant expressing a denaturant stable and/or protease resistant protein, the denaturant stable and/or protease resistant protein having a chaperone-like activity above a natural amount of the denaturant stable and/or protease resistant protein having the chaperone-like activity in the plant.

According to yet an additional aspect of the present invention there is provided a method of rendering a plant more tolerant to a biotic or abiotic stress, the method comprising engineering the plant to express a denaturant stable and/or protease resistant protein, the denaturant stable and/or protease resistant protein having a chaperone-like activity, above a natural amount of the denaturant stable and/or protease resistant protein having the chaperone-like activity in the plant.

According to still an additional aspect of the present invention there is provided a method of rendering a plant more recoverable from a biotic or abiotic stress, the method comprising engineering the plant to express a denaturant stable and/or protease resistant protein, the denaturant stable and/or protease resistant protein having a chaperone-like activity, above a natural amount of the denaturant stable and/or protease resistant protein having the chaperone-like activity in the plant.

According to a further aspect of the present invention there is provided a method of increasing cell migration, the method comprising exposing the cells to an amount of a denaturant stable and/or protease resistant protein, the denaturant stable and/or protease resistant protein having a chaperone-like activity, sufficient for increasing cell migration.

According to yet a further aspect of the present invention there is provided a method of accelerating wound healing, the method comprising administering onto a wound an amount of a denaturant stable and/or protease resistant protein, the denaturant stable and/or protease resistant protein having a chaperone-like activity, sufficient for accelerating wound healing.

According to still a further aspect of the present invention there is provided a method of inducing wound healing, the method comprising administering onto a wound an amount of a denaturant stable and/or protease resistant protein, the denaturant stable and/or protease resistant protein having a chaperone-like activity, sufficient for inducing wound healing.

According to another aspect of the present invention there is provided a method of strengthening and/or grooming hair, nail or skin, the method comprising administering onto the hair, nail or skin an amount of a denaturant stable and/or protease resistant protein, the denaturant stable and/or protease resistant protein having a chaperone-like activity, sufficient for strengthening and/or grooming the hair, nail or skin.

According to yet another aspect of the present invention there is provided a pharmaceutical composition, comprising, as an active ingredient, a denaturant stable and/or protease resistant protein, the denaturant stable and/or protease resistant protein having a chaperone-like activity, and a pharmaceutically acceptable carrier.

According to further features in preferred embodiments of the invention described below, the pharmaceutical composition is packaged in a package and identified in print for use in a wound healing application.

According to still further features in the described preferred embodiments the pharmaceutical composition is packaged in a package and identified in print for use in a strengthening and/or grooming hair, nail or skin application.

According to still another aspect of the present invention there is provided a method of isolating a boiling stable protein having chaperone-like activity from a biological source, the method comprising: (a) extracting total proteins from the biological source, so as to obtain a proteins extract; (b) boiling the protein extract; (c) recovering soluble protein fraction; and optionally; (d) assaying the protease-resistant protein for chaperone-like activity.

According to further features in preferred embodiments of the invention described below, the method further comprising digesting the protein extract with a protease.

According to another aspect of the present invention there is provided a method of increasing a binding avidity of a binding molecule, the method comprising displaying multiple copies of the binding molecule on a surface of an oligomer of a denaturant stable and/or protease resistant protein, the denaturant stable and/or protease resistant protein having a chaperone-like activity. The binding molecule, can be, for example, a receptor, a ligand, an enzyme, a substrate, an inhibitor, an antibody and an antigen. In cases where the binding molecule is a binding protein, the binding protein can be fused to the oligomer units via either genetic engeneering techniques or chemical cross linking. In cases where the binding molecule is not a protein, the binding molecule can be fused or linked to the oligomer units via chemical cross linking techniques.

The present invention also provides a hetero complex comprising an oligomer including a plurality of a denaturant stable and/or protease resistant protein, the denaturant stable and/or protease resistant protein having a chaperone-like activity, and at least two different molecules which are fused to the oligomer. The at least two different molecules may comprise at least a first enzyme and a second enzyme. The first enzyme and the second enzyme may catalyze sequential reactions in a synthesis or degradation pathway. The first enzyme and the second enzyme may catalyze different reactions in a synthesis or degradation pathway. In another embodiment, the at least two different molecules comprise at least a binding molecule and a reporter molecule.

According to another aspect of the present invention there are provided methods of increasing the specific activity of a pre-isolated denaturant stable and/or protease resistant protein having chaperone-like activity as determined in Units of protecting activity per mg protein, one method comprising autoclaving said pre-isolated denaturant stable and/or protease resistant protein; whereas the other method comprising treating said pre-isolated denaturant stable and/or protease resistant protein with a protease.

According to yet another aspect of the present invention there is provided an isolated denaturant stable and/or protease resistant protein having chaperone-like activity having an HRP protection activity, as determined using an HRP protection assay, of at lest 10, preferably, at least 50, more preferably, at least 100, more preferably, at least 200, more preferably, at least 500, more preferably, at least 1000, more preferably, at least 1500, more preferably, at least 2000, more preferably, at least 2500, more preferably, at least 3000, more preferably, at least 3500, more preferably, at least 4000, more preferably, at least 4500, more preferably, at least 5000, more preferably, at least 5500, more preferably, at least 6000, more preferably, at least 8000, more preferably, at least 10000, more preferably, at least 15000 Units/mg protein, wherein said HRP protection assay comprises mixing the isolated denaturant stable and/or protease resistant protein having chaperone-like activity at different final protein concentrations at a predetermined volume with 100 µl of 5 nM HRP present in 40 mM HEPES buffer at pH 7.5, thus forming a first reaction mixture, and following incubation of said reaction mixture at 25° C. for 16 hours, determining HRP remaining enzymatic activity by mixing 5 µl of said first reaction mixture with 100 µl of TMB (3 3'5 5'-tetramethylbenzidiine), thus forming a second reaction mixture, incubating said second reaction mixture for 10 minutes, stopping a reaction of said second reaction mixture by an addition of 100 µl of 1 M sulfuric acid and recording colorimetric change in said second reaction mixture at 435 nm, whereby said units are defined as a dilution factor of said denaturant stable and/or protease resistant protein having chaperone-like activity at a concentration of 1 mg/ml that confers 50% protection of HRP activity in said HRP protection assay.

The present invention successfully addresses the shortcomings of the presently known configurations by providing a denaturant (e.g., boiling and/or detergent) stable and/or protease resistant protein and describing its uses.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2a shows SDS stability of the SP1 oligomer. Electro-eluted SP1 (116 kDa) was prepared in SDS sample buffer at a range of molar ratios, and boiled (+) or not boiled (−) before separation on 17% polyacrylamide SDS-tricine gels. FIGS. 2b-c show the heat stability of the SP1 oligomer: Electro-eluted SP1 oligomer (116 kDa) was prepared in SDS sample buffer at a final molar ratio of 1:900 SDS: SP1 monomer and heated for 5, 10 or 20 minutes at the indicated temperatures before separation on 17% polyacrylamide SDS-tricine gels. RT: room temperature. M: Molecular size markers.

FIG. 3a: CS was assayed in the absence (0) or presence of SP1, in the following monomeric molar ratios (CS:SP1): 1:5, 1:12.5, :25, 1:50, or in the presence of BSA and lysozyme (1:25 CS monomer: BSA or lysozyme molar ratio). FIG. 3b: CS was assayed in the absence (0) or presence of recombinant CBD-SP1 in the following monomeric molar ratios (CS monomer: CBD-SP1 monomer): 1:5, 1:10 and 1:20, or in the presence of CBD protein at a molar ratio (CS monomer: CBD) of 1:10 or 1:20. FIG. 3c: CS was assayed in the absence (0) or presence of alpha crystallin at a monomeric molar ratio (CS:crystallin) of 1:12.5, or in the presence of glycerol at final concentrations of 10% or 20%.

FIG. 4 demonstrates the protection of Horseradish Peroxidase (HRP) from heat inactivation by addition of SP1. The activity of HRP at 55° C. was assayed (as described in the examples section that follows) at successive intervals in the absence (0) or presence of native SP1 at monomeric molar ratio (HRP:SP1) of 1:25, 1:50, 1:100, 1:200 or 1:300; or in the presence of BSA at a final ratio (HRP:BSA) of 1:300.

FIG. 5 depicts the SP1 cDNA nucleotide sequence (SEQ ID NO:1) and deduced protein sequence (SEQ ID NO:2) of SP1. SP1 cDNA was submitted to EMBL under the Acession Number AJ276517).

FIG. 6a presents a Coomassie blue stained gel of the bacterial proteins.

FIG. 6b demonstrates the immunodetection of SP1 proteins by Western blotting of the bacterial proteins onto nitrocellulose and reaction with polyclonal anti-SP1 antibodies (1:2,500).

Insert: Chromatogram of the Eluted Peaks of SP1 and CBD-SP 1.

Figure 8:
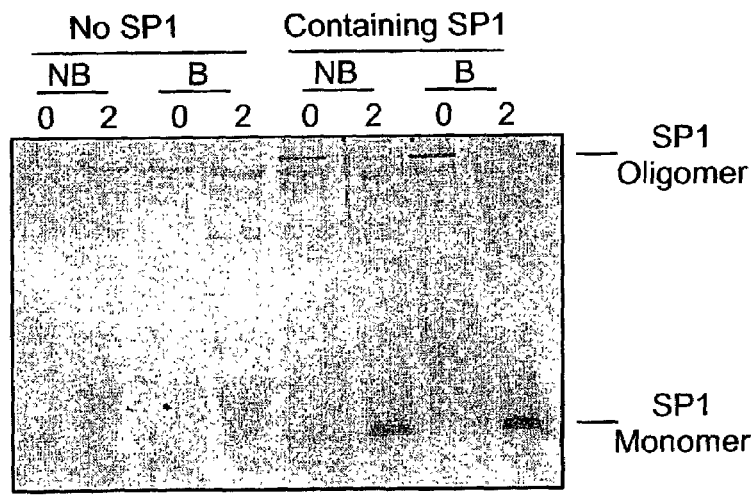

FIG. 8 demonstrates the boiling-stable properties of recombinant SP1 expressed in *Pichia pastoris*. Culture medium of control and SP1-transformed *Pichia pastoris* cells was either boiled (B) or not boiled (NB) for 10 minutes and then centrifuged for 10 minutes at 10,000 g. Supernatant samples were prepared in either full strength (2%) SDS sample buffer (lane 2) or native (0% SDS) sample buffer (lane 0), boiled for 5 minutes, and separated on 17% polyacrylamide SDS-tricine gel. No SP1: Culture medium from *Pichia pastoris* without SP1 sequences. Containing SP1: Culture medium from *Pichia pastoris* secreting recombinant SP1.

Figure 9:
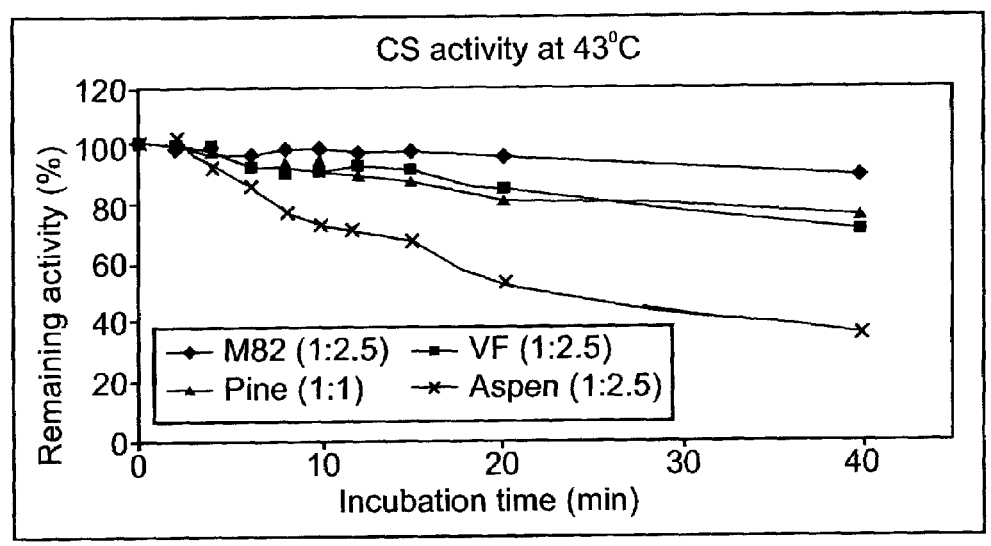

FIG. 9 demonstrates the prevention of heat inactivation of CS by boiling-stable protein fractions from plants. CS activity at 43° C. was assayed (as described in the Examples section that follows) at successive intervals in the presence of boiling-stable proteins extracts of tomato M82, tomato VF36 or aspen (CS: protein equals 1:2.5 µgram per milliliter) or BSA (HRP:BSA molar ratio 1:300).

Figure 10:
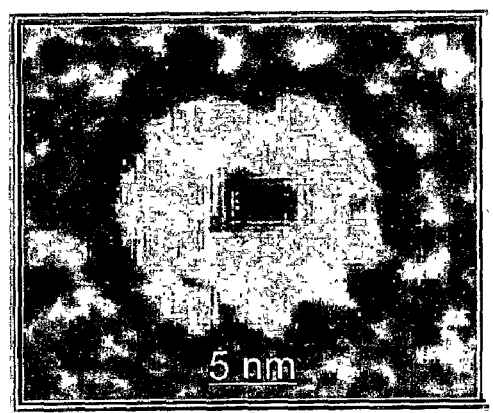

FIG. 10 depicts a transmission electron microscopic (TEM) image of SP1 molecular structure. The image represents the average of 51 particles made by rotational and translational alignment.

Figure 11:
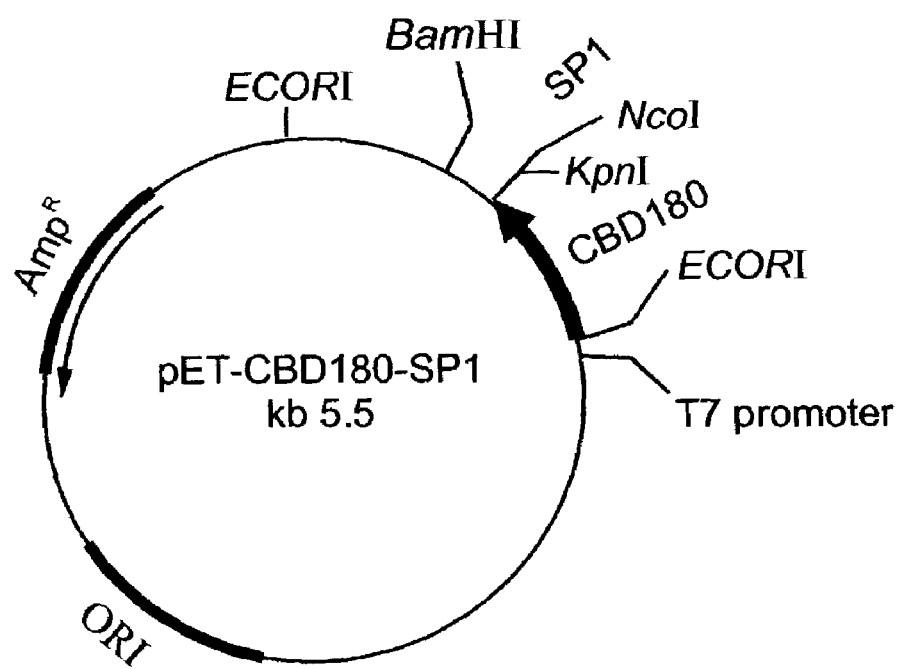

FIG. 11 depicts the plasmid construct pET-CBD180-SP1, containing the SP1 cDNA sequence (SEQ ID NO:1) inserted downstream of the CBD-180 element, between the NcoI and BamHI restriction sites.

FIG. 12 depicts the comparison of sequence homology between the putative SP1 polypeptide (SEQ ID NO:2) and the putative peptide sequences from homologous ESTs from various related and non-related plant species (SEQ ID NOs:7-32; Plurality 10.00; threshold=4.00; average weight=1.00; average match=2.91; average mismatch=minus 2.00). Consensus sequences (SEQ ID NO:33) are indicated for each 50 residue grouping.

FIG. 13 depicts the comparison of sequence homology between the putative SP1 polypeptide (SEQ ID NO:2) and the putative peptide encoded by a certain pop3 mRNA (SEQ ID NO:34).

Figure 14A:
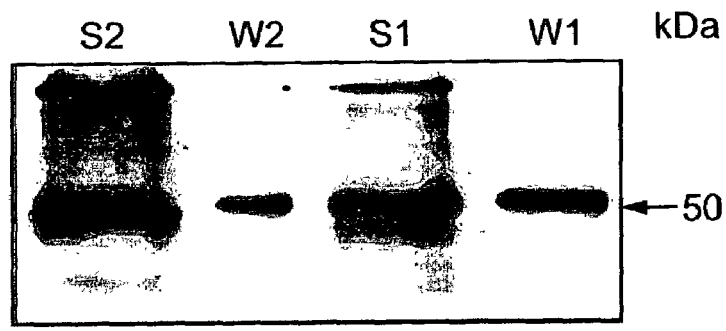
Figure 14B:
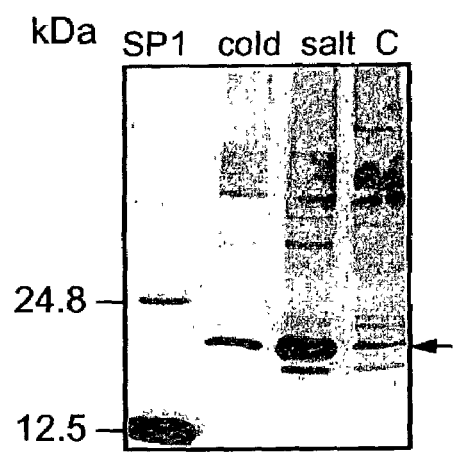
Figure 14C:
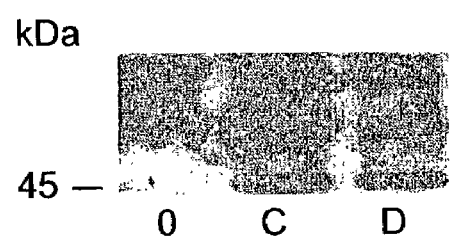
Figure 14D:
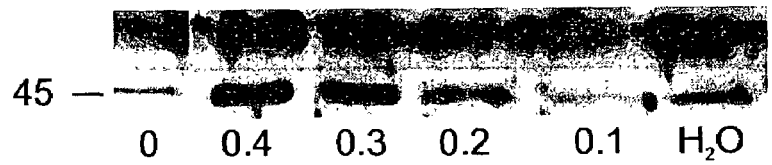

FIGS. 14*a-d* depict the immunodetection of SPs from pine and tomato having antigenic cross-reactivity to SP1. Total boiling stable proteins from pine (FIGS. 14*a* and 14*b*) and tomato (FIGS. 14*c* and 14*d*) were prepared (as described in the Examples section that follows), separated on PAGE, blotted onto nitrocellulose and the cross-reactive proteins immune-detected with anti-SP1 or anti-recombinant SP1 antibodies. FIG. 14*a* depicts the immune cross-reactivity of boiling stable proteins from pine (Pinus halepensis) needles in rainy (lanes W1 and W2) or dry (lanes S1 and S2) seasons after separation on 12.5% SDS-glycine PAGE, blotting onto nitrocellulose and reaction with anti recombinant SP1 (anti-CBD-SP1) antibodies. FIG. 14*b* depicts the immune cross-reactivity of boiling stable proteins from 36 hours cold treated (cold), 3 days salt treated (salt) or untreated (C) pine seedlings with purified aspen SP1 (SP1) after separation on 17% SDS-tricine PAGE, blotting onto nitrocellulose and reaction with anti native (oligomeric) SP1 antibodies. FIGS. 14*c* and 14*d* depict the immune cross-reactivity of boiling stable proteins from tomato (*Lycopersicum esculentum*) leaves. Extracts from leaves subjected to detachment with drought stress (FIG. 14*c*) (lane D), without drought stress (C) or detachment alone (0); or detachment with (lanes 0, 0.1, 0.2, 0.3 and 0.4 M NaCl) or without ($H_2O$) salt stress (FIG. 14*d*) were separated on 17% SDS-tricine PAGE, blotted onto nitrocellulose and reacted with anti recombinant (anti-CBD-SP1) antibodies.

Figure 15:
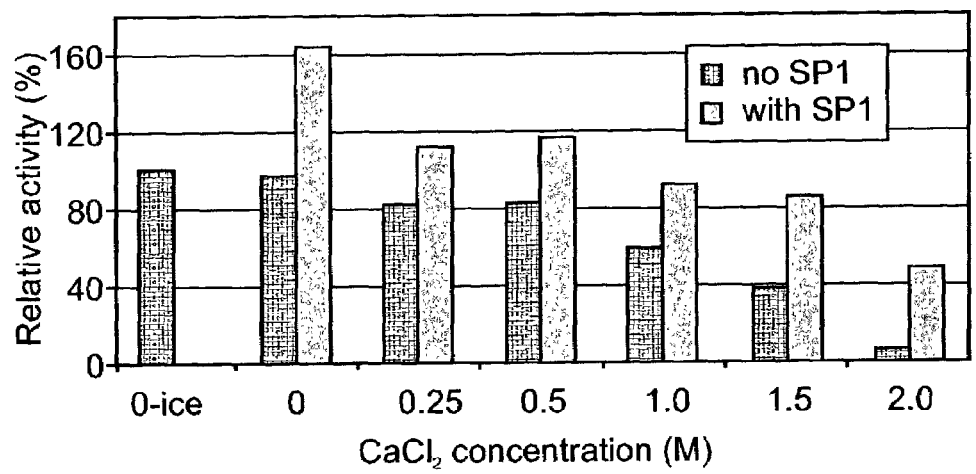

FIG. 15 is a bar graph demonstrating that SP1 protects α-amylase from $CaCl_2$ induced inactivation. α-Amylase (Sigma, A 6380, dissolved in 20 mM Tris-HCl buffer pH 7.0, containing 6 mM NaCl, 0.2 mg/ml) was incubated in the presence of increasing $CaCl_2$ concentration at room temperature (25° C.) for 2 HOURS in the absence or presence of SP1 (0.7 µM, of the 12-mer complex) (α-amylase:SP1 molar ratio 6:1). α-Amylase activity was measured using 'SIGMA DIAGNOSTICS AMYLASE' (Sigma, Cat No. 577-3) and was expressed as percentage of the untreated enzyme (0-ice).

Figure 16:
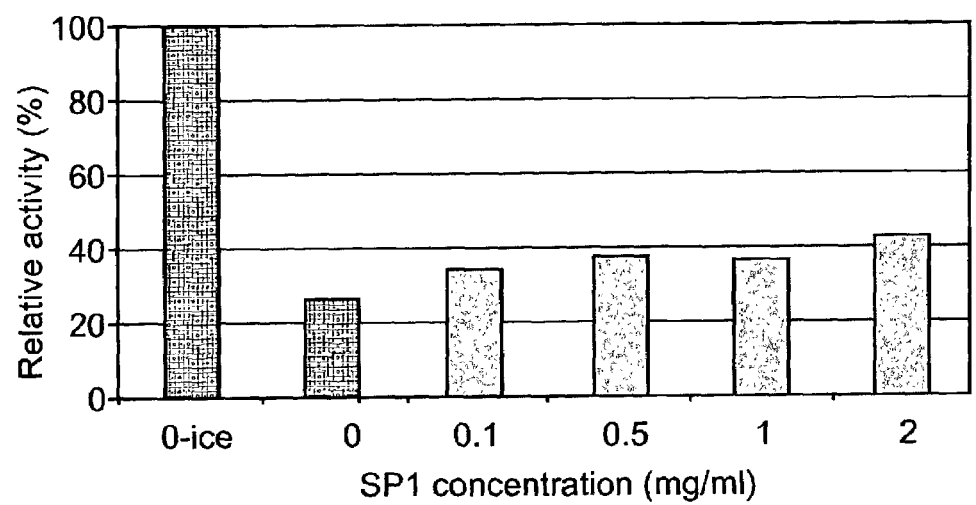

FIG. 16 is a bar graph demonstrating that SP1 protects α-amylase activity during incubation at room temperature. α-Amylase (Sigma, A 6380, dissolved in 20 mM Tris-HCl buffer pH 7.0, containing 6 mM NaCl, 0.2 mg/ml) was incubated at room temperature (25° C.) for one week in the absence (0) or presence of SP1 at various concentrations. α-Amylase activity was tested by measuring the amount of starch remained after being hydrolyzed by α-amylase. The activity is defined as milligrams starch that was hydrolyzed by one milligram of α-amylase per minute at 37° C. The relative activity in this Figure is expressed as percentage of untreated enzyme (0-cold).

Figure 17:
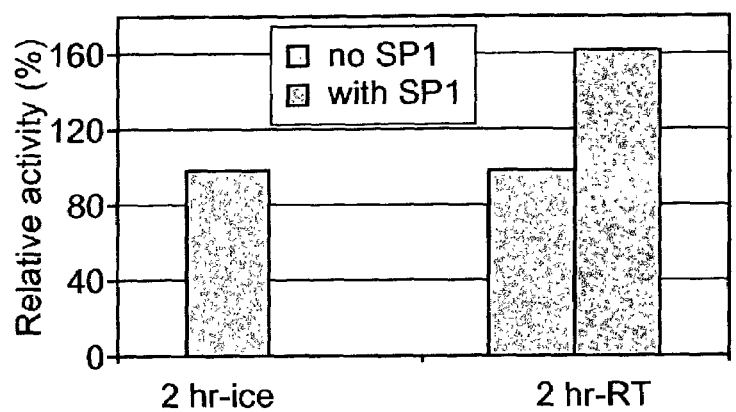

FIG. 17 is a bar graph demonstrating that SP1 repairs α-amylase activity. α-amylase (Sigma, A 6380, dissolved in 20 mM Tris-HCl buffer pH 7.0, containing 6 mM NaCl, 0.2 mg/ml) was incubated with 0.1 mg/ml (0.7 µM) SP1 at room temperature (25° C.). α-Amylase activity was tested 2 hours later, using 'SIGMA DIAGNOSTICS AMYLASE' (Sigma, Cat. No. 577-3). The amylase:SP1 monomeric molar ratio was 6:1.

Figure 18:
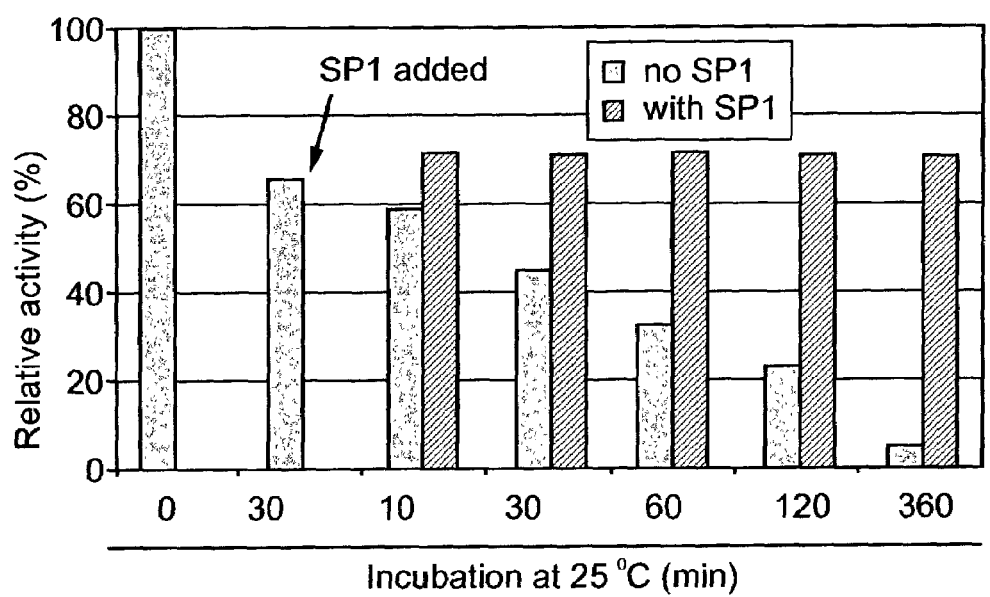

FIG. 18 is a bar graph demonstrating that SP1 repairs damaged HRP. Diluted HRP solution (5 nM in 40 mM HEPES buffer, pH 7.5) was incubated at room temperature (25° C.) for 30 minutes, followed by SP1 or buffer addition (170 nM, corresponding to a 12-mer complex molar ratio of HRP:SP1 of 1:17). HRP activity was measured at different time points as indicated. The relative activity was calculated as the percentage of non-treated enzyme (0 time).

Figure 19:
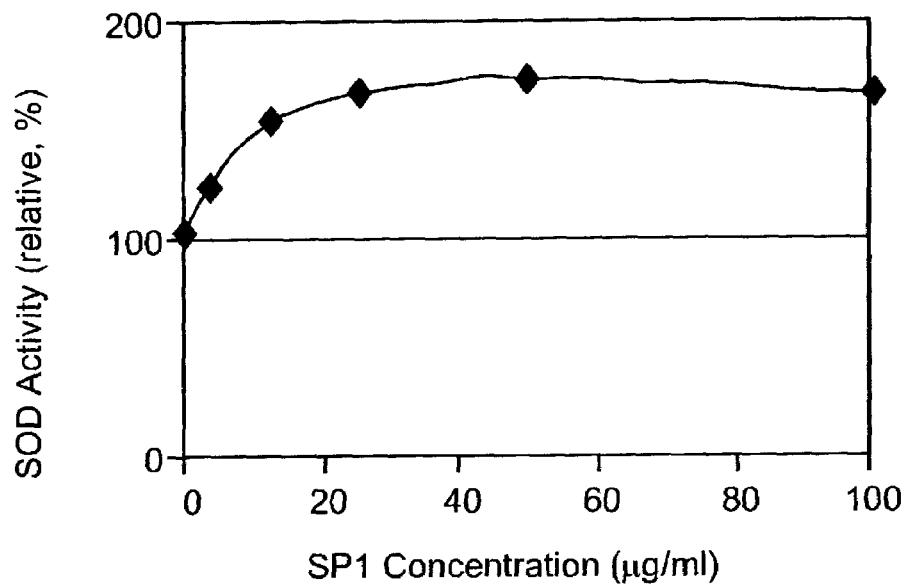

FIG. 19 is a plot demonstrating that SP1 repairs SOD activity. Cosmetic grade SOD ("dismutin", Pentapharm Ltd.) was 1000-fold diluted in 50 mM Acetate/Tris buffer, pH 5.5, 1.0 mM EDTA (final SOD concentration 10 Units/ml, wherein SOD unit is defined as the amount of enzyme which, under specified conditions of the assay, cause a 50% inhibition in the rate of reduction of pyrogallol) and was incubated at 37° C. in the absence or presence of SP1 in the indicated concentrations. SOD reaction conditions was determined in disposable plastic 1 ml cuvett at 25° C., as follows: 100 µl of SOD solution (10 U/ml) was mixed with 800 ml of Tris/Acetate buffer, pH 8.3, 1.0 mM EDTA and 100 µl of freshly made solution of 2 mM pyrogaloll which was dissolved in the same buffer (final concentration of 0.2 mM). The final pH in the reaction buffer was 8.0. Optical density was recorded after 60 minutes at 420 nm at room temperature.

Figure 20A:
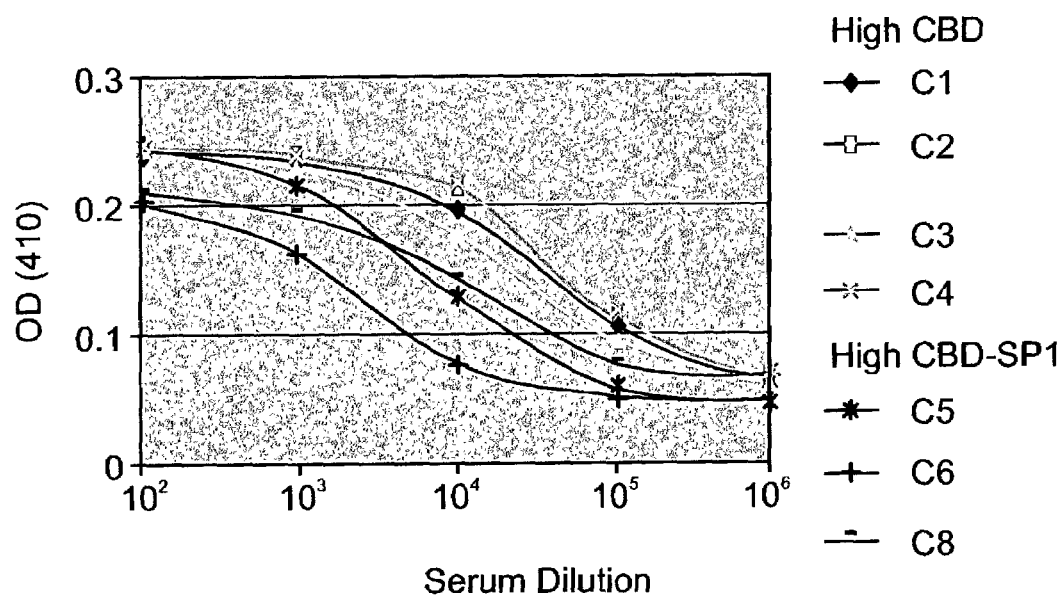

FIGS. 20*a* and 20*b*(i)-(iv) are graphs demonstrating that the immune response against CBD of mice injected with CBD is far higher than mice injected with CBD-SP1 fusion. 16 mice (C57BL/6) were injected (100 µl) with either CBD {5 µM (micel-4), 0.05 µM (mice 9-12)} or CBD-SP1 fusion protein} 5 µM (mice 5-8), 0.05 µM (mice 12-16)}. Two injections were given to each mice at day 0 and day 21. Mice were bled just before the first immunization (NIS) 14, 21 and 35 days after the first immunization. Antibody activity in the serum was tested using ELISA with CBD as antigen and HRP conjugated anti mouse antibody for detecting amount of bound antibody. To this end, plates were coated with CBD (1.0 μg/ml PBS, 120 μg/well for 2 hours, at 37° C.). Blocking was performed using 1% BSA in PBS for 1 hour at 37° C. First antibody reaction was conducted by diluting sera in 1% BSA in PBS for 1 hour at 37° C. All washing steps were conducted five times with PBS supplemented with 0.1% TWEEN-20. Second antibody reaction was conducted with HRP conjugated anti mouse IgG (Sigma, diluted 1/10000, v/v). Color development was stopped by 1 M sulfuric acid after 5 minutes incubation with TMB substrate (3,3',5,5'-tetramethylbenzidiine, PIERCE).

Figure 21A:
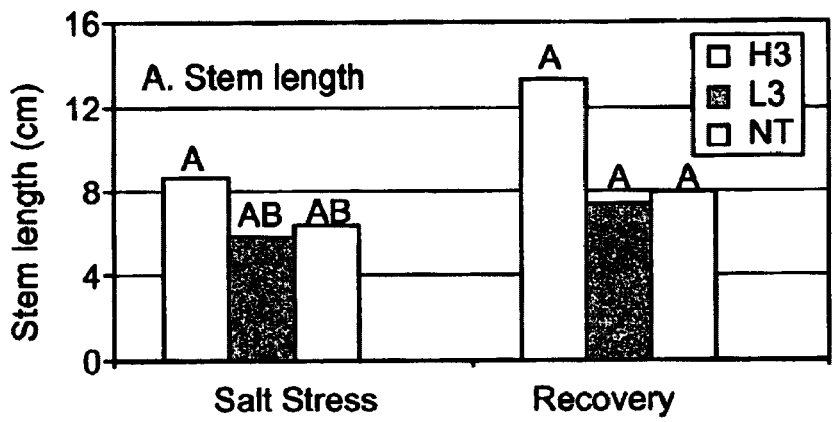
Figure 21B:
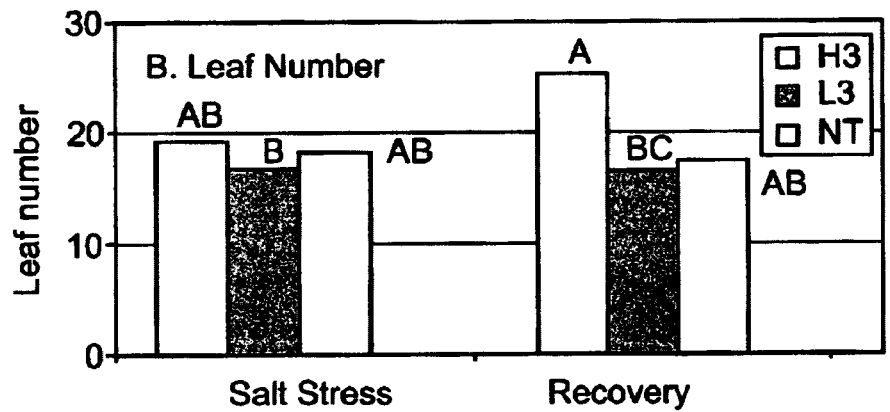
Figure 21C:
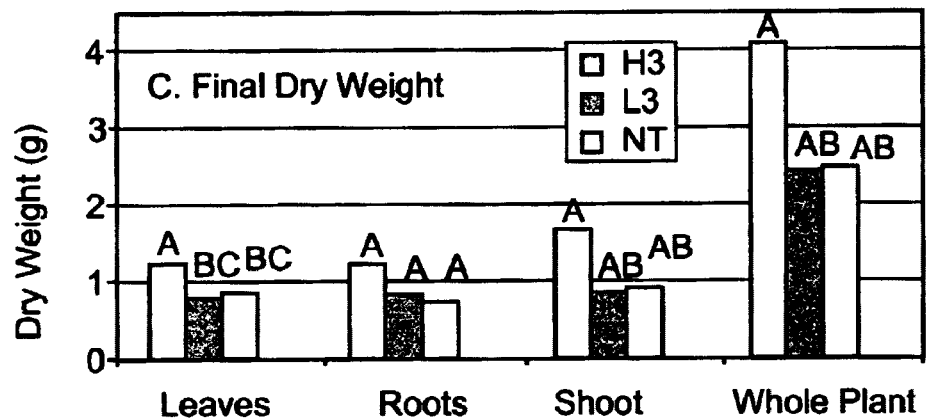

FIGS. 21a-c are bar graphs demonstrating stem elongation, leaf retention and dry weight of aspen plants following salt stress and recovery from stress. Aspen plants were transformed with a vector harboring the sp1 gene under the control of the constitutive promoter CaMV 35S. Two selected sp1-transgenic aspen lines, showing different level of SP1 expression, as well as the non-transformed plant (NT), were tested for salt tolerance. In vitro cloned aspen plants were acclimated in greenhouse and hardened in half-liter-pots containing 1:1 verniculite:garden medium. A block experiment, with groups of six plants for each line and each treatment was designed in a controlled greenhouse (26° C. in day time and 20° C. at night). Control plants were irrigated daily with tap water (250 ml per pot) containing 200 ppm of fertilizer (7/3/7, NPK). Salt-stressed plants were irrigated as the control, but supplemented with 150 mM NaCl and CaCl2 (in a molar ratio of 6:1), for 3 weeks, i.e., "stress period". At the end of the salt treatment, all plants were irrigated for additional 3 weeks without salt, i.e., "recovery period". Stem length and number of leaves, as well as leaf samples for measuring osmotic potential, were taken every week during the stress and recovery periods. The fresh and dry weights were taken at the end of the experiment.

FIG. 22 is a bar graph demonstrating SP1 effect on wound healing. Human fibroblast cells were seeded at a density of 200,000/petri-dish (4 cm in diameter) in a growth medium (2 ml of DEME medium containing 10% FCS, 2% glutamine and antibiotics). The medium was changed every two days until cells reached confluecy. A scratch was made with a micropipette tip (1 ml tip) and the dish was washed twice in PBS, in order to remove loosened debris. Four randomly selected spots along the scratch were marked using a marker pen on the bottom of the dish. Fresh medium without or with 5 μg/ml of plant derived SP1 protein was added to the medium. The cells were incubated at 37° C. for 28 hours. The scratch in each plate was recorded at time 0 and 28 hours by taking the pictures of the four-marked spots along the scratch, using a video-camera connected to a inverted microscope. All images were taken in the same magnification. The distance of the scratch was measure on these pictures. The data were averaged for 12 images of 3 replica petri-dishes. In the Figure, confluent was calculated as percentage of initial scratch.

FIGS. 23a-b are a photograph of a gel and a Table demonstrating that CBD-SP1 binds to cellulose as CBD protein does and protects HRP as SP1 does. Equal amount of CBD and CBD-SP1 proteins (15 pmol, calculated based on CBD molecular weight) were applied to 30 mg of cellulose (Sigmacell type 20). The protein samples were collected before applied to the cellulose (Before binding), before elution from cellulose (Binding) and after elution from cellulose (Elution). Protein samples from each stage were mixed with SDS-sample buffer, boiled for 5 min, and separated in 15% tricine-SDS-PAGE. For HRP protection assay, a 100 μl aliquot of HRP (Sigma, 5 nM in 40 mM HEPES buffer pH 7.5) was incubated at 25° C. in the presence of SP1 or SP1-CBD fusion protein at different concentrations. Aliquots were removed after 16 hours to determine remaining enzymatic activity. HRP reaction conditions were determined as follows: 5 μl of 5 nM HRP and 100 μl of TMB substrate (3,3',5,5'-tetramethylbenzidiine; PIERCE) were incubated at 25° C. The reaction was stopped after 10 min by addition of 1 M sulfuric acid and was recorded by a microplate reader at 435 nm. Colorimetric reaction of HRP as well as HRP substrate concentration was determined to be in the linear range. The protection units are the dilution factor of an SP1 solution at a concentration of 1 mg/ml that confers 50% protection of HRP activity under the above conditions.

FIGS. 24a(i)-(ii) and 24b are photographs demonstrating SP1 protein production from plants and recombinant bacteria. E. coli strain BL21(DE3) was transformed with a plasmid carrying SP1 gene (pET29a, kanamycin resistance conferred) and was grown in M9 minimal medium (Sambrook et al., 1989) containing kanamycin A (Sigma K4000; 50 μg/ml) to (O.D.$_{(600\ nm)}$)=0.05. This procedure was repeated for a total of five successive dilutions and regrowths. Sterile glycerol was added to a final concentration of 15% (v/v). 40 μL aliquots were dispensed aseptically into sterile tubes and stored in −80° C. Growing of bacteria carrying recombinant SP1 gene: An aliquot of bacterial glycerol stock (40 μl) was aseptically diluted 250 times into 12 ml of M9 minimal medium (Sambrook et al., 1989) containing kanamycin A and grown to O.D.$_{(600\ nm)}$ of 1-3. This culture was diluted 120 times into complex medium and grown to O.D.$_{(600\ nm)}$ of 0.8. At this point, the culture was induced by addition of isopropyl-β-D-thiogalactopyranoside (IPTG, 0.5 mM), and culture was allowed to grow for another four hours. Cell were harvested by centrifugation (10000 g, 15 minutes, 4° C.), and cells pellet was stored frozen at −80° C. Extraction and Purification of recombinant SP1 from bacteria Preparation of bacterial storage cultures: Bacteria cells pellet was suspended in Tris HCl buffer (30 mM; pH=10.5; 180 g/liter; OD$_{(600\ nm)}$=100-120) sonicated on ice (1 hour, pulses of 40% of full capacity) until turbidity declined four fold. Triton-X-100 and lysozyme were added (0.1% and 10 μg/mL, respectively), incubated with gentle stirring (1 hour at 37° C.), followed by centrifugation (15000 g, 15 minutes, 4° C.). Pellet was discarded, NaCl and MgCl$_2$ were added to supernatant (150 mM and 2.5 mM, respectively) and the pH was adjusted to 8.3 with HCl. To digest nucleic acids, solution was incubated with Benzonase (Sigma, Cat No. E1014; 0.3 unit/ml) with gentle stirring (12 hours at 37° C.). To digest protein, NH$_4$HCO$_3$ and Subtilisin (Sigma, Cat. No. P5380) were added to the extract (0.1 M and 1 μg/ml, respectively) and the solution was incubated with gentle stirring (12 hours at 37° C.). To remove boiling sensitive proteins extract was boiled (10 minutes), cooled on ice and centrifuged (10000 g, 15 minutes, 4° C.). Supernatant was filtered through filter paper (Whatman number 42) and membrane filters (Schleicher & Schull ME-28, 1.2 μm pore size and ME-25, 0.45⁻ μm pore size). Filtrate was concentrated and washed with Tris buffered saline or with phosphate buffered saline until filtrate became colorless. Protein concentration was measured using the Bradford method and SP1 as standard, and adjusted to 10 mg/ml. Thimerosal (Sigma, Cat No. T8784) was added (50 ppm). Solution was dispensed to screw capped amber vials as 1 ml aliquots and stored in dark at 4° C. FIG. 24a(i) (from left to right) Lane 1—Crude extract of poplar leaves. The sample was mixed with Tricine application buffer and boiled for 10 min prior to application on the gel; Lane 2—Crude extract of poplar leaves following boiling for 10 minutes and centrifugation. The sample was mixed with Tricine application buffer and boiled for 10 minutes prior to application on the gel. FIG. 24a(ii) (from left to right) Lane 1—Crude extract of recombinant protein expressed in *E. coli*. The sample was mixed with Tricine application buffer and boiled for 10 minutes prior to application on the gel; Lane 2—Crude extract of recombinant protein expressed in *E. coli* following boiling for 10 minutes and centrifugation. The sample was mixed with Tricine application buffer and boiled for 10 min prior to application on the gel. FIG. 24b— Recombinant SP-1 is resistant to boiling and proteolysis (From left to right): Lane 1, Crude extract: solubilized bacteria (see text above); Lane 2—Supernatant of Crude extract following boiling for 10 minutes and centrifugation. The sample was mixed with Tricine application buffer and boiled for 10 min prior to application on the gel. Lane 3—Supernatant of Crude extract following boiling for 10 minutes and centrifugation. The sampel was mixed with Tricine application buffer but was not boiled prior to application on the gel. Lane 4—Crude extract following Proteinase K treatment. The sample was mixed with Tricine application buffer and boiled for 10 minutes prior to application on the gel. Lane 5—Crude extract following Proteinase K treatment. The sample was mixed with Tricine application buffer and but was not boiled prior to application on the gel.

Figure 25:
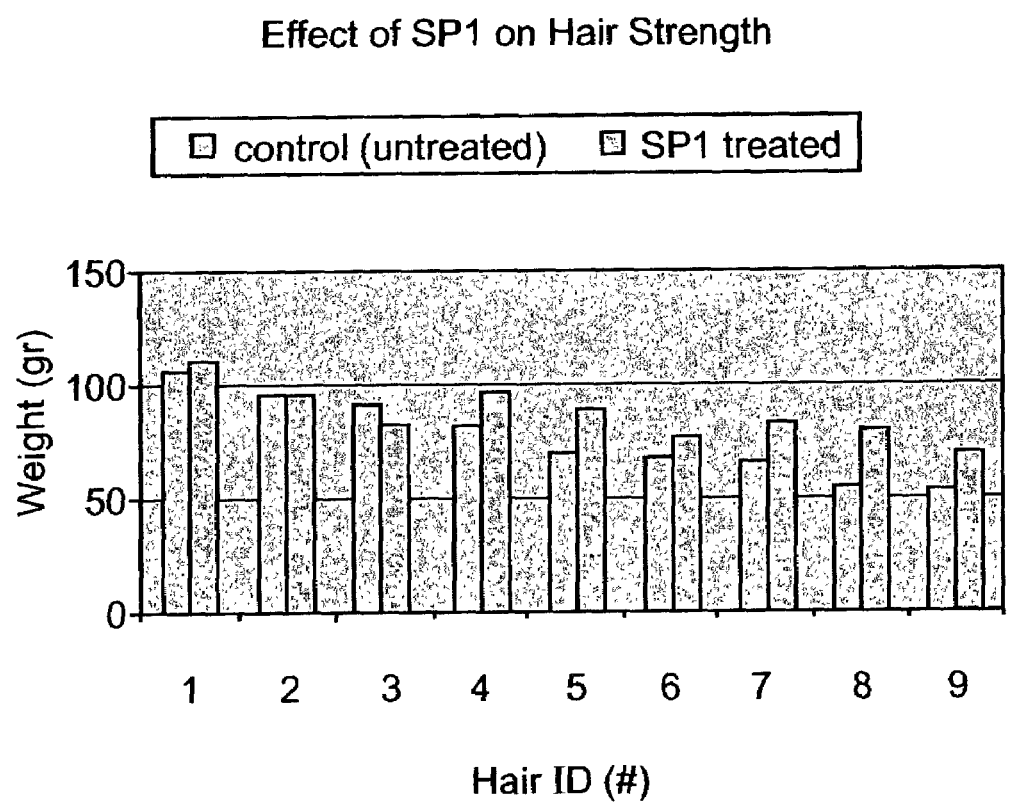

FIG. 25 is a bar graph demonstrating the effect of SP1 on human hair. Human hair, about 20 cm in length, was taken from one individual. Each hair was cut into two fragments, each about 10 cm in length. One fragment was incubated for 10 minutes at room temperature in Tris buffer solution {(100 mM; pH 8.0), control} and the other was incubated in the same buffer containing SP1 (50 µg/ml; SP1 treated hair). The hair was dried in air for 10 minutes, and the strength of each individual fragment was compared with the strength of the other. Each hair fragment was taped using masking tape to a metal rod and on the other end to the handle of a plastic cup. The cup was hanged from the metal rod through the hair. Weigh was increased gradually by adding water to the cup until the hair was torn. Strength was defined as the weight above which the hair was torn. The probability that the strength of the SP1 treated hair is higher than those of the control hair is 97%, as determined by paired Student t-test.

DESCRIPTION OF THE PREFERRED EMBODIMENTS

The present invention is of (i) a novel denaturant (e.g., boiling and/or detergent) stable and/or protease resistant, homo-oligomeric proteins, also referred to herein as stable proteins (SPs), having chaperone-like activity; (ii) methods of production, purification and increasing the specific activity of SPs; (iii) nucleic acids encoding SPs; (iv) methods of isolating nucleic acids encoding SPs; (v) antibodies recognizing SPs; (vi) the use of SPs for stabilizing, refolding, activating, preventing aggregation and/or de-aggregating macromolecules, proteins in particular; (vii) fusion proteins including SPs; (viii) nucleic acid constructs encoding the fusion proteins; and (ix) their use for immunization. Additional aspects and applications of the invention are further discussed below.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice a novel, major boiling stable protein was purified from water-stressed aspen plants (referred to herein as SP1). In the native state, as demonstrated by SDS-PAGE, SP1 exists as a high-molecular weight oligomeric complex of 116 kDa, which is stable at temperatures in excess of 80° C., and in the presence of high concentrations (up to 600:1 molar ratio SDS:SP1 monomer) of SDS. The oligomeric SP1 complex is convertible to its monomeric form (12.4 kDa) only when subjected to a combination of extreme temperature (100° C.) and high (greater than, or equal to, 600:1 molar ratio SDS:SP1 monomer) SDS concentrations.

Further, while reducing the present invention to practice, it was shown that native SP1 from crude proteins extract of water-stressed aspen demonstrated resistance to proteolytic digestion with proteinase K. When extracted from liquid nitrogen-homogenized aspen plant material, the predominant soluble protein remaining following 60 minutes digestion with proteinase K was identified as SP1. Furthermore, protease-purified SP1 protein maintains its oligomeric nature. Thus, SP1 exhibits resistance to proteolytic digestion and may be isolated and purified without detergent from plant material.

Further, while reducing the present invention to practice, gel-purified native SP1 was tested for its ability to stabilize and repair heat-labile proteins against thermal inactivation/aggregation. Citrate Synthase enzyme activity declines when incubated at 43° C. for 15 minutes, due to aggregation of the enzyme protein. Some sHsps (such as alpha-crystallin) are capable of preventing aggregation of the dimeric CS protein, but not reversing the inactivation of CS catalytic activity. The addition of SP1 protein (1:50 CS to SP1 monomer) conferred nearly complete thermal protection (93%) of CS enzyme activity for 40 minutes at 43° C. Lower concentrations of SP1 conferred significant, but proportionally less thermal stabilization. BSA, alpha-crystallin and glycerol were ineffective in protecting CS from thermal inactivation. Similar concentrations of native, purified oligomeric SP1 were also effective in protecting the monomeric enzyme, Horseradish Peroxidase (SP1 to HRP molar ratio of 300:1) from thermal inactivation of catalytic activity by prolonged exposure to 55° C. (53% activity remaining after 2 hours). In addition, native, purified oligomeric SP1 was effective in repairing the activity of Horseradish Peroxidase following thermal inactivation. Thus, SP1 exhibits chaperone-like ability to stabilize and repair monomeric and polymeric proteins during exposure to denaturing conditions, without inhibition of biological activity under non-denaturing conditions.

Further, while reducing the present invention to practice, poly-adenylated RNA from water-stressed aspen shoots was used to prepare cDNA for a lambda expression library in *E. coli*. A clone expressing a SP1 polypeptide sequence was identified by reactivity with polyclonal anti-SP1 antibodies raised against gel purified native SP1. When amplified and sequenced, the 567 nucleotide SP1 cDNA insert (SEQ ID NO:1) was found to contain an open reading frame representing the full-length coding sequence of the SP1 polypeptide monomer (SEQ ID NO:2). Analysis of the coding sequence indicated a highly hydrophilic protein, rich in Threonine, Alanine, Leucine, Glutamic and Serine residues, low in Tryptophan, and lacking Cysteines. No homology with other reported protein sequences was detected, but proteins exhibiting sequence homology with SP1 from various evolutionary distant (phylogenetically remote) plant species were identified using EST databases. Twenty five sequences with significant homology were identified (3 in Arabidopsis, 2 in maize, 1 in potato, 2 in rice, 1 in sorghum, 7 in soybean, 2 in tomato and 7 in wheat, SEQ ID NOs:7-32). 96.6% homology is found between SP1 and a Populus trichocarpa×Populus deltoides pop3 mRNA sequence (SEQ ID NOs:34 and 35 for nucleic acid and amino acid sequences, respectively). The putative peptide sequences were aligned and compared with the peptide sequence of SP1 (SEQ ID NO:2), revealing a few conserved consensus sequences: "HAFESTFES" (61-75, SEQ ID NO:36), "VKH" (9-11, SEQ ID NO:37) and "KSF" (47-49, SEQ ID NO:38), for example, indicating that SP1 is a member of a family of protein genes with wide representation in both monocotyledonous and dicotyledenous plant genomes. However, except for SP1 no function has been discovered or ascribed for any of the proteins in this family.

Further, while reducing the present invention to practice, when the open reading frame of SP1 cDNA was inserted in the proper orientation downstream of the CBD element of the pET-CBD-180 CBD expression vector, a nucleotide sequence coding for a CBD-SP1 fusion protein was obtained. The recombinant CBD-SP1 fusion protein was detected in inclusion bodies of transformed bacteria. On SDS-PAGE, the fusion protein migrated at 32.4 kDa, and was highly immunoreactive as was determined by Western blot analysis with polyclonal anti-SP1 antibodies. Thus, the fusion protein and the native SP1 have common epitopes. This antigenic identity was further demonstrated upon generation of polyclonal anti-CBD-SP1 antibodies. Taking advantage of the CBD element's affinity for cellulose, recombinant CBD-SP1 protein was purified on cellulose beads. A polyclonal antibody was raised against the highly purified fusion protein. The anti-CBD-SP1 antibody and the anti-native SP1 antibodies both recognized the same SP1 and CBD-SP1 fusion protein on SDS-PAGE of gel-filtration HPLC-purified native (172.5±1.25 kDa) and recombinant (267.5±2.5 kDa) proteins. Thus, recombinant SP1 sequences retain the antigenic and oligomeric-forming properties of the native protein.

Further, while reducing the present invention to practice, secretion of a non-fused, recombinant SP1 was achieved by cloning a portion of the SP1 coding sequence in-frame into a secretory P. pastoris expression vector pPIC9K and transforming host plant cells with verified in-frame constructs. Screening and induction of high-level expression revealed that recombinant SP1 is secreted into the culture medium. The non-fused, recombinant SP1 secreted by P. pastoris was found to be antigenically cross-reactive with anti-native SP1 and anti-recombinant CBD-SP1 polyclonal antibodies.

Further, while reducing the present invention to practice, the recombinant SP1 recovered from the P. pastoris culture medium was subjected to extreme denaturing conditions, and visualized on SDS-PAGE. Like the native protein, recombinant SP1 remained as an oligomeric complex following exposure to high detergent concentrations (e.g., 2% SDS) or high temperatures (e.g., boiling). Only the combination of the two extremes, high SDS concentration and boiling, caused the protein to migrate as the monomeric form on SDS-PAGE. Thus, recombinant SP1 also retains the antigenic and boiling-and detergent-stable oligomeric character of the native SP1 protein.

The recombinant SP1 polypeptides have chaperone-like activity similar to the native SP1. At a relatively low monomeric molar ratio (20:1 CBD-SP1:CS ratio), the purified CBD-SP1 fusion protein conferred significant (73%) protection against thermal inactivation of Citrate Synthase (CS) activity. A lower CBD-SP1 to CS ratio (5:1) led to proportionally less protection (33%), while incubation of the CS with higher concentrations of lysozyme or alpha-crystallin had no stabilizing effect on CS enzyme activity. Thus, the portion of the SP1 protein encoded by the cloned SP1 sequence retains both the antigenic and thermal stabilizing properties of the native protein.

The oligomeric nature of SP1 was examined via transmission electron microscopic (TEM) imaging. The images revealed an oligomer of 12 subunits, arranged in a ring-like arrangement having an external diameter of about 11 nm.

A major boiling-stable protein that was found to protect the catalytic activity of CS was detected in other phylogenetically remote, plants—tomato and pine. When separated on SDS PAGE, blotted onto nitrocellulose and immune-detected with anti-SP1 antibodies, the boiling stable proteins extracts from these remote species were found to contain cross-reactive proteins correlating to both monomeric and oligomeric structure of SP1. Furthermore, these cross reactive proteins from tomato and pine appeared to be drought, cold and salt-stress responsive. Thus, SPs from phylogenetically remote species and which exhibit immune cross-reactivity with SP1 also have chaperone-like activity.

Further while reducing the present invention to practice it was found that SP can be used for protecting an enzyme preparation from reduction in enzymatic activity, for repairing at least a portion of lost enzymatic activity of an enzyme preparation. It was further found that SP can be used for administering to an animal having an immune system a polypeptide, while reducing an immune response against the polypeptide. It was still further found that a transgenic plant expressing SP above a natural amount of SP is more tolerant to and more recoverable from abiotic stress. Similar behavior with respect to biotic stress, such as parasite infection, is anticipated. It was yet further found that SP can be used to increase cell migration and hence can be used for acceleration and/or induction of wound healing. It was also found that SP can be used to increase the strength of hair. It is anticipated that SP could be used to increase the strength of nails and skin as well.

Thus, according to one aspect of the present invention there is provided an isolated nucleic acid comprising a first polynucleotide encoding a denaturant (e.g., boiling and/or detergent) stable and/or protease resistant protein. The denaturant (e.g., boiling and/or detergent) stable and/or protease resistant protein encoded by the polynucleotide of this aspect of the present invention has a chaperone-like activity, which is assayable as is further described herein.

As used herein the phrase "denaturant-stable" refers to major (above 50%) structural oligomeric stability following a denaturation treatment in aqueous solution. A denaturation treatment can include boiling and exposure to a chemical denaturant, such as, a detergent (e.g., SDS), urea, or guanidin-HCl.

As used herein in the specification and in the claims section that follows, the phrase "boiling stable" refers to major (above 50%) structural oligomeric stability following treatment at substantially 100° C. in aqueous solution for at least 10 minutes, as determined by a size fractionation assay.

As used herein in the specification and in the claims section that follows, the phrase "detergent stable" refers to major (above 50%) structural oligomeric stability of an oligomeric protein following treatment in aqueous solution containing 1/2,000 molar ratio (monomer:SDS), as determined by a size fractionation assay.

As used herein in the specification and in the claims section that follows, the phrase "protease resistant" refers to major (above 50%) stability following treatment in aqueous solution containing 50 μg per ml proteinase K for at least 60 minutes at 37° C.

As used herein in the specification and in the claims section that follows, the phrase "chaperone-like activity" refers to the ability to mediate native folding and native oligomerization of proteins, to prevent the formation of incorrect protein structures, to unscramble existing incorrect protein structures and to limit stress-related damage by inhibiting incorrect interactions that could occur between partially denatured proteins or their domains. One such incorrect interaction could, for example, lead to the irreversible denaturation of enzyme proteins, as in Citrate Synthase, and significant loss of catalytic activity resulting from thermal extremes. Another incorrect interaction could cause aggregation of non-natively folded proteins, as a result of stress or in heterologous gene expression in transformed cells. By preventing such incorrect interactions, molecules having "chaperone-like activity" could confer thermal- and other stress-resistance to biologically active molecules, and prevent or even reverse aggregation of proteins.

The polynucleotide of the invention has a sequence which is at least 50%, preferably at least 60%, still preferably at least 65%, more preferably at least 70%, still more preferably at least 75%, preferably at least 80%, yet preferably at least 85%, preferably at least 90%, most preferably at least 95%, identical with SEQ ID NOs:1, 5, 6, 34, 39 or 40 or a portion thereof of at least 100, at least 150, at least 200 or at least 250 contiguous bases, as determined using the BestFit software of the Wisconsin sequence analysis package, utilizing the Smith and Waterman algorithm, where gap weight equals 50, length weight equals 3, average match equals 10 and average mismatch equals −9.

SEQ ID NO:1 is a cDNA encoding a stable protein (SP) from Aspen (SP1) which was cloned using an expression library and an anti-SP1 antibody raised against a major band of a heat-stable protein fraction. SEQ ID NO:34 is a homologous sequence. Using these or other homologous sequences, and conventional nucleic acid hybridization, reverse-transcription PCR or other techniques, or alternatively, using the anti-SP1 antibodies one of ordinary skills in the art can isolate (i) the genomic clone encoding for SP1; and (ii) CDNA and genomic clones of stable proteins from other species. It should further be emphasized in this context that SP1 is the major protein in a boiling stable protein fraction from water stressed Aspen, it is present in other plant species and it is therefore expected to be the most abundant protein in a boiling stable protein fraction of any plant, especially under water stress conditions, which renders the isolation thereof and polynucleotides encoding same rather simple by, for example, preparative gel electrophoresis, peptide isolation and microsequencing, followed by screening of appropriate genomic libraries using synthetic oligonucleotides or by RT-PCR.

Thus, according to another aspect of the present invention there is provided a method of isolating a gene encoding a stable protein having chaperone-like activity from a biological source, the method comprising screening an expression library with the polynucleotide described herein or a portion thereof. Additional gene isolation methods are discussed hereinbelow.

As used herein the phrase "complementary polynucleotide" or "cDNA" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein the phrase "genomic polynucleotide" includes sequences which originally derive from a chromosome and reflect a contiguous portion of a chromosome.

Preferably, the stable protein encoded by the polynucleotide of this aspect of the invention has a sequence at least 50%, preferably at least 60%, more preferably at least 65%, still more preferably at least 70%, still preferably at least 75%, preferably at least 80%, yet preferably at least 85%, preferably at least 90%, most preferably at least 95%, homologous (identical+similar amino acids) to SEQ ID NOs:2 or 35, as determined using the BestFit software of the Wisconsin sequence analysis package, utilizing the Smith and Waterman algorithm, where gap creation penalty equals 8 and gap extension penalty equals 2.

Alternatively or additionally, the polynucleotide according to this aspect of the present invention is preferably hybridizable with SEQ ID NOs:1, 5, 6, 34, 39 or 40, or with the nucleic acids encoding SEQ ID NOs:7-33, or portions thereof of at least 100, at least 150, at least 200 or at least 250 consecutive bases.

Hybridization for long nucleic acids (e.g., above 100 bp in length) is effected according to preferred embodiments of the present invention by stringent or moderate hybridization, wherein stringent hybridization is effected by a hybridization solution containing 10% dextrane sulfate, 1 M NaCl, 1% SDS and 5×10$^6$ cpm $^{32}$p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 50° C.

Thus, this aspect of the present invention encompasses (i) polynucleotides as set forth in SEQ ID NO:1 and 34 (ii) fragments thereof; (iii) sequences hybridizable therewith; (iv) sequences homologous thereto; (v) sequences encoding similar polypeptides with different codon usage; (vi) altered sequences characterized by mutations, such as deletion, insertion or substitution of one or more nucleotides, either naturally occurring or man induced, either randomly or in a targeted fashion. Each such sequence can be expressed using an expression system and the protein encoded thereby tested for stability and chaperone-like activity as is further described an exemplified herein in the Examples section that follows.

As used herein, the phrase "sequences with different codon usage" refers to polynucleotide sequence encoding polypeptides of identical amino acid residue sequence and number, differing in the base composition of one or more of the triplet codons specifying the amino acids. Such different codon usage is a function of the plurality of triplets encoding individual amino acid residues, and has been demonstrated for genes of homologous proteins in remote species such as mammals and protozoa, and for tissue-specific proteins of multi-copy gene families.

According to a preferred embodiment of the invention the isolated nucleic acid according to this aspect of the present invention further comprising a second polynucleotide harboring a promoter sequence for regulating the expression of the first polynucleotide in a sense orientation. Such promoters are known to be cis-acting sequence elements required for transcription as they serve to bind DNA dependent RNA polymerase which transcribes sequences present downstream thereof.

While the first polynucleotide described herein is an essential element of the invention, it is modular and can be used in different contexts. The promoter of choice that is used in conjunction with the polynucleotide of the invention is of secondary importance per se, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest, be it a bacteria, yeast or a higher cell of a plant or animal, including insect and mammal derived cells.

As used herein a "eukaryote promoter" refers to a promoter that can direct gene expression in eukaryotic cells. It can be derived from a eukaryote genome or from a viral genome capable of infecting a eukaryote cell.

As used herein a "prokaryote promoter" refers to a promoter that can direct gene expression in a prokaryote. It can be derived from a prokaryote genome or plasmid or from a viral genome capable of infecting a prokaryote cell.

As used herein in the specification and in the claims section that follows the phrase "plant promoter" includes a promoter which can direct gene expression in plant cells. Such a promoter can be derived from a plant, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric.

Promoters that can direct gene expression in subcellular organelles such as chloroplasts, chloroplastids or mitochondria, are also within the scope of the present invention. Such promoters may be operative also in prokaryotes.

The plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane baciliiform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

Examples of tissue specific promoters include, without being limited to, bean phaseolin storage protein promoter, DLEC promoter, PHSβ promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

The first (coding region) and second (promoter sequence) polynucleotides herein described preferably form a part of a nucleic acid construct which preferably has additional genetic elements as is further described below.

Thus, a construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

The construct of the present invention can be used to express the polypeptide encoded thereby in a variety of species ranging from bacteria such as *E. coli*, yeast cells or higher cells such as the cells of a plant. Expression can be selected stable or transient, as is further detailed hereinunder. Plants overexpressing a stable protein which has chaperone-like activity of the invention are expected to become stress adapted or tolerant, since the endogenous expression of SP1 and SP1-like proteins in plants correlates with stress induction (see FIG. 14 and the examples section).

Several nucleic acid transformation methods can be used to implement a method of generating stress tolerant plants according to the present invention.

Thus, there are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterthere is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et a. FEBS Letters (1990) 269:73-76.

When the virus is a DNA virus, the constructions can be made to the virus itself Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

Alternatively, the nucleic acid construct according to this aspect of the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stem cells that underwent a homologous recombination event with the construct. Further detail relating to the construction and use of knock-out and knock-in constructs is provided in, for example, Fukushige, S. and Ikeda, J. E.: Trapping of mammalian promoters by Cre-lox site-specific recombination. DNA Res 3 (1996) 73-80; Bedell, M. A., Jenkins, N. A. and Copeland, N. G.: Mouse models of human disease. Part 1: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62, which are incorporated herein by reference.

According to another aspect of the invention there is provided a transgenic plant expressing a denaturant stable and/or protease resistant protein, the denaturant stable and/or protease resistant protein having a chaperone-like activity above a natural amount of the denaturant stable and/or protease resistant protein having the chaperone-like activity in the plant.

Elevated native SP expression in plants is positively correlated to stress conditions. Overexpression of SP1 in plants resulted in (i) rendering the plant more tolerant to, and more recoverable following, a biotic stress.

Hence, according to another aspect of the present invention there is provided a method of rendering a plant more tolerant to a biotic or abiotic stress. The method according to this aspect of the invention is effected by engineering the plant to express a denaturant stable and/or protease resistant protein, the denaturant stable and/or protease resistant protein having a chaperone-like activity, above a natural amount of the denaturant stable and/or protease resistant protein having the chaperone-like activity in the plant.

According to another aspect of the present invention there is provided a method of rendering a plant more recoverable from a biotic or abiotic stress. The method according to this aspect of the invention is effected by engineering the plant to express a denaturant stable and/or protease resistant protein, the denaturant stable and/or protease resistant protein having a chaperone-like activity, above a natural amount of the denaturant stable and/or protease resistant protein having the chaperone-like activity in the plant.

According to still another aspect of the present invention there is provided an oligonucleotide of at least 17, at least 18, at least 19, at least 20, at least 22, at least 25, at least 30 or at least 40, bases specifically hybridizable with any of the polynucleotides described herein encoding a stable protein.

Hybridization of shorter nucleic acids (below 100 bases in length, e.g., 17-40 bases in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% at 1-1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction (PCR). The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and zero° C. Suitable oligonucleotide pairs can be selected using the OLIGO software.

Consequently, according to yet an additional aspect of the present invention there is provided a nucleic acid amplification product obtained using the pair of primers described herein. Such a nucleic acid amplification product can be isolated by gel electrophoresis or any other size based separation technique. Alternatively, such a nucleic acid amplification product can be isolated by affinity separation, either stranded affinity or sequence affinity. In addition, once isolated, such a product can be further genetically manipulated by restriction, ligation and the like, or it can be labeled, as required for further use.

According to a presently preferred embodiment of the invention the denaturant (e.g., boiling and/or detergent) stable and/or protease resistant protein encoded by the polynucleotide of the invention is natively a homo-oligomer of, for example, at least 10 subunits, optionally 12 or 14 subunits, arranged, for example, in a concentric arrangement, which homo-oligomer is denaturant (e.g., boiling and/or detergent) stable and/or protease resistant as these terms are herein defined. It will, however, be appreciated that the process of homo-oligomer formation of stable proteins may result in homo-oligomers of less subunits, as, at least for short time periods, partially assembled homo-oligomers of 2 or more subunits are expected.

According to another aspect of the present invention there is provided a method of isolating a gene encoding a denaturant (e.g., boiling and/or detergent) stable and/or protease resistant protein having chaperone-like activity from a biological source, the method comprising (a) extracting total proteins from the biological source, so as to obtain a proteins extract; (b) boiling the proteins extract; (c) collecting soluble proteins; (d) obtaining a purified boiling stable protein having chaperone-like activity; (e) raising antibodies recognizing the boiling stable protein having the chaperone-like activity; and (f) screening an expression library with the antibodies.

According to yet another aspect of the present invention there is provided a method of isolating a gene encoding a denaturant (e.g., boiling and/or detergent) stable and/or protease resistant protein having chaperone-like activity from a biological source, the method comprising (a) extracting total proteins from the biological source, so as to obtain a proteins extract; (b) boiling the proteins extract; and (c) collecting soluble proteins; (d) obtaining a purified boiling stable protein having the chaperone-like activity, by, for example, assaying the soluble proteins for chaperone-like activity and enriching or isolating a stable protein having chaperone-like activity; (e) microsequencing the stable protein having the chaperone-like activity, so as to obtain at least a partial amino acid sequence thereof; (f) designing an oligonucleotide corresponding to the amino acid sequence; and (g) screening a library with the oligonucleotide.

Design and synthesis of oligonucleotides corresponding to a given amino acid sequence and the use thereof for screening libraries are well known in the art, see, for example, the general references listed below in the Examples section. Such oligonucleotides can alternatively be used in a PCR, RT-PCR, RACE and the like procedures to isolate the gene by cDNA amplification.

There is also provided according to the present invention a method of isolating a nucleic acid potentially encoding a denaturant (e.g., boiling and/or detergent) stable and/or protease resistant protein having chaperone-like activity. The method according to this aspect of the invention is effected by screening a cDNA or genomic library with a polynucleotide of at least 17 bases, at least 60% identical to a contiguous portion of SEQ ID NOs:1, 5, 6, 34, 39 or 40. Such a polynucleotide can be a synthetic oligonucleotide as is further described hereinabove and is preferably labeled with a suitable label.

The present invention is further of a method of identifying a nucleic acid potentially encoding a denaturant (e.g., boiling and/or detergent) stable and/or protease resistant protein having chaperone-like activity. This method is effected by searching an electronic library containing a plurality of nucleic acid and/or amino acid sequences for sequences having a predetermined degree of identity or homology to any of SEQ ID NOs:1, 2, 5-35 or 39-40 or portions thereof of, or corresponding to, at least 15, at least 17, at least 20, at least 25, at least bases 30 or more bases.

Another aspect of the invention provides a method of isolating a nucleic acid potentially encoding a denaturant (e.g., boiling and/or detergent) stable and/or protease resistant protein having chaperone-like activity. The method comprising (a) providing at least one pair of oligonucleotides each independently being at least 15, at least 17, at least 20, at least 25, at least bases 30 or more bases in length, the at least one pair of oligonucleotides including at least one oligonucleotide corresponding to SEQ ID NOs:1, 2, 5-35 or 39-40, the at least one pair of oligonucleotides being selected for amplifying a nucleic acid having a degree of identity with, or encoding proteins homologous, to SEQ ID NOs:1, 2, 5-35 or 39-40; (b) contacting the at least one pair of oligonucleotides with a sample of nucleic acid and amplifying the nucleic acid having the degree of identity with, or encoding proteins homologous to, SEQ ID NOs:1, 2, 5-35 or 39-40; and (c) using the nucleic acid having the degree of identity with, or encoding proteins homologous to, SEQ ID NOs:1, 2, 5-35 or 39-40 for isolating a nucleic acid potentially encoding a denaturant (e.g., boiling and/or detergent) stable and/or protease resistant protein.

According to another aspect of the present invention there is provided a denaturant (e.g., boiling and/or detergent) stable and/or protease resistant polypeptide having a chaperone-like activity, effective, for example, in stabilizing proteins. Preferably, the polypeptide is encoded by a polynucleotide as described herein. Most preferably, the polypeptide has a sequence at least 50%, preferably at least 60%, more preferably at least 65%, still more preferably at least 70%, still preferably at least 75%, preferably at least 80%, yet preferably at least 85%, preferably at least 90%, most preferably at least 95%, homologous (identical+similar amino acids) to SEQ ID NOs:2 or 35, as determined using the BestFit software of the Wisconsin sequence analysis package, utilizing the Smith and Waterman algorithm, where gap creation penalty equals 8 and gap extension penalty equals 2. The polypeptide of this aspect of the invention is preferably natively a homo-oligomer, preferably a homo-oligomer of 14 subunits as is further detailed hereinabove. As is further detailed below, the polypeptide of the invention can be purified from a boiling stable/protease resistant fraction of plants. Alternatively, it can be manufactured using recombinant DNA technology as is further described and exemplified herein. It is shown in the Examples section that follows and it is further discussed hereinabove that a recombinant polypeptide of the invention and its corresponding native protein share similar oligomerization, epitope and chaperone-like activity properties.

The polypeptides of the present invention can be purified by any of the means known in the art. Various methods of protein purification are described, e.g., in Guide to Protein Purification, ed. Deutscher, Meth. Enzymol. 185, Academic Press, San Diego, 1990; and Scopes, Protein Purification: Principles and Practice, Springer Verlag, New York, 1982.

Thus, according to another aspect of the present invention there is provided a method of enriching or isolating a denaturant (e.g., boiling and/or detergent) stable and protease resistant protein having chaperone-like activity from a biological source. The method according to this aspect of the present invention is effected by (a) extracting total proteins from the biological source, so as to obtain a proteins extract; (b) boiling the proteins extract; (c) collecting soluble proteins; and optionally (d) assaying for chaperone-like activity of soluble proteins. Preferably, the method further comprises size fractionating the soluble proteins and assaying a fractionated protein for chaperone-like activity, as is further described herein.

As used herein, the phrase "isolating a protein", means identifying and separating and/or recovering a protein from a component of its natural environment. Contaminant components of its natural environment are materials that would interfere with diagnostic, therapeutic or commercial uses for the protein, and may include enzymes and other proteinaceous or non-proteinaceous solutes. As used herein, the phrase "enriching a protein" means separating a protein from at least 10%, and preferably 50% of the contaminating components of its natural environment, as mentioned above.

According to still a further aspect of the present invention there is provided a method of detergent-free isolation of a protease-resistant protein having chaperone-like activity from biological source. The method is effected by (a) extracting the soluble proteins preferably using a cold extraction procedure (e.g., at least −50° C., preferably −80° C.), so as to obtain a proteins extract; (b) contacting the protein extract with a protease; (c) isolating a protease-resistant protein; and optionally (d) assaying the protease-resistant protein for chaperone-like activity.

According to another aspect of the present invention there is provided yet another method of isolating a boiling stable protein having chaperone-like activity from a biological source. The method according to this aspect of the invention is effected by (a) extracting total proteins from the biological source, so as to obtain a proteins extract; (b) boiling the protein extract; (c) recovering soluble protein fraction; and optionally (d) assaying the protease-resistant protein for chaperone-like activity. A protease can also be used in this procedure.

According to still an additional aspect of the present invention there is provided a method of preventing an aggregating protein from aggregating into an aggregate. The method according to this aspect of the invention is effected by contacting an effective amount of the polypeptide described herein with the aggregating protein.

The "effective amount" for the purposes herein is determined by considerations which are known to the skilled artisan. The amount must be effective to induce in the contacted protein a significant increase in solubility under conditions otherwise producing aggregation, as assessed by physico-chemical or functional measurements, such as resistance to precipitation upon centrifugation, a decrease in refractile properties, decrease in molecular mass upon size fractionation on SDS-PAGE, HPLC, filtration, dialysis or any other size fractionation methodology; and/or retention of biological properties such as catalytic activity, molecular binding activity and antigenic properties.

According to a further aspect of the present invention there is provided a method of de-aggregating aggregates of an aggregating protein. The method according to this aspect of the invention is effected by contacting an effective amount of the polypeptide described herein with the aggregate.

Hence, the present invention provides a method of treating a disease associated with protein aggregation of an aggregating protein, the method comprising administering to a subject in need thereof a denaturant stable and/or protease resistant protein, the denaturant stable and/or protease resistant protein having a chaperone-like activity, in an amount sufficient for de-aggregating and/or preventing aggregation of the aggregating protein, the aggregating protein is, for example, beta-amyloid or prion, as is the case in Alzheimer's disease and prion associated diseases, e.g., encephalus spongyform.

According to yet a further aspect of the present invention there is provided a method of stabilizing a protein against denaturing conditions. The method according to this aspect of the invention is effected by contacting an effective amount of the polypeptide described herein to become in contact with the protein.

In this context, the present invention was reduced to practice with respect to citrate synthase and horseradish peroxidase, which are accepted model systems for evaluating protein anti-aggregation, stabilization and chaperone activity, as is further described and exemplified in the Examples section that follows.

According to still a further aspect of the present invention there is provided a method of protecting an enzyme preparation from reduction in enzymatic activity. The method according to this aspect of the invention is effected by adding to the enzyme preparation a denaturant stable and/or protease resistant protein, the denaturant stable and/or protease resistant protein having a chaperone-like activity, in an amount sufficient for protecting the enzyme preparation from reduction in enzymatic activity.

According to a further aspect of the present invention there is provided a method of repairing at least a portion of lost enzymatic activity of an enzyme preparation. The method according to this aspect of the invention is effected by adding to the enzyme preparation a denaturant stable and/or protease resistant protein, the denaturant stable and/or protease resistant protein having a chaperone-like activity, in an amount sufficient for repairing at least the portion of the lost enzymatic activity of the enzyme preparation.

According to yet an additional aspect of the present invention there is provided an antibody, either polyclonal or monoclonal antibody, recognizing at least one epitope of the polypeptide described herein. The present invention can utilize serum immunoglobulins, polyclonal antibodies or fragments thereof, (i.e., immunoreactive derivative of an antibody), or monoclonal antibodies or fragments thereof. Monoclonal antibodies or purified fragments of the monoclonal antibodies having at least a portion of an antigen binding region, including, such as, Fv, F(abl)2, Fab fragments (Harlow and Lane, 1988 Antibody, Cold Spring Harbor), single chain antibodies (U.S. Pat. No. 4,946,778), chimeric or humanized antibodies and complementarily determining regions (CDR) may be prepared by conventional procedures. Purification of these serum immunoglobulins, antibodies or fragments can be accomplished by a variety of methods known to those of skill, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies, including single chain antibodies, are well known in the art, as summarized for example in reviews such as Tramontano and Schloeder, Methods in Enzymology 178, 551-568, 1989. Purified native SPs, recombinant SPs or recombinant SP-fusion proteins (see below) of the present invention or immunogenic portions thereof including at least one immunogenic epitope may be used to generate the antibodies of the invention.

Preferably, the elicitation of the antibody is through in vivo or in vitro techniques, the antibody having been prepared by a process comprising the steps of, first, exposing cells (either in vivo or in vitro) capable of producing antibodies to a SP protein of the invention or an immunogenic portion thereof, thereby generating antibody producing cells. Second, imortalizing the antibody producing cells by, for example fusing them with mycloma cells or infecting them with a transforming virus, thereby generating a plurality of immortalized cells, each producing monoclonal antibodies, and third, screening the plurality of monoclonal antibodies to identify a monoclonal antibody which specifically binds SP. These methods are known in the art and are therefore not further elaborated herein.

According to still another aspect of the present invention there is provided a fusion protein comprising a denaturant (e.g., boiling and/or detergent) stable protease resistant polypeptide having a chaperone-like activity fused to an additional polypeptide. Preferably the fusion protein acquires an oligomeric form, with the advent that either homo- or hetero oligomeric forms can be assembled. Simultaneous display of a variety of proteins on the same SP oligomer can be achieved by reversible denaturation and re-assemble of mixtures of different fusion proteins as herein described or alternatively, by coexpression of several fusion proteins in the same cells/organism (in vivo assembly). Such fusion proteins can exhibit biological properties (such as substrate or ligand binding, enzymatic activity, antigenic activity, etc.) derived from each of the fused sequences. Any conventional fusion partner can be used, including, for example, beta-glucuronidase, beta-galactosidase, etc. Fusion polypeptides are preferably made by the expression of recombinant nucleic acids produced by standard techniques.

The following provides a non-exhaustive list of proteins having known genes which can be fused to a stable protein of the invention: proteins having medicinal properties: aggregating proteins such as beta amyloid, messenger proteins such as the cytokines IL-1 and IL-7, and their receptor proteins, proteins of agents of infectious diseases, such as bacterial exported proteins from *pneumococci, streptococci* and other pathogenic strains, proteins from pathogenic viruses such as hepatitis B and transmissible gastroenteritis, and from protozoa and helminths in parasitic infections; non-infectious diseases, such as poorly antigenic autologous tumor cell proteins or any of their epitopes, interferons and their receptor proteins in the case of autoimmune diseases, proteins useful in research, including protein or polypeptide reagents for immuno-assays such as insulin, gastrin, opiods, growth factors, calcitonin, malarial and other protozoan blood-stage antigens, enzymes such as peroxidase and heat or detergent labile biologically active proteins, including enzymes and proteins useful in commercial applications, e.g., proteases, glycosil-hydrolases and lipases, heterologous proteins aggregating in transformed cells or their culture media such as growth factors, glycosil-hydrolases, peroxidases, transferases, kinases, phosphatases, sulfatases, nucleic-acid-modifying enzymes (ligases, restriction enzymes, reverse-transcriptase, nucleic acid polymerases).

A fusion protein according to the present invention is obtainable by either genetic engeneering techniques by which two open reading frames are fused into a single nucleic acid creating a continous reading frame, the translation thereof in an expression system yields the fusion protein, or via chemical fusion or linking of pre-existing proteins, using anyone of a plurality of linking reagents known in the art for linking or joining proteins.

Hence, many methods are known in the art to conjugate or fuse (couple) molecules of different types, including proteins or polypeptides. These methods can be used according to the present invention to couple a stable protein with any other protein. Two isolated peptides can be conjugated or fused using any conjugation method known to one skilled in the art. One peptide can be conjugated to another using a 3-(2-pyridyldithio)propionic acid N-hydroxysuccinimide ester (also called N-succinimidyl 3-(2pyridyldithio) propionate) ("SDPD") (Sigma, Cat. No. P-3415), a glutaraldehyde conjugation procedure or a carbodiimide conjugation procedure.

SPDP conjugation—Any SPDP conjugation method known to those skilled in the art can be used. For example, in one illustrative embodiment, a modification of the method of Cumber et al. (1985, Methods of Enzymology 112: 207-224) as described below, is used. A first peptide (1.7 mg/ml) is mixed with a 10-fold excess of SPDP (50 mM in ethanol) and the seconf peptide is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS. The first peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-secong peptide in a molar ratio of 1:10 second peptide:first peptide and incubated at 4° C. overnight to form a peptide-peptide conjugate.

Glutaraldehyde conjugation—Conjugation of a peptide with another peptide can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques, Academic Press, San Diego) described below, is used. The peptides (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide conjugation—Conjugation of a peptide with another peptide can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of one peptide (resulting in the formation of an ester bond), or an amino group of the one peptide (resulting in the formation of an amide bond) or a sulfhydryl group of the one peptide (resulting in the formation of a thioester bond). Likewise, carbodiimide coupling can be used to form analogous covalent bonds between a carbon group of one peptide and an hydroxyl, amino or sulfhydryl group of the other peptide. See, generally, J. March, Advanced Organic Chemistry: Reaction's, Mechanism, and Stmcture, pp. 349-50 & 372-74 (3d ed.), 1985. By means of illustration, and not limitation, the peptide is conjugated to another via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561).

It is shown herein that the stable protein of the invention oligomerises. It is further shown herein that a fusion protein which comprises the stable protein of the invention and an additional protein similarly oligomerizes. This feature can serve several purposes including increasing the binding avidity of a binding molecule, and generating heterocomplexes which can serve different functions.

Hence, according to another aspect of the present invention there is provided a method of increasing a binding avidity of a binding molecule. The method according to this aspect of the invention comprises displaying multiple copies of the binding molecule on a surface of an oligomer of a denaturant stable and/or protease resistant protein, the denaturant stable and/or protease resistant protein having a chaperone-like activity. The binding molecule, can be, for example, a receptor, a ligand, an enzyme, a substrate, an inhibitor, an antibody and an antigen. In cases where the binding molecule is a binding protein, the binding protein can be fused to the oligomer units via either genetic engeneering techniques or chemical cross linking. In cases where the binding molecule is not a protein, the binding molecule can be fused or linked to the oligomer units via chemical cross linking techniques.

It is shown herein that by either autoclaving and/or treating with a protease one can increase the specific activity of the proteins of the present invention.

Hence, according to another aspect of the present invention there are provided methods of increasing a specific activity of a pre-isolated denaturant stable and/or protease resistant protein having chaperone-like activity as determined in Units of protecting activity per mg protein, one method comprises autoclaving said pre-isolated denaturant stable and/or protease resistant protein; whereas the other method comprises treating said pre-isolated denaturant stable and/or protease resistant protein with a protease.

Thus, the present invention provides an isolated denaturant stable and/or protease resistant protein having chaperone-like activity having an HRP protection activity, as determined using an HRP protection assay, of at lest 10, preferably, at least 50, more preferably, at least 100, more preferably, at least 200, more preferably, at least 500, more preferably, at least 1000, more preferably, at least 1500, more preferably, at least 2000, more preferably, at least 2500, more preferably, at least 3000, more preferably, at least 3500, more preferably, at least 4000, more preferably, at least 4500, more preferably, at least 5000, more preferably, at least 5500, more preferably, at least 6000, more preferably, at least 8000, more preferably, at least 10000, more preferably, at least 15000 Units/mg protein, wherein said HRP protection assay comprises mixing the isolated denaturant stable and/or protease resistant protein having chaperone-like activity at different final protein concentrations at a predetermined volume with 100 µl of 5 nM HRP present in 40 mM HEPES buffer at pH 7.5, thus forming a first reaction mixture, and following incubation of said reaction mixture at 25° C. for 16 hours, determining HRP remaining enzymatic activity by mixing 5 µl of said first reaction mixture with 100 µl of TMB (3 3'5 5'-tetramethylbenzidiine), thus forming a second reaction mixture, incubating said second reaction mixture for 10 minutes, stopping a reaction of said second reaction mixture by an addition of 100 µl of 1 M sulfuric acid and recording calorimetric change in said second reaction mixture at 435 nm, whereby said units are defined as a dilution factor of said denaturant stable and/or protease resistant protein having chaperone-like activity at a concentration of 1 mg/ml that confers 50% protection of HRP activity in said HRP protection assay.

The present invention also provides a hetero complex which comprises an oligomer including a plurality of a denaturant stable and/or protease resistant protein, the denaturant stable and/or protease resistant protein having a chaperone-like activity, and at least two different molecules which are fused to the oligomer. The at least two different molecules may comprise at least a first enzyme and a second enzyme. The first enzyme and the second enzyme may catalyze sequential reactions in a synthesis or degradation pathway. The first enzyme and the second enzyme may catalyze different reactions in a synthesis or degradation pathway. In another embodiment, the at least two different molecules comprise at least a binding molecule and a reporter molecule, such as GFP or HRP.

In cases where the molecules are proteins, the proteins can be fused to the oligomer units via either genetic engeneering techniques or chemical cross linking. In cases where the molecules are not proteins, the molecules can be fused or linked to the oligomer units via chemical cross linking techniques.

One of the uses of such fusion proteins emerges from the fact that the stable proteins of the present invention retain their activity and oligomerability also when in context of a fusion protein. Interestingly, under such conditions, the counterpart fused to the stable protein of the present invention also retains its activity, as is demonstrated in the Examples section that follows by the fusion CBD-SP1. As such, an oligomerized fusion protein of the invention can serve to better present the counterpart fused to the stable protein of the present invention for immunization or surface reactions.

Thus, according to yet an additional aspect of the present invention there is provided a method of immunization comprising subjecting an immune system of a mammal to the fusion protein described herein.

It was uncovered that immunization with an SP1-polypeptide fusion protein reduces the immune response to the polypeptide. Hence, according to yet another aspect of the invention, there is provided a method of administering to an animal having an immune system a polypeptide, while reducing an immune response against the polypeptide. The method according to this aspect of the invention is effected by administering the polypeptide to the animal, the polypeptide being fused to a denaturant stable and/or protease resistant protein, the denaturant stable and/or protease resistant protein having a chaperone-like activity, thereby reducing the immune response against said polypeptide, as compared to an immune response that develops by administering to the animal the polypeptide alone.

In an in vitro assay it was shown that SP1 induces faster coverage of scraped regions of fibroblast cells in a petri dish.

Hence, according to another aspect of the present invention, there is provided a method of increasing cell migration. The method according to this aspect of the invention is effected by exposing the cells to an amount of a denaturant stable and/or protease resistant protein, the denaturant stable and/or protease resistant protein having a chaperone-like activity, sufficient for increasing cell migration.

As cell migration is essential for wound healing, there is also provided according to the present invention a method of accelerating wound healing effected by administering onto a wound an amount of a denaturant stable and/or protease resistant protein, the denaturant stable and/or protease resistant protein having a chaperone-like activity, sufficient for accelerating wound healing. There is also further provided according to the present invention a method of inducing wound healing effected administering onto a wound an amount of a denaturant stable and/or protease resistant protein, the denaturant stable and/or protease resistant protein having a chaperone-like activity, sufficient for inducing wound healing.

It is shown in the Examples section below that hair is strengthenes via administration of SP1.

Hence, according to another aspect of the present invention there is provided a method of strengthening and/or grooming hair, nail or skin. The method is effected by administering onto the hair, nail or skin an amount of a denaturant stable and/or protease resistant protein, the denaturant stable and/or protease resistant protein having a chaperone-like activity, sufficient for strengthening and/or grooming the hair, nail or skin.

The polypeptides of the present invention can be formulated into pharmaceutical (including cosmetical and cosmoceutical) compositions that comprise, as an active ingredient, a denaturant stable and/or protease resistant protein, the denaturant stable and/or protease resistant protein having a chaperone-like activity, and a pharmaceutically acceptable carrier, approved for use in humans or for veterinary use by an appropriate regulatory agency such as the Food and Drug Administration in the United States of America. For use in wound healing, the pharmaceutical composition is packaged in a package and identified in print for use in a wound healing application. For use in strengthening/grooming hair, nail or skin, the pharmaceutical composition is packaged in a package and identified in print for use in a strengthening and/or grooming hair, nail or skin application. Additional ingredients can be used in such compositions. For example, the stable protein of the invention can be added to hair, skin or nail grooming compositions such as soaps, shampoos, conditioners, creams, gels, sprays, lacs, etc., the other ingredients thereof are well known in the art and are typically listed on the containers of such products.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Purification of plant-derived boiling-stable proteins: Boiling stable protein fractions of aspen, tomato M82, VF36 and pine were prepared as follows: Crude plant extracts were centrifuged at 10,000 g for 10 minutes and supernatants were transferred to fresh tubes. The supernatants were subjected to a 10-minutes boiling session, then kept on ice for 5 minutes and centrifuged for 10 minutes at 10,000 g. Resulting supernatants were precipitated by adding 4 volumes of cold acetone, and centrifuged for 10 minutes at 10,000 g. Boiling stable proteins were then recovered by dissolving the pellets in 10 mM Tris-HCl buffer (pH 7.5). Total protein concentration was determined as for SP1 preparations (see below).

Only when the total boiling-stable proteins were separated on a 17% SDS-tricine PAGE, a 66 kDa band that appears using the electrophoresis condition described by Pelab (1995) separated as two bands of 66 and 116 kDa. The 66 kDa band was found to represent a germin-like protein.

Purification of plant SP1 protein: Acetone-precipitated boiling-stable proteins of aspen plant prepared as described above were dissolved in 1×tricine-SDS sample buffer (100 mM Tris-HCl, pH 6.8, 20% glycerol, 1% SDS, 0.025% Coomassie blue G-250), then separated on a preparative 17% polyacrylamide tricine-SDS gel. Major bands corresponding to SP1 (116 kDa oligomer and 12.4 kDa monomer) protein were excised from the gel. SP1 oligomer and monomer were electro-eluted separately, in a dialysis bag. The eluent was further dialyzed against 500 volumes of 10 mM Tris-HCl (pH 7.5) overnight at 4° C., followed by acetone precipitation and centrifugation. Purified SP1 was obtained by dissolving the pellet in 10 mM Tris-HCl (pH 7.5). Protein concentration was determined using the BIO-RAD protein assay kit (Hercules, Calif., USA) employing bovine serum albumin as the standard.

Generation of polyclonal antibodies: Gel-purified native SP1 or recombinant CBD-SP1 (50 µg per injection) were injected to rabbits with complete Freuid's adjuvant. Two additional boosts (at 14 days intervals) were injected and 14 days later anti-serum was collected.

cDNA clotting: Polyadenylated (poly A+) RNA extraction was performed according to Bartels and Thompson (1983) from water-stressed aspen shoots, and the mRNA was used as a template for cDNA synthesis. A lambda ZAPII (Stratagene, La Jolla, Calif., USA) cDNA library was constructed according to the supplier's instructions, and immunoscreened with SP1 polyclonal antibodies raised against the natural protein as described above (diluted 1:500, v/v). In vivo excision was performed according to the supplier's instructions and the sequence was determined (Sequencing Lab, The Weizmann Institute of Science, Rehovot, Israel).

Generation of a CBD-SP1 fusion protein in *E. coli:* SP 1 cDNA was cloned into pET-CBD-180 (Shpigel et al., 1999) expression vector by subcloning therein a PCR product generated using two amplification primers carrying an NcoI site (forward primer) 5'-AAAACCATGGCAACCA-GAACTCCAAAGC-3' (SEQ ID NO:3) and a BamHI site (reverse primer) 5'-AAAAGGATCCTTACTTTATTAC-CATGAAATAGCC-3' (SEQ ID NO:4) for amplification of the corresponding ORF of SP1 cDNA. The resulting plasmid (pET-CBD-180-SP1) was used to transform *E. coli* strain BL21 (DE3). Recombinant CBD-SP1 fusion protein synthesis was induced in BL21 (DE3) by the addition of IPTG (isopropyl-D-thiogalactoside) to a final concentration of 1 mM to mid-log phase of the bacterial culture, followed by five additional hours induction at 37° C. Recombinant CBD-SP1 protein was purified on cellulose according to Shpigel et al. (1999). The recombinant CBD-SP1 fusion protein was detected using SDS-PAGE.

Generation and Secretion of Recombinant SP1 by *Pichia pastoris:*

A DNA fragment of SP1 protein coding region was cloned in-frame at the EcoRI and NotI restriction sites of the secretory *Pichia pastoris* expression vector pPIC9K (Invitrogen®, Groningen, The Netherlands) to generate pPIC9K-SP1. The construct sequence was confirmed by sequencing (Sequence lab, Weizmann Institute, Rehovot, Israel). In order to transform *Pichia pastoris* cells, pPIC9K-SP1 was linearized by SalI or BglII restriction enzymes. The linearized constructs were each independently used to transform *Pichia* competent cells by electroporation, according to supplier's instruction (Invitrogen®, Groningen, The Netherlands). To this end, 5-10 µg of SalI or BglII linear pPIC9K-SP1 DNA were used to transform *Pichia* SMD1168, a protease deficient mutant, His⁺, Mut⁺ (Methanol utilization plus) phenotype stain. Transformed competent cells were plated onto RDB plates and incubated at 30° C. Five days later, 240 colonies from SalI (Mut⁺) and 180 colonies from BglII (Mut$^s$: Methanol utilization slow) transformants were first transferred to YPD plates containing 0.25 mg/ml G418 antibiotics; 73% and 16% of Mut⁺ and Mut$^s$ transformants survived. For Mut⁺ transformants, surviving colonies were further transferred to YPD plates containing a higher concentration of G418. Mut$^s$ transformants were transferred to MM plates. To select the high expression level transformants, 2 Mut⁺ transformants from 4 mg per ml and 2 from 1 mg per ml G418, respectively and 4 Mut$^s$ colonies were used in a small volume expression system according to the manual for expression of recombinant proteins in *Pichia pastoris* (Invitrogen®). The screening of high-copy-number transformants and expression of recombinant SP1 were performed according to the instructions in the manual of *Pichia Pastoris* (Invitrogen®). The secreted recombinant SP1 was detected from the culture medium by SDS-PAGE. The gels were either stained with Coomassie blue for total protein visualization, or blotted onto nitrocellulose (Western blots) for immunodetection of SP1 with polyclonal anti-SP1.

Gel filtration, HPLC and native SP1 detection: An HPLC system (Merck, Hitachi) equipped with a TSKSWX3000 (30 cm×7.8 mm) column (SUPELCO, Sigma, Israel) was employed to study the size of SP1 in its native state. A 100 µl aliquot of total soluble proteins extract from water-stressed aspen plants, or the total boiling-stable fraction of the same extract was separated using PBS buffer at pH 6.6. The flow rate was adjusted to 0.8 ml per minute and a UV monitor was used at 280 nm to detect elution of proteins from the column. Fractions were collected every minute. Each fraction was further concentrated by adding four volumes of cold acetone, followed by 10 minutes centrifugation at 10,000 g. The resulting pellets were dissolved in 1×SDS-sample buffer. An aliquot was separated on 17% tricine-SDS-PAGE, and the resultant protein profiles were either visualized by Coomassie staining or Western blot analysis using anti-recombinant SP1 antibodies (see above). Purified native SP1 and recombinant CBD-SP1 (50 µl aliquots) at a concentration of 1 milligram per milliliter and 0.5 milligram per milliliter were also analyzed. To determine the size of the protein, cytochrome C (12.4 kDa), carbonic anhydrase (29 kDa), bovine serum albumin (66 kDa), alcohol dehydrogenase (150 kDa), beta-amylose (200 kDa) and apoferritin (443 kDa) (Sigma-Aldrich Israel Ltd.) were used as molecular standards. Blue dextran (2000 kDa) was used to evaluate the void volume of the column. A linear relationship was obtained by plotting the logarithms of the molecular weights of standard proteins against their respective elution parameters (Kav) The Kav value was calculated using the equation: $Kav=(Ve-Vo)/(Vt-Vo)$, where Ve=elution volume of the protein, Vo=column void volume, Vt=total packed bed volume.

SP1 stability following exposure to SDS and heating: For evaluating the stability of SP1 complexes to detergents, equal amounts of purified SP1 protein were prepared in a sample buffer containing SDS at a final concentration ranging from 0% (native sample buffer) to 2% (conventional Laemmli sample buffer), and corresponding to a final molar ratio of 1:0, 1:200, 1:400, 1:500, 1:600 or 1:4334 (SP1 monomer:SDS). The samples were boiled (or not boiled) for 5 minutes prior to separation on a 17% tricine-SDS-gel. To examine the stability of SP1 oligomer to heating, SP1 was prepared in SDS sample buffer at a final molar ratio of 1:900 (SP1 monomer:SDS) and was heated for 5, 10 or 20 minutes at a range of temperatures from room temperature to 100° C. before separation on SDS-tricine PAGE.

In vitro assay of thermal stabilization by SP1: The heat-protective activity of SP1 was examined in vitro by measuring the effect of SP1 on the thermal stability of Citrate Synthase (CS) and Horseradish Peroxidase (HRP) enzymatic activity.

Protein preparation: CS (Roche Diagnostics GmbH, Mannheim, Germany) was prepared according to the method of Buchner et al. (1998). HRP, BSA, lysozyme (SIGMA, Israel) and CBD (CBD-Technologies Ltd. Rehovot, Israel) were dissolved in water to about 10 mg/ml, then dialyzed overnight against 200 volumes of 40 mM HEPES-KOH buffer (pH 7.5) at 4° C. After dialysis, proteins were centrifuged at 13,000 rpm for 15 minutes at 2° C. to remove any insoluble particles. 20 µM HRP, 60 µM of BSA and lysozyme stock solution was prepared in filtered HEPES buffer and aliquoted. Aliquots were stored at −20° C. Thawed aliquots of proteins were discarded after use. The protein concentration was determined as for SP1. Lyophilized alpha-crystallin (Stressgen Inc., Canada) was resuspended in water according to supplier's instruction.

CS and HRP activity assay: Enzyme activity assays were performed at 25° C., in an ELISA plate. The colorimetric reaction was recorded by a microplate reader (BIO-RAD,) at 412 nm for CS, and 650 nm for HRP.

CS activity assay was according to the method of Buchner et al. (1998) with a slight modification: the volume of the reaction components was proportionally reduced for the ELISA plate volume. Briefly, 4 μl of 0.15 μM CS was mixed with 200 μl of reaction mixture composed of TE buffer (50 mM Tris, 2 mM EDTA, pH 8.0), 100 μM oxaloacetic acid (in 50 mM Tris, pH not adjusted), 100 μM DTNB (in TE buffer), and 150 μM acetyl-CoA (in TE buffer). The change in absorbency was recorded in 20-second intervals for 1 minutes. The linear portion of the plot was used to calculate the specific activity of the CS. CS activity was expressed as μmol per minute per mg (defined herein as activity unit) using a molar extinction coefficient of DTNB of $1.36 \times 10^{-4}$ M per cm.

Sensitive one-step TM Slow TMB-ELISA: TMB (3,3',5,5'-tetramethylbenzidine; PIERCE, Rockford, USA) was used as substrate for HRP activity assay in the experiments. An optimal colorimetric reaction of HRP was determined experimentally. The linear portion of the graph representing absorbency vs. time was used to calculate the rate of change in absorbency at 650 nm. Optimal reaction conditions were determined to be 4 μl of 2.5 nM HRP in 100 μl of TMB substrate at 25° C. The reaction was recorded at 30-second intervals for 5 minutes. HRP activity was expressed as μmol per minute per mg (defined herein as enzyme activity unit) by using a molar absorption coefficient for blue charge-complex of $3.9 \times 10^{-4}$ M per cm (Josephy et al., 1982).

Heat inactivation of CS and HRP: A 100 μl aliquot of 0.15 μM CS or 2.5 nM of HRP prepared in pre-chilled 40 mM HEPES buffer, pH 7.5, was heated in the absence or presence of proteins (SP1, CBD-SP1, BSA, lysozyme, and other plant boiling stable proteins (see above)) using a programming T-gradient thermocycler (Biometra, Gottingen, Germany) for desired temperature and length of time. Aliquots were removed for enzyme activity assay during the course of the heat challenge.

The degree of protection conferred by the specific protein at each time point was expressed as % remaining activity of the full enzyme activity. Each point represents at least 4 replicates. Data were analyzed by JMP (version 3.11) program.

Stability of recombinant SP1 from *Pichia pastoris:* Culture medium containing secreted recombinant SP1 was boiled for 10 minutes, followed by 10 minutes centrifugation at 10,000 g. Supernatant samples were prepared in either full strength SDS (2%) sample buffer or native sample buffer (0% SDS). Samples were boiled in sample buffers for 5 minutes before separation on 17% tricine-SDS-PAGE.

Transmission electron microscopy (TEM) study: Purified native SP1 at a concentration of 0.45 mg per ml was applied to carbon grids and stained with uranyl acetate. The images were visualized in a Philips CM12 EM and recorded on a Tietz CCD camera (Dr. Sharon Wolf, Electron Microscope Center, Weizmann Institute of Science, Rehovot, Israel).

Additional experimental procedures: Additional methods and procedures are described in detail under the brief description of the drawings in context of specific Figures.

Experimental Results

Figure 1:
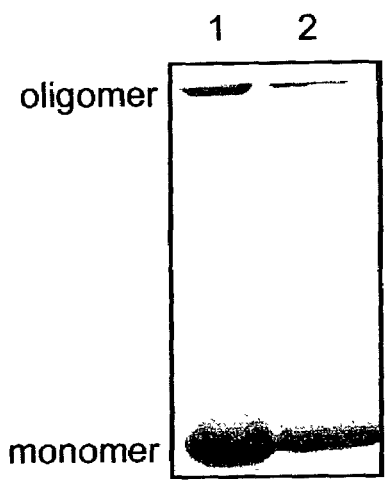
FIG. 1 demonstrates the separation on SDS-tricine PAGE of the purified 12.4 kDa SP1 monomer and the 116 kDa oligomer fractions. 12.4 and 116 kDa fractions of SP1 proteins were excised from corresponding bands in 17% SDS-tricine-PAGE of boiling-stable aspen extracts. The proteins were then electro-eluted. Samples of the electro-eluted proteins were prepared in 2×SDS sample buffer, boiled for 5 minutes and loaded on a 17% polyacrylamide SDS-tricine gel. Lane 1: 12.4 kDa SP1 fraction. Lane 2: 116 kDa SP1 fraction.

Stability of native SP1 oligomer to heat- and detergent denaturation: SP1 from aspen plants was first identified as a large size protein on SDS-PAGE, appearing as a complex in the total soluble proteins extract. When partially denatured, a large (116 kDa) and small molecular size (12.4 kDa) form of the protein are detected (FIG. 1). These two forms represent the monomeric (12.4 kDa) and native homo-oligomeric (116 kDa) states of the SP1 protein, as demonstrated by the interconversion of gel-purified samples of the two forms under extreme denaturing conditions (FIG. 1).

Figure 2A:
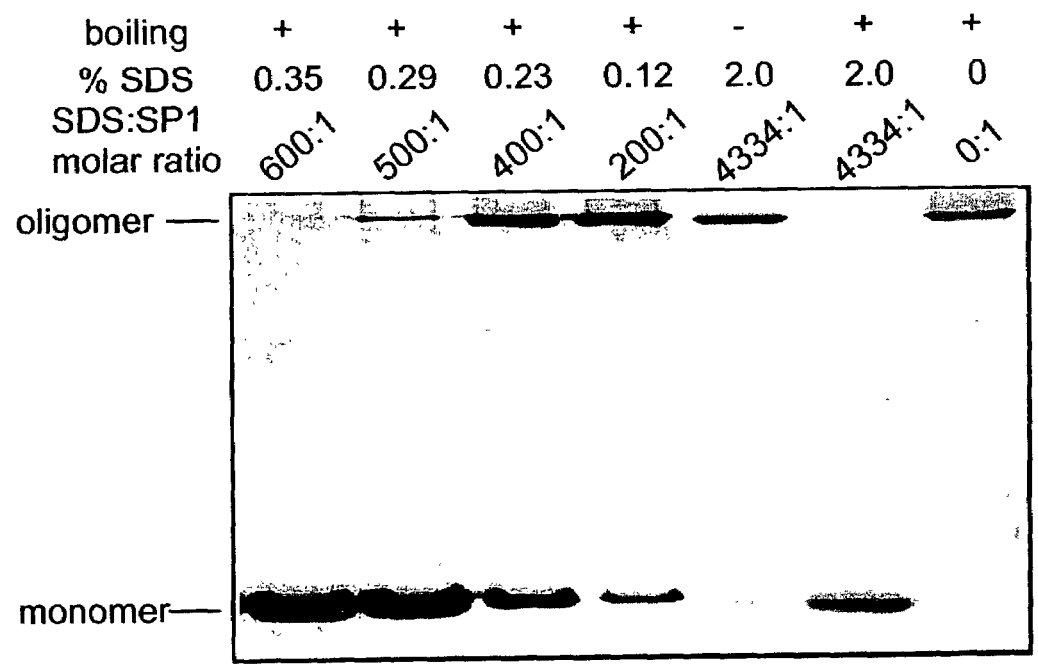
FIGS. 2a-c demonstrate the stability of the SP1 oligomer to SDS- and heat treatment.

The remarkable resistance of the native SP1 oligomer to denaturation by detergent was examined throughout a range of SDS concentrations. Despite the presence of SDS in the gel and the running buffer (0.1%), it was found that only a small amount of monomer could be observed when SP1 was prepared in native (0%) sample buffer (FIG. 2a). The SP1 complex remained stable when boiled in SDS concentrations up to 600:1 (SDS:SP1 monomer) molar ratio, and at even at much higher SDS concentrations without boiling (FIG. 2a).

Figure 2B:
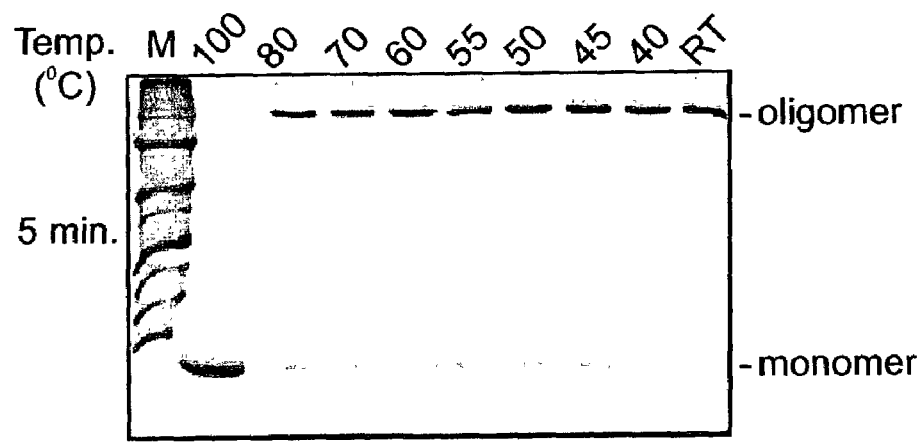
Figure 2C:
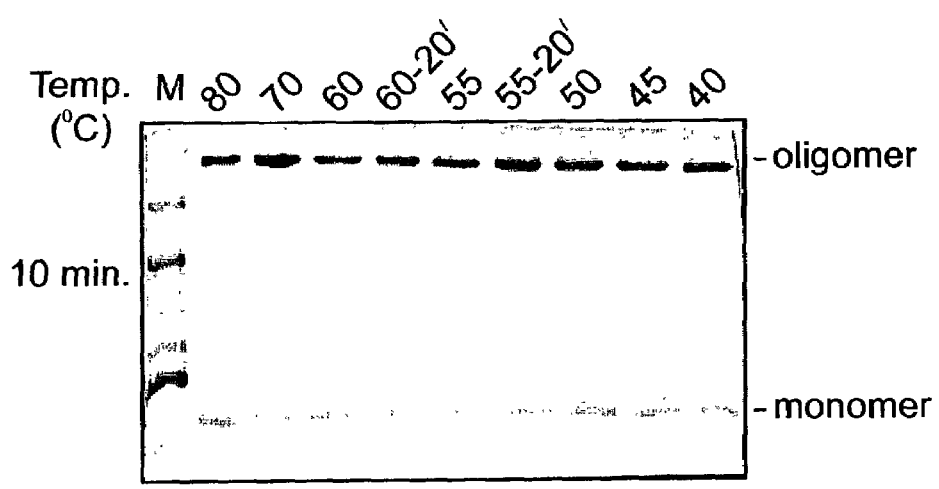

Thus, the SP1 oligomer also exhibits unusual thermal stability. This was further demonstrated by the consistent stability of the oligomeric form of SP1 at temperatures up to 80° C. and 900:1 SDS: SP1 monomer concentration (FIG. 2b), regardless of the length of incubation (FIG. 2c).

Protease resistance and detergent-free purification of SP1: The detergent-free purification and protease resistance of SP1 from aspen plant was demonstrated by cryogenic extraction (at −50° C.) followed by 60 minutes protease K treatment of the soluble protein fraction from aspen shoots or leaves at 37° C. Upon termination of proteolytic digestion, the predominant protein in the remaining soluble fraction was SP1. Size fractionation by molecular filtration demonstrated that the protease-resistant SP1 was greater than 50 kDa molecular mass, indicating that the resistant protein maintained oligomeric structure.

Figure 3A:
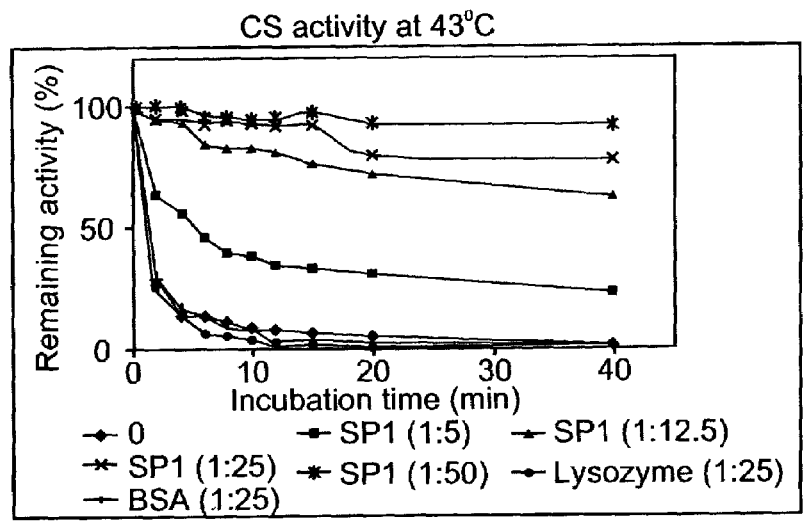
FIGS. 3a-c demonstrate the protection of Citrate Synthase (CS) from heat inactivation by addition of native or recombinant SP1. Enzymatic activity of CS at 43° C. was assayed at successive intervals (as described in the Examples section that follows).
Figure 3B:
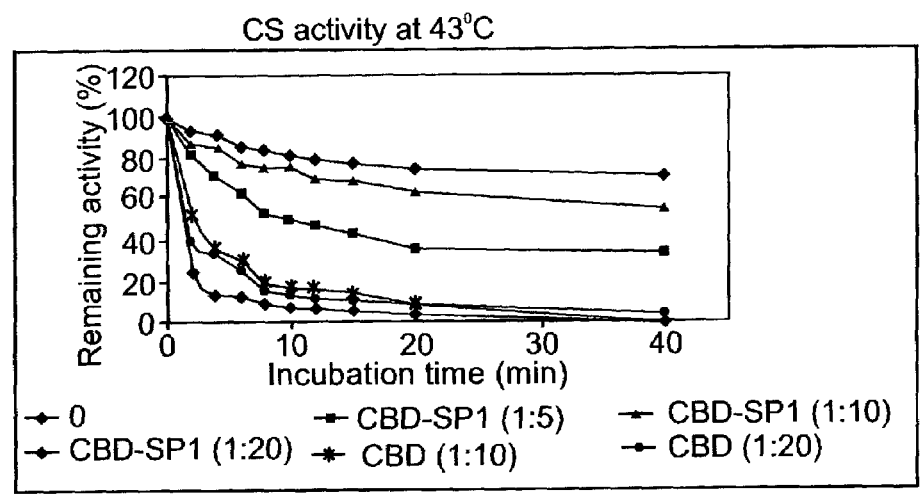
Figure 3C:
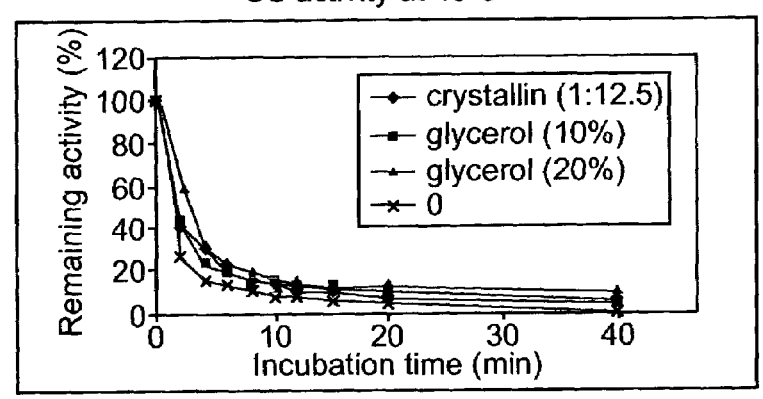

SP1 increases the thermal stability of Citrate Synthase (CS) and Horseradish Peroxidase (HRP) enzymatic activity: The chaperone-like activity of SP1 was assessed in vitro by measuring the resistance of CS and HRP enzymatic activity to heat-denaturation in the presence of SP1. CS is a commercially available, heat-labile dimeric enzyme, undergoing inactivation after 15 minutes at 43° C. in the absence of any protectant (FIG. 3a). In the presence of high concentrations of SP1 (CS:SP1 ratio of 1:50), CS activity remained nearly 100% for 15 minutes and retained at least 93% of its activity for the duration of the assay (40 minutes). Lower concentrations of SP1 conferred proportionally less protection against heat inactivation (at a CS:SP1 ratio of 1:5, 22% protection was achieved at 40 minutes). In contrast to the dramatic protection afforded by SP1, neither BSA nor lysozyme affected heat inactivation of CS activity (FIG. 3a). In a separate assay, the protein stabilizers glycerol (10 and 20%) and the Hsp alpha-crystallin were equally ineffective in protecting CS enzyme activity from thermal inactivation (FIG. 3c).

HRP is a commercially available monomeric protein with a molecular mass of 44 kDa. When incubated at 55° C. under standard assay conditions (see Materials and Methods), 60% of the enzyme activity was lost after 10 minutes and more than 90% was lost after 60 minutes. Only 3% of original HRP activity could be measured after 2 hours at 55° C. (FIG. 4). No recovery of activity was observed following exhaustive (16 hours) incubation of the heat-inactivated enzyme at 25° C. Thus, HRP activity is heat-labile at 55° C. When native purified SP1 was added, protection of HRP activity from heat-inactivation was significant at HRP:SP1 molar ratios of 1:50 and above. At a HRP:SP1 molar ratio of 1:300, greater than 60% protection was achieved at 60 minutes, with 53% activity remaining after 2 hours incubation at 55° C. SP1 mediated protection from heat-inactivation of HRP was significant, but proportionally weaker at ratios of 200:1, 100:1 and 50:1 (FIG. 4). At a 1:25 HRP to SP1 molar ratio, little protection was observed. BSA addition (HRP:SP1 ratio of 1:300) also afforded a degree of protection, but SP1 was approximately 3-fold more effective (FIG. 4).

Cloning and sequence analysis of SP1 cDNA: A lambda expression library was prepared from polyadenylated RNA of water-stressed aspen shoots, as described in Materials and Experimental Methods above. After screening $7\times10^5$ recombinant phage plaques with polyclonal anti-SP1 antibodies, a 567 nucleotide cDNA sequence encoding a SP1 polypeptide (SP1 cDNA) was isolated (FIG. 5 and SEQ ID NO:1 and SEQ ID NO:2 for the nucleotide and amino acid sequences of SP1, respectively). Nucleotide sequence analysis of the cDNA (Wisconsin Package Version 9.1, Genetics Computer Group-GCG, Madison Wis.) indicated that the SP1 cDNA encodes a 12.368 kDa polypeptide with a calculated p1 of 4.87. Analysis of the open reading frame revealed that this polypeptide lacks Cystein residues, is low in Tryptophan residues (0.9%), and is rich in Leucine (13.8%), Threonine (9.2%), Alanine (8.3%), Glutamic (7.4%) and Serine (7.4%) residues. No homology was detected with any known protein sequences in the SWISS-PROT protein bank. Coding sequences exhibiting sequence homology with SP1 from various evolutionary distant plant species were identified using the EST database (Plurality=10.0; Threshold=4; Average Weight=1.00; Average Match=2.91; Average Mismatch=−2.00). 25 sequences with significant homology (E value below 0.5) were identified (3 in *Arabidopsis*, 2 in maize, 1 in potato, 2 in rice, 1 in sorghum, 7 in soybean, 2 in tomato and 7 in wheat, see FIG. 12 and SEQ ID NOs:7-32, Consensus Sequence—SEQ ID NO:33). The putative peptide sequences were aligned and compared with the peptide sequence of SP1 (SEQ ID NO:2), revealing a few conserved consensus sequences: "HAFESTFES" (61-75, SEQ ID NO:36), "VKH" (9-11, SEQ ID NO:37) and "KSF" (47-49, SEQ ID NO:38) for example, indicating that SP1 is a member of a family of protein genes with wide representation in both dicot and monocot plant genomes. However so far, no function has been discovered or ascribed for any of the proteins in this family, except as reported herein.

In addition to the above sequences, high DNA homology with SP1 cDNA (SEQ ID NO:1) was noted for a number of ESTs from Populus: 97% homology with ESTs AI161912 (SEQ ID NO:5) and AI163063 (SEQ ID NO:6), 90% homology with AI161643 (SEQ ID NO:39) and 92% homology with AI163329 (SEQ ID NO:40) of a hybrid aspen (*Populus tremula*×Populus tremuloides); 96.6% homology with *Populus trichocarpa*×*Populus deltoides* pop3 mRNA sequence (SEQ ID NOs:34 and 35 for nucleic acid and amino acid sequences, respectively, see also FIG. 13, for homology alignment of the protein encoded by the pop 3 mRNA—SEQ ID NO:35, and the SP1 protein—SEQ ID NO:2), 61.6% homology with *Populis trichocarpa*×*Populus deltoides* wound responsive mRNA (EMBL Acession Numbers M18538 and X55440, respectively). The SP1 protein was identified in all of the Populus species studied. The SP1 cDNA nucleotide sequence was submitted to EMBL (under Accession Number AJ276517). Analysis of the polypeptide encoded by SP1 using Kyte and Doolittle (1984) and Goldman et al. (1986) hydropathy plots indicated that SP1 is a highly hydrophilic protein, except for it's hydrophobic C-terminus.

Figures 6A, 6B:
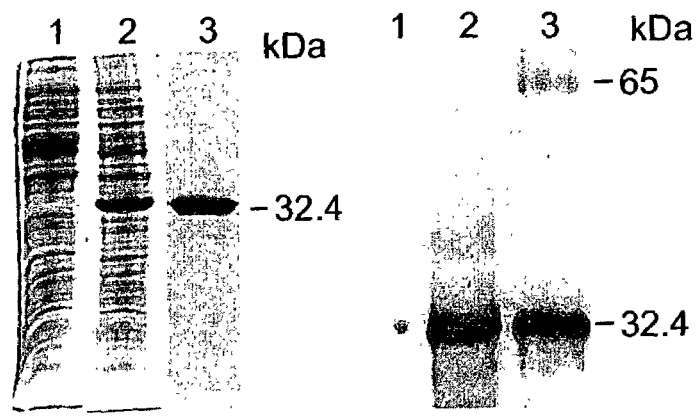
FIGS. 6a-b demonstrate the PAGE analysis and immunodetection of recombinant CBD-SP1 fusion protein (32.4 kDa) from transformed E. Coli cells. Proteins were separated on 15% trince-SDS-polyacrylamide mini-gels. Lane 1: Total bacterial proteins (E. coli containing no cDNA insert). Lane 2: Total transformed bacterial proteins (E. coli containing cbd-SP1 insert). Lane 3: Cellulose- purified CBD-SP1 fusion protein.
Figure 7:
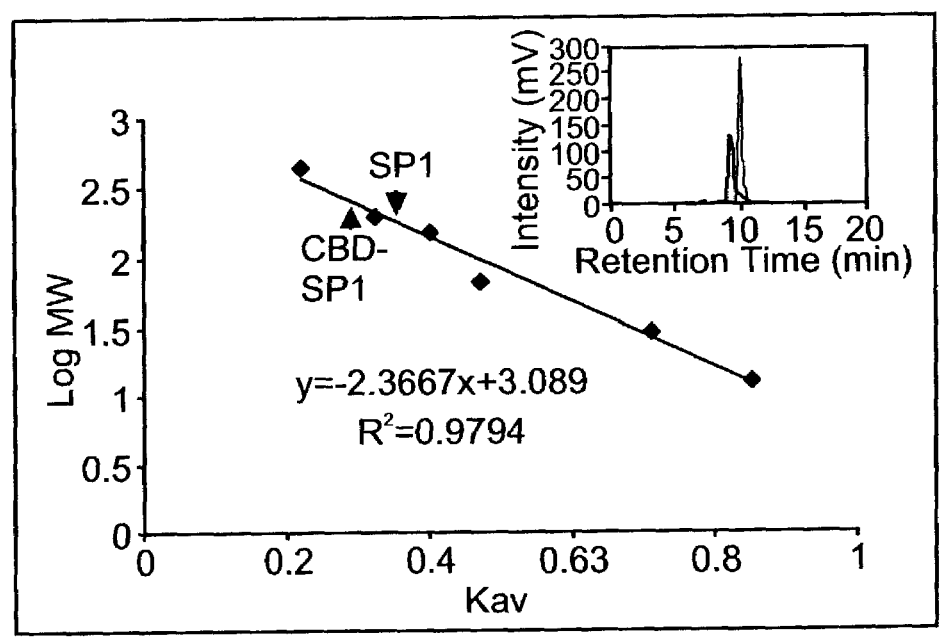
FIG. 7 demonstrates the gel filtration HPLC molecular weight analysis of native SP1 and recombinant CBD-SP1. Purified SP1 and CBD-SP1 eluted from the TSK-3000 column as single peaks with retention times of 9.8 (Kav=0.36025) and 9.2 (Kav=0.2775) minutes respectively. The calibration curve was obtained by plotting the logarithms of the molecular weights of standard proteins (see Materials and Methods) against their respective elution parameters (Kav). $R^2$ volume was calculated by the method of least square and is shown in the figure.

SP1 expression in *E. coli,* purification of recombinant CBD-SP1 fusion protein, and the antigenic character of recombinant CBD-SP1 protein: Introduction of the cloned SP1 cDNA sequence into the pET-CBD-180 CBD expression vector (FIG. 11, as described in Materials and Experimental Methods) resulted in a nucleotide sequence which encoded a CBD-SP1 fusion protein. Recombinant CBD-SP1 was expressed at high levels by the bacteria (approximately 300 milligrams per liter culture medium) and accumulated as inclusion bodies. When total *E. coli* extract was separated on SDS-PAGE, a 32.4 kDa band was detected by Coomassie blue staining, apparently absent from the un-transformed bacterial protein fraction (FIG. 6a). The antigenic identity of the fused protein with SP1 was demonstrated by a strong reaction upon immunodetection of the 32.4 kDa fused monomeric protein band on Western blots of the same gels, using the polyclonal anti-SP1 antibodies (FIG. 6b). An immunoreactive 65 kDa band was also detected on the SDS-PAGE of total transformed bacterial protein, possibly representing a dimer of the 32.4 kDa fusion protein (FIG. 6b). Recombinant CBD-SP1 fusion protein was purified on cellulose beads from 4.5 M urea-solubilized inclusion bodies, taking advantage of the affinity of CBD to cellulose beads. The highly purified CBD-SP1 fusion protein obtained was used to prepare polyclonal anti-CBD-SP1 antibodies in rabbits. These polyclonal anti-CBD-SP1 antibodies also recognized 32.4 kDa and 65 kDa CBD-SP1 protein bands on Western blots of transformed cell extracts, further confirming the antigenic identity of the recombinant CBD-SP1 and native SP1 polypeptides. The molecular weights of purified native SP1 protein and recombinant CBD-SP1 protein under non-denaturing conditions (PBS buffer) were estimated by gel-filtration HPLC and immunodetection of the eluted protein fractions on Western blots with anti-SP1 and anti-CBD-SP1 antibodies. Both the native SP1 and the recombinant CBD-SP1 proteins eluted as single peaks, at about 9.8 and 9.2 minutes, respectively (FIG. 7). These peaks corresponded to molecular weights of 172.5±1.25 kDa and 267.5±2.5 kDa, representing a complex of 14 units (13.9) of SP1 monomer (12.369 kDa) and 8.4 units of CBD-SP1 monomer (32.4 kDa), respectively. Naturally, the number of subunits can only be estimated since the results are influenced by the shape of the complex.

Cloning of SP1 DNA it *Pichia pastoris* and secretion of recombinant SP1 protein: Recombinant, non-fused SP1 secretory protein was generated by transforming Pichia SMD1168 (a protease deficient mutant, His+, Mut+) cells with SP1 DNA from SalI- or BglII linearized pPIC9K plasmids as described in Materials and Methods. High levels of SP1-expression were induced and maintained in the transformed cells by the addition of methanol to the culture for 96 hours. One Mut$^+$ and one Mut$^s$ transformant were found to express and secrete relatively high levels of recombinant SP1, absent from the control cell culture media, as verified by SDS-PAGE (FIG. 8) and immunodetection on Western blot with anti-SP1 antibody.

SDS- and Heat-stable properties of recombinant SP1 protein: Recombinant SP1 protein from the culture medium of transformed cells was exposed to extremes of heat and SDS concentrations in order to determine the functional similarity of the recombinant and native polypeptide (FIG. 8). Separation of heat- and SDS-treated culture medium on SDS-PAGE demonstrates that, as with native SP1, the recombinant SP1 oligomer is boiling resistant, dissociating to the monomeric form only in the presence of high concentrations (2%) of SDS (FIG. 8).

Recombinant CBD-SP1 fusion protein increases the thermal stability of CS: The ability of recombinant CBD-SP1 fusion protein to protect against thermal inactivation of citrate synthase enzymatic activity was demonstrated employing the CS colorimetric assay (as described in Materials and Methods). Like the native SP1 protein, purified recombinant CBD-SP1 conferred significant, concentration-dependent protection against thermal inactivation of CS enzymatic activity at 43° C. (FIG. 3*b*). After 40 minutes, 73% activity remained at CS:CBD-SP1 monomeric molar ratio of 1:20. At a ratio of 1:5, 33% of the enzymatic activity was retained, compared to the controls. In contrast to this, incubation with high concentrations of non-fused CBD protein (FIG. 3*b*), BSA or lysozyme protein (FIG. 3*a*) had no protective effect on the inactivation of CS. Incubation with other protein stabilizers, such as glycerol (10 or 20%) or the Hsp alpha-crystallin (1:12.5 CS:alpha-crystallin ratio) was also without effect on CS inactivation (FIG. 3*c*). Thus, the portion of the SP1 protein encoded by the cloned sequence retains the thermally protective properties of the native protein.

Boiling-stable proteins from plants protect against thermal inactivation of CS enzyme activity: The existence of SP1-like proteins in other plant species was investigated by assaying the effect of boiling-stable protein fractions from tomato and pine (which are evolutionary distant plants) on heat-inactivation of CS enzymatic activity. Total boiling-stable proteins from tomato M82, tomato VF36 and pine plants were prepared (as described under Materials and Methods), and compared with crude Aspen boiling-stable protein fractions for their thermal stabilizing effect on CS enzymatic activity at 43° C. Significant protection against thermal inactivation (greater than 60% activity remaining after 40 minutes) was demonstrated by the tomato and pine boiling-stable fractions (FIG. 9).

Immune cross reactivity, stress responsiveness and oligomeric structure of SPs from Pine and Tomato: Antigenic cross reactivity of stable proteins from phylogenetically remote species was investigated by Western blotting and immune detection with anti-SP1 antibodies. Total boiling stable proteins from salt- and drought stressed tomato leaves, and temperature- and drought stressed pine material was prepared (as described under Material and Experimental Methods above), separated on SDS PAGE, blotted onto nitrocellulose and immune reacted with either anti-native oligomeric SP1 antibodies or anti recombinant SP1 antibodies (anti-CBD-SP1). Cross reactive proteins were detected in blots of both tomato (FIGS. 14*c* and 14*d*) and pine extracts (FIGS. 14*a* and 14*b*), with a predominant, stress-responsive band at 45-50 kDa. Simmilar cross rectivity was observed also for rice and corn boiling stable protein extracts.

Characterization of native SP1 molecular structure by Electron Microscopy: The molecular structure of native SP1 was examined using Transmission Electron Microscope (Materials and Methods). These TEM studies of purified SP1 protein indicated a ring-like protein with a central cavity. The entire structure diameter is approximately 11 nanometers (FIG. 10).

Protectioin of α-Amylase by SP1: In addition to HRP and CS protection by SP1, it is shown herein that SP1 can be used to protect α-amylase from inactivation induced by both high $CaCl_2$ concentrations (known as salt denaturation) and upon incubation for extended time periods at room temperature. As shown in FIG. 15, $CaCl_2$ at high concentration inactivates α-amylase; after 2 hours incubation at 1 M and 2 M $CaCl_2$ α-amylase activity was dropped to less than 60% and to less than 10%, respectively. SP1 treated enzyme was fully protected in the presence of 1 M $CaCl_2$ and 50% protected in the presence of 2 M $CaCl_2$. Long incubation of diluted α-amylase solution at room temperature also caused a dramatic loss of enzyme activity. As shown in FIG. 16, only about 25% activity remained after one-week incubation at room temperature. However in the presence of SP1, more than 40% activity remained following one-week incubation at room temperature. Thus, SP1 protects α-amylase from inactivation induced by both high $CaCl_2$ and a long incubation of diluted enzyme solution at room temperature.

Repair of enzyme activity by SP1: The ability of SP1 to repair enzyme activity was evaluated with respect to the enzymes α-amylase, SOD and HRP.

Repair of α-amylase activity by SP1: As shown in FIG. 17, addition of SP1 to α-amylase, resulted in a 60% increase in α-amylase activity compared to the enzyme without SP1. This result clearly indicates that SP1 repairs α-amylase that lost partial activity during storage or activity assay.

Repair of horseradish peroxidase (HRP) activity by SP1: Diluted HRP is readily inactivated upon exposure to room temperature. As shown in FIG. 18, over 35% of HRP activity was lost upon 30 minutes exposure to room temperature. As is further shown in FIG. 18, SP1 not only protects HRP from room temperature induced inactivation, it also repairs damaged HRP, as about 10% of HRP activity was rescued upon SP1 addition, and was maintained for at least 6 hours thereafter. This is in sharp distinction to the SP1 untreated HRP that continued to lose activity throughout the experiment.

Repair of superoxide disinutase (SOD) activity by SP1: The repair activity of SP1 was also evaluated with respect to SOD. As is shown in FIG. 19, addition of SP1 to cosmetic grade SOD (Pentapharm), resulted in a 60% higher activity compared to SP1 untreated SOD. The repair activity is concentration dependent and demonstrates that SP1 can repair SOD that lost partial activity during storage or assay.

Reduced immune response as a result of fusion of a polypeptide with SP1: 16 mice (C57BL/6) were injected peritoneally (100 μl) with either CBD {5 μM (mice 1-4), 0.05 μM (mice 9-12)} or CBD-SP1 fusion protein {5 μM (mice 5-8), 0.05 μM (mice 12-16)}. As shown in the FIG. 20*a*, 35 days post immunization, blood titer of anti-CBD antibody in mice injected with CBD-SP1 fusion was far lower than blood titer of anti-CBD antibody in mice injected with CBD alone. The difference between antibody titer of mice injected with CBD and mice injected with CBD-SP1 fusion is even larger when the mice were immunized with lower amounts of antigen and after shorter time from injection (FIG. 20*b*(i)-(iv)).

SP1 confers salt tolerance in plants: Insertion of abiotic stress tolerance genes to plants is used to develop stress-tolerant crops. The effect of $SP_1$ protein expression levels on salt tolerance was tested in SP1-transgenic aspen (*P. tremula*) lines. NT (non-transformed plant) plants as well as M4 and L3 transgenic plants express normal level of SP1-protein, whereas H3 transgenic plants express a considerable higher level of SP1 protein. Stem length, leaf retention and final dry weight of plant organs were measured in *P. tremula* plants (NT) and in the three SP1-transformed *P. tremula* lines, following salt stress and recovery from salt stress, in pot experiment, relative to normal irrigation regime (FIGS. 21*a-c*). A severe growth suppression was observed as a result of salt stress. However, H3 plants, which express a considerably higher level of SP1 protein, show much better tolerance to salt stress than plants which express normal or low SP1 levels. The beneficial effect of high SP1 levels during the recovery period was even more clear: H3 plants recovered from salt stress much better than the other lines. It is important to note that no significant difference between the different lines was observed under normal irrigation regiments.

SP1 induces wound healing: As shown in FIG. 22, SP1 stimulated the migration of denuded area scratched in a confluent monolayer, indicating a positive effect of SP1 in wound healing processes.

Effect of SP1 on hair strength: Hair is composed of proteins such as mostly keratin and hence SP1 may stabilize and strengthen the hair. Hair strength was tested by measurement of its ability to carry weight, and was defined as the weight above which it was torn. Because hair strength varies, even among the same donor, each hair was cut into two fragments, one fragment was treated with Tris buffer and the other with the same buffer containing SP1. The strength of each individual fragment was compared with the strength of the other. As shown in FIG. 25, the average strength of the SP1 treated hair was 16%, significantly, higher than that of control untreated hair. Thus SP1 treatment strengthens human hair.

SP1 serving as a molecular scaffold: The fusion between SP1 and cellulose binding domain (CBD) was used to demonstrate that fusion of SP1 with a polypeptide maintains the characteristics of both components. It was demonstrated that recombinant CBD-SP1 fusion maintains the ability to assemble spontaneously into a 12-mer oligomer as SP1 does, it maintain the cellulose binding ability as CBD does, and can stabilizes HRP as SP1 does. FIG. 7 shows a size exclusion HPLC profile of both SP1 and CBD-SP1. Both spontaneously assemble into a 12-mer oligomer (FIG. 10). FIGS. 23a compares the binding ability of CBD-SP1 to cellulose with that of CBD. Equimolar amount of CBD and CBD-SP1 proteins (first two lanes from left; 15 pmol, calculated based on CBD molecular weight) were applied to 30 mg of cellulose (Sigmacell type 20). The same binding and elution procedures were carried out for these two proteins. Similar to CBD, CBD-SP1 bound to the cellulose, and was eluted under the same conditions. The HRP protection activity of both CBD-SP1 and SP1 is shown in FIG. 23b. It is evident that CBD-SP1 stabilizes HRP as SP1 does (note that the molecular weight of CBD-SP1 is about two-fold higher than that of SP1). Thus, these results demonstrate that the fusion of SP1 with CBD maintains the characteristics of both SP1 and CBD.

SP Production: SP extraction and purification from plant parts and sp1-transformed bacteria takes advantage of the protein resistance to boiling and proteases. As shown, for example, in FIGS. 24a(i)-(ii) and 24b, most proteins present in crude extract of both fresh aspen leaves and sp1-transformed bacteria are removed by either boiling or proteolysis by Subtilisin, but SP. The predominant protein found after such treatment is SP.

Table I below, summarizes sources from which SP was purified using the above method. Following Table I, there is a description of the exact procedures used in each case and the details of the activity assay employed.

TABLE I

Protease treatment and boiling of various extracts increases their chaperon specific activity

| Organism | Plant part and/or form | Treatment | Activity U/mg protein Untreated | Treated |
|---|---|---|---|---|
| Arabidopsis | Fresh aerial part | Alcalase + Boiling | ND | 1440 |
| Aspen | Fresh leaves | Alcalase + Boiling | ND | 4000 |
| Aspen | Dry leaves | Alcalase + Boiling | ND | 4000 |
| Avena | Grain powder | Alcalase + Boiling | 645 | 900 |
| Avena | Grain powder | Acid protease + Boiling | 645 | 4700 |
| Barley | Grain powder | Alcalase + Boiling | 413 | 2130 |
| Barley | Grain powder | Acid protease + Boiling | 413 | 2760 |
| Chick pea | Fresh leaves | Alcalase + Boiling | ND | 770 |
| Corn | Dry leaves leaves | Alcalase + Boiling | 700 | 2000 |
| Corn | Dry leaves powder | Alcalase + Boiling + PVPP | 700 | 5000 |
| Corn | Dry leaves powder | Acid protease + Boiling | 700 | 9200 |
| Corn | Gluten | Proteinase K + Boiling | 3700 | 6400 |
| Rice | Grain powder | Alcalase + Boiling | ND | 360 |
| Sorghum | Dry leaves powder | Alcalase + Boiling | 490 | 673 |
| Sorghum | Dry leaves powder | Alcalase + Boiling + PVPP | 490 | 14000 |
| Tomato (M32) | Fresh leaves | Alcalase + Boiling | ND | 180 |
| Tomato (M32) | Fresh leaves | Alcalase + Boiling | ND | 765 |
| Yeast | Semi-dry Powder | Alcalase + Boiling | 230 | 1386 |
| Yeast | Semi-dry Powder | Alcalase + Boiling + PVPP | 230 | 1788 |

ND = Not determined.

SP purification from fresh plant material: Fresh material (200 grams, 80% water) was mixed with 350 ml Na acetate (100 or 150 mM), crashed with home food processor (Magimix) for 5 minutes to a homogenized paste. Solids were separated by gauze, and liquids were collected and boiled for 10 minutes. Solids that were formed by the heat treatment were removed by filtration through a 0.2 mm stainless still mesh and the pH was set to 8.4+/−0.1 with NaOH. Alcalase (Novo Nordisk LTD) was added (1:1000 v/v) and incubated for 2 hours at 37° C. on shaker or stirrer to digest protease sensitive proteins. Protease treatment was followed by boiling for 10 minutes. The precipitated particles were removed by centrifugation (10,000-13,000 g). A filtrate was concentrated by ultra filtration on a 30 kDa cut-off membrane (Sartorius LTD) and wash by phosphate buffered saline. In cases in which phenolic compounds oxidation rendered the obtained filtrate dark (typical for the procedures in which the starting material is from aspen, tomato, corn and sorgum), another cleaning step was performed prior to centrifugation and ultrafiltration which included the addition of 100 ppm ascorbic acid, 400 ppm Na meta-bisulfite (J. T. Baker LTD.) and 2.5% polyvinylpoly-pyrrolidone followed by stirring the mixture over night at 4° C.

SP purification from grains and dry leaves: Grains of different cereals (barley or avena) and pre-dried leafs (aspen, maize or sorgum) and additional products such as baker yeast were grind to powder using a coffee grinder (Braun LTD). Yeast cells were extracted by vortex with glass beads. Four to five grams of powder were used as starting material for protein extraction with 9 to 11 v/w of Na acetate (0.15 M) according to the moisture absorption exhibited by the treated material. The solution was stirred (1.0 hour at room temperature), the liquids were separated by centrifugation (2,700 g, 20 minutes) and the extraction of the solids was repeated, with 9 volumes of buffer per original powder weight, under the same conditions. The collected liquids from both extracts were then treated together according to the basic protocol described above for "SP purification from fresh plant material".

The following assay was used to determine SP activity:

HRP protection assay: A 100 µl aliquot of HRP (Sigma, 5 nM in 40 mM HEPES buffer, pH 7.5) was incubated at 25° C. in the presence of extracts at different protein concentrations. Aliquots were removed after 16 hours to determine remaining enzymatic activity. HRP reaction conditions were determined as follows: 5 µl of 5 nM HRP and 100 pl of TMB substrate (3 3'5 5'-tetramethylbenzidiine; PIERCE) were incubated at 25° C. The reaction was stopped after 10 minutes by the addition of 1 M sulfuric acid and was recorded by a microplate reader at 435 nm. Colorimetric reaction of HRP as well as HRP substrate concentration were determined to be in the linear range. The protection units were defined as the dilution factor of an extract solution at a concentration of 1 mg/ml that confers 50% protection of HRP activity under the above conditions.

Increasing the Specific Activity of SP1:

Tests were undertaken to demonstrate the gain of recombinant SP1 specific activity following autoclave treatment. Pure recombinant SP1 was dialyzed against PBS and was diluted 10 or 100 fold in PBS. Undiluted as well as diluted SP1 were autoclaved and precipitates were removed by centrifugation. The remaining protein concentration and protection activity using the HRP protection assay described above was measured. It was demonstrated that autoclaved SPi better protects HRP activity as compared to non autoclaved SP1, indicating that following autoclave, SP1 specific activity is increased.

Protein gel electrophoresis results (Coomassie blue) demonstrated the gain of recombinant SP1 specific activity following protease treatment. *E. coli* strain BL21(DE3) harboring the plasmid carrying SP1 gene (pET29a, kanamycin resistance) was grown in 5×LB medium and induced by IPTG to express the SP1 protein. Bacteria cell pellet was suspended in TrisHCl buffer (30 mM; pH 8.4; 1 gram/6 ml) and sonified on ice. TRITON-X-100 and Lysozyme were added (0.1% and 10 mg/ml, respectively), incubated with gentle stirring (1 hour at 37° C.), followed by centrifugation (15,000 g, 15 minutes, 4° C.), and the pellet was discarded. To digest protein, alcalase or savinase (Novo Nordisk LTD) were added to the extract at the indicated dilution, and the solution was incubated with gentle stirring (3 hours at 37° C.). To remove boiling sensitive proteins, the extract was boiled (10 minutes), cooled on ice and centrifuged (10,000 g, 15 minutes, 4° C.). An increase in the specific activity was achieved, as determined using the HRP protection assay described above, especially when using the protease Alcalase.

Without being bound to any theory in particular, it is believed that the increase in specific activity observed in the above autoclaving and protease treatment experiments is achieved by elimination, via aggregation or proteolitic digestion of non-SP proteins still present in the isolates and/or elimination, via aggregation or proteolitic digestion, of non-active, denatured or partially denatured, SP proteins present in the isolates, and/or SP activation, via elimination of SP inhibitors, or shifting SP conformation from inactive to active form. An alternative hypotesis is direct effect on the target protein: e.g., elimination of proteases that otherwise degrade it. In all cases, the specific activity of the isolated SP protein, as determined in Units of protecting activity per amount of protein is expected to increase.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Bartels, D. and Thompson, R. D. (1983) The characterization of cDNA clones coding for wheat storage proteins. *Nucl. Acids Res.,* 11, 2961-2978.
2. Buchner, J., Grallert, H., and Jakob, U. (1998) Analysis of chaperone function using citrate synthase as nonnative substrate protein. pp. 323-338. In: Methods in Enzymology, Vol, 290 (Molecular Chaperones) George H. Lorimer and Thomas O. Baldwin (Edt) Academic Press, New York, USA
3. Chen, Q., Osteryoung, K., and Vierling, E. (1994) A 21-kDa chloroplast heat shock protein assembles into high molecular weight complexes in vitro and in organelle. J. Biol. Chem. 269, 13216-13233.
4. Collada, C., Gomez, L., Casado, R., and Aragoncillo, C. (1997) Purification and in vitro chaperone activity of a class I small heat-shock protein abundant in recalcitrant chestnut seeds. Plant Physiol. 115, 71-77.
5. Ehrnsperger, M., Gr?ber, S., Gaestel, M., and Buchner, J. (1997) Binding of non-native protein to Hsp25 during heat shock creates a reservoir of folding intermediates for reactivation EMBO J. 16, 221-229.
6. Goldman, A., Engelman, D. M., Steiz, T. A. (1986) Identifying nonpolar transbilayer helices in amino acid sequences of membrane proteins. Annu. Rev. Biophys. Chem. 15, 321-353.
7. H?rndahl, U., Hall, R. B., Osteryoung, K. W., Vierling, E., Bomman, J. F., and Sundby C. (1999) The chloroplast small heat shock protein undergoes oxidation-depent conformational changes and may protect plants from oxidative stress. Cell Stress & Chaperones 4, 129-138.

8. Hartl, F. U. (1996) Molecular chaperones in cellular protein folding. Nature 381: 571-579
9. Haslbeck, H., Walke, S., Stromer, T., Ehrnsperger, M., White, H. E., Chen, S., Saibil, H. R., and Buchner, J. (1999) Hsp26: a temperature-regulated chaperone. EMBO J. 18, 6744-6751.
10. Ijssel, P. R. L. A. van den, Overkamp, K., Knauf, U., Gaestel, M., and Jong, W. W. de. (1994) αA-crystallin confers cellular thermoresistance. FEBS Letters 355, 54-56.
11. Josephy, P. D., Eling, T. and Mason, R. P. (1982) The horseradish peroxidase-catalyzed oxidation of 3,5,3',5'-tetramethylbenzidine. J.B.C. 257, 3669-3675.
12. Knauf, U., Bielka, H., and Gaestel, M. (1992) Overexpression of the small heat-shock protein, hsp25, inhibits growth of Ehrlich ascites tumor cells. FEBS Letters 309, 297-302.
13. Kyte, J., Doolittle, R. E. (1984) Hydrophobic analysis of polypeptides. J. Mol. Biol 157, 105-132.
14. Laemmli, U. K. (1970) Cleavage of structureal proteins during the assembly of the head of bacteriophage T4. Nature 227, 680-685.
15. Lee, G. J., Pokala, N., and Vierling E. (1995) Structure and in vitro molecular chaperone activity of cytosolic small heat shock protein from pea. J. Biol. Chem. 270, 10432-10438.
16. Mtwisha, L., Brandt, W., McCready, S. and Lindsey, G. G. (1998) HSP 12 is a LEA-like protein in Saccharomyces cerevisiae. Plant Mol. Biol. 37, 513-521.
17. Muchowski, P. J., and Clark, J. I. (1998) ATP-enhanced molecular chaperone functions of the small heat shock protein humam aB crystallin. Biochemistry 95, 1004-1009.
18. Pelah, D., Shoseyov, O., Altman, A. (1995) Characterization of BspA, a major boiling-stable, water-stress-responsive protein in aspen (populus tremula) Tree Physiol. 15, 673-678.
19. Pelah, D., Wang, W. X., Altman, A., Shoseyov, O., Bartels, D. (1997) Differential accumulation of water-stress related proteins, sucrose synthase and soluble sugars in Populus genotypes which differ in their water-stress response. Physiol. Plant. 99, 153-159.
20. Praekel, U. M. and Meacock, P. A. (1990) HSP12, a new small heat shock gene of Saccharomyces cerevisiae: Analysis of structure, regulation and function. Mol. Gen. Genet. 223, 97-106.
21. Rogalla, T., Ehrnsperger, M., Preville, X., Kotlyarov, A., Lutsch, G., Ducasse, C., Paul, C., Wieske, M., Arrigo., A-P., and Buchner, J. (1999) Regulation of Hsp27 oligomerization, chaperone function, and protective activity against oxdative stress/tumor necrosis factor a by phosphrylation. J. Biol.Chem. 274: 27, 18947-18956.
22. Shpigel, E., Goldlust, A., Efroni, G., Avraham, A., Eshel, A., Dekel, M. and Shoseyov, O. (1999) Immobilization of recombinant Heparinase I fused to cellulose-binding domain. Biotech. Bioeng., 65, 17-23.
23. Soto, A., Allona, I., Collada, C., Guevara, M-A., Casado, R., Rodriguez-Cerezo, E., Aragoncillo, C., and Gomez, L. (1999) Heterologous expression of a plant small heat-shock protein enhances Eschrichia coli viability under heat and cold stress. Plant Physiol. 120, 521-528.
24. Suzuki, T. C., Krawitz, D. C. and Vierling, E. (1998) The chloroplast small heat-shock protein oligomer is not phosphorylated and does not dissociate during heat stress in vivo. Plant Physiol. 116, 1151-1161.
25. Veinger, L., Diamant, S., Buchner, J., and Goloubinoff, P. (1998) The small heat-shock protein IbpB from Escherichia coli stabilizes stress-denatured proteins for subsequent refolding by a multichaperone network. J. Biol. Chem. 273, 11032-11037.
26. Waters, E. R., Lee, G. J., and Vierling, E. (1996) Evolution, structure and function of the small heat shock proteins in plants. J. Exper. Bot. 47:(296)325-338
27. Yeh, C-H., Chang, P-F. L., Yeh, K-W., Lin, W-M., Chen, Y-M., and Lin C-Y. (1997) Expression of a gene encoding a 16.9-kDa heat-shock protein, Oshsp 16.9, in Escherichia coli enhances thermotolerance. PNAS 94, 10967-10972.

What is claimed is:

1. An isolated nucleic acid comprising:

(a) a first polynucleotide encoding a boiling and detergent stable protein at least 65% homologous to SEQ ID NO:2, said boiling and detergent stable protein having a chaperone-like activity, said protein being capable of forming stable dimers and having at least one conserved amino acid sequences as set forth in SEQ ID NOs: 36, 37 or 38 as determined using a Best Fit algorithm of GCG, Wisconsin Package Version 9.1 using a plurality of 10.00, a threshold of 4, average weight of 1.00, average match of 2.91 and average mismatch of minus 2.00; and (b) a second polynucleotide including a promoter sequence being operably linked to said first polynucleotide for directing an expression of said boiling and detergent stable protein.

2. The isolated nucleic acid of claim 1, wherein said promoter sequence is a eukaryote promoter.

3. The isolated nucleic acid of claim 2, wherein said eukaryote promoter is a constitutive promoter.

4. The isolated nucleic acid of claim 1, wherein said promoter is a plant promoter selected from the group consisting of a constitutive plant promoter, a tissue specific plant promoter and an inducible plant promoter.

5. The isolated nucleic acid of claim 4, wherein:
(i) said constitutive plant promoter is selected from the group consisting of CaMV35S plant promoter, CaMV19S plant promoter, FMV34S plant promoter, sugarcane bacilliform badnavirus plant promoter, CsVMV plant promoter, *Arabidopsis* ACT2/ACT8 actin plant promoter, *Arabidopsis* ubiquitin UBQ1 plant promoter, barley leaf thionin BTH6 plant promoter, and rice actin plant promoter;
(ii) said tissue specific plant promoter is selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from *Arabidopsis*, napA plant promoter from *Brassica napus* and potato patatin gene plant promoter; and
(iii) said inducible plant promoter is selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

6. The isolated nucleic acid of claim 1, wherein said promoter sequence is a prokaryote promoter.

7. The isolated nucleic acid of claim 1, wherein said stable protein is natively an oligomer.

8. The isolated nucleic acid of claim 1, wherein said chaperone-like activity includes heat stabilization of proteins.

9. A nucleic acid construct comprising the nucleic acid of claim 1.

10. A cell transformed with the nucleic acid of claim 1.

11. An organism transformed with the nucleic acid of claim 1, wherein said organism is selected from the group consisting of micro-organism and a plant.

12. The isolated nucleic acid of claim 1, further comprising
(c) a third polynucleotide encoding an additional protein, said third polynucleotide being adjacent and in frame to said first polynucleotide, said first and third polynucleotides encoding, in combination, a fusion protein of said stable protein and said additional protein.

13. A transgenic plant expressing a denaturant stable protein at least 65% homologous to SEQ ID NO:2, said protein being capable of forming stable dimers and having at least one conserved amino acid sequences as set forth in SEQ ID NOs: 36, 37 or 38 as determined using a Best Fit algorithm of GCG, Wisconsin Package Version 9.1 using a plurality of 10.00, a threshold of 4, average weight of 1.00, average match of 2.91 and average mismatch of minus 2.00; said denaturant stable protein having a chaperone-like activity above a natural amount of said denaturant stable protein having said chaperone-like activity in said plant.

14. The isolated nucleic acid of claim 1, wherein said boiling and detergent stable protein is protease resistant.

15. The isolated nucleic acid of claim 1, wherein said boiling and detergent stable protein is at least 70% homologous to SEQ ID NO:2.

16. The isolated nucleic acid of claim 1, wherein said boiling and detergent stable protein is at least 75% homologous to SEQ ID NO:2.

17. The isolated nucleic acid of claim 1, wherein said boiling and detergent stable protein is at least 80% homologous to SEQ ID NO:2.

18. The isolated nucleic acid of claim 1, wherein said boiling and detergent stable protein is at least 85% homologous to SEQ ID NO:2.

19. The isolated nucleic acid of claim 1, wherein said boiling and detergent stable protein is at least 90% homologous to SEQ ID NO:2.

20. The isolated nucleic acid of claim 1, wherein said boiling and detergent stable protein is at least 95% homologous to SEQ ID NO:2.

21. The isolated nucleic acid of claim 1, wherein said boiling and detergent stable protein is as set forth in SEQ ID NO:2.

22. The transgenic plant of claim 13, wherein said denaturant stable protein is protease resistant.

23. The transgenic plant of claim 13, wherein said denaturant stable protein is at least 70% homologous to SEQ ID NO:2.

24. The transgenic plant of claim 13, wherein said denaturant stable protein is at least 75% homologous to SEQ ID NO:2.

25. The transgenic plant of claim 13, wherein said denaturant stable protein is at least 80% homologous to SEQ ID NO:2.

26. The transgenic plant of claim 13, wherein said denaturant stable protein is at least 85% homologous to SEQ ID NQ:2.

27. The transgenic plant of claim 13, wherein said denaturant stable protein is at least 90% homologous to SEQ ID NO:2.

28. The transgenic plant of claim 13, wherein said denaturant stable protein is at least 95% homologous to SEQ ID NO:2.

29. The transgenic plant of claim 13, wherein said denaturant stable protein is as set forth in SEQ ID NQ:2.

30. An isolated nucleic acid comprising:
(a) a first polynucleotide encoding a boiling stable protein at least 90% homologous to SEQ ID NO:2 said boiling stable protein having antigenic cross-reactivity with the polypeptide having an amino acid sequence as set forth SEQ ID NO:2 and being capable of forming stable dimers; and
(b) a second polynucleotide including a promoter sequence being operably linked to said first polynucleotide for directing an expression of said boiling stable protein.

31. The isolated nucleic acid of claim 30, wherein said promoter sequence is a eukaryote promoter.

32. The isolated nucleic acid of claim 31, wherein said eukaryote promoter is a constitutive promoter.

33. The isolated nucleic acid of claim 30, wherein said promoter is a plant promoter selected from the group consisting of a constitutive plant promoter, a tissue specific plant promoter and an inducible plant promoter.

34. The isolated nucleic acid of claim 30, wherein:
(i) said constitutive plant promoter is selected from the group consisting of CaMV35SS plant promoter, CaMV19S plant promoter, FMV34S plant promoter, sugarcane bacilliform badnavirus plant promoter, CsVMV plant promoter, *Arabidopsis* ACT2/ACT8 actin plant promoter, *Arabidopsis* ubiquitin UBQ1 plant promoter, barley leaf thionin BTH6 plant promoter, and rice actin plant promoter;

(ii) said tissue specific plant promoter is selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from *Arabidopsis*, napA plant promoter from *Brassica napus* and potato patatin gene plant promoter; and (iii) said inducible plant promoter is selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

35. The isolated nucleic acid of claim 30, wherein said promoter sequence is a prokaiyote promoter.

36. The isolated nucleic acid of claim 30, wherein said protein is as set forth in SEQ ID NO:2.

37. The isolated nucleic acid of claim 30, wherein said protein is natively an oligomer.

38. The isolated nucleic acid of claim 30, wherein said protein is a denaturant stable and/or protease resistant protein having a chaperone-like activity.

39. A nucleic acid construct comprising the nucleic acid of claim 30.

40. A cell transformed with the nucleic acid of claim 30.

41. An organism transformed with the nucleic acid of claim 30, wherein said organism is selected from the group consisting of micro-organism and a plant.

42. The isolated nucleic acid of claim 30, further comprising (c) a third polynucleotide encoding an additional protein, said third polynucleotide being adjacent and in frame to said first polynucleotide, said first and third polynucleotides encoding, in combination, a fusion protein of said stable protein and said additional protein.

43. A transgenic plant expressing a recombinant protein at least 95% homologous to SEQ ID NO:2.

44. The transgenic plant of claim 43, wherein said protein is as set forth in SEQ ID NO:2.

45. The isolated nucleic acid of claim 1, wherein said first polynucleotide encodes a boiling and detergent stable protein having an amino acid sequence selected from the group consisting of SEQ ID NOs: 7-32.

* * * * *

SEQUENCE LISTING

<160> NUMBER OF SEQ ID NOS: 40

<210> SEQ ID NO 1
<211> LENGTH: 567
<212> TYPE: DNA
<213> ORGANISM: Populus tremula x Populus tremuloides

<400> SEQUENCE: 1

```
atccacagag agaaagggaa gacatggcaa ccagaactcc aaagcttgtg aagcacacat      60
tgttgactcg gttcaaggat gagatcacac gagaacagat cgacaactac attaatgact     120
ataccaatct gctcgatctc attccaagca tgaagagttt caattggggc acggatctgg     180
gcatggagtc tgcggagcta aaccgaggat acactcatgc ctttgaatct acatttgaga     240
gcaagtctgg tttgcaagag tacctcgatt ctgctgctct tgctgcattt gcagaagggt     300
ttttgcctac tttgtcacag cgtcttgtga tagactactt tctctactaa acgctcagga     360
gtaacgactt cggccgggct atttcatggt aataaagtaa tgtaatgttc aataaatgct     420
ggttttgaac cactgaatgt tcgtgtcttg atttcttgtc tgtgctaagt gaagggagtg     480
ctgctattcc tttaaaaata aagcccttgg ggttgagttg tagttttttca atctttttcc     540
```

```
ccgatttatt tcggtcttgg tgttgtt                                       567

<210> SEQ ID NO 2
<211> LENGTH: 108
<212> TYPE: PRT
<213> ORGANISM: Populus tremula x Populus tremuloides

<400> SEQUENCE: 2

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 3
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 3
aaaaccatgg caaccagaac tccaaagc                                      28

<210> SEQ ID NO 4
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 4
aaaaggatcc ttactttatt accatgaaat agcc                               34

<210> SEQ ID NO 5
<211> LENGTH: 593
<212> TYPE: DNA
<213> ORGANISM: Populus tremula x Populus tremuloides
<220> FEATURE:
<221> NAME/KEY: misc_feature
<222> LOCATION: (224)..()
<223> OTHER INFORMATION: any nucleotide
<220> FEATURE:
<221> NAME/KEY: misc_feature
<222> LOCATION: (451)..()
<223> OTHER INFORMATION: any nucleotide
<220> FEATURE:
<221> NAME/KEY: misc_feature
<222> LOCATION: (566)..()
<223> OTHER INFORMATION: any nucleotide

<400> SEQUENCE: 5
gtcgaaccca cgcgtccgtc tatagcatcc agcagagaga agagaagac atggcaacca    60 gaactccaaa gcttgtgaag cacacattgt tgactcggtt caaggatgag atcacacgag   120
```

-continued

```
aacagatcga caactacatt aatgactata ccaatctgct cgatctcatt ccaagcatga      180
agagtttcaa ttggggcacg gatctgggca tggagtctgc ggantaaacc gaggatacac      240
tcatgccttt gaatctacat ttgagagcaa gtctggtttg caagagtacc tcgattctgc      300
tgctcttgct gcatttgcag aagggttttt gcctactttg tcacagcgtc ttgtgataga      360
ctactttctc tactaaacgc tcaggggtaa cgacttcggc cgggctattt cattggataa      420
agtaatgtat gttcataaat gctggttttg naccactgaa tgttcgtgtc ttgatttctt      480
gttgtgtaag tgaagggagt gtgctattcc ttaaaattaa gccttgggtt gagttgtgtt      540
ttccatcttt tcccggttat tcgggncagg tgtgtttcct cccatttagg cca             593
```

<210> SEQ ID NO 6
<211> LENGTH: 357
<212> TYPE: DNA
<213> ORGANISM: Populus tremula x Populus tremuloides
<220> FEATURE:
<221> NAME/KEY: misc_feature
<222> LOCATION: (201)..()
<223> OTHER INFORMATION: any nucleotide
<220> FEATURE:
<221> NAME/KEY: misc_feature
<222> LOCATION: (302)..()
<223> OTHER INFORMATION: any nucleotide

<400> SEQUENCE: 6

```
tacatccaca gagagaaaga gaagacatgg caaccagaac tccaaagctt gtgaagcaca      60
cattgttgac tcggttcaag gatgagatca cacgagaaca gatcgacaac tacattaatg     120
actataccaa tctgctcgat ctcattccaa gcatgaagag tttcaattgg ggcacggatc     180
tgggcatgga gtctgcggag ntaaaccgag gatacactca tgcctttgaa tctacatttg     240
agagcaagtc tggttgcaag agtacctcga ttctgctgct cttgctgcat ttgcagaagg     300
gnttttgcta ctttgcacag cgcttgtgat agactacttc tctactaaac gctcagg       357
```

<210> SEQ ID NO 7
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: any amino acid

<400> SEQUENCE: 7

```
Val Val Lys His Leu Val Ile Val Gln Phe Lys Glu Asp Val Thr Pro
 1               5                  10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe
```

<210> SEQ ID NO 8

```
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: any amino acid

<400> SEQUENCE: 8

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 9
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: any amino acid

<400> SEQUENCE: 9

Val Val Lys His Leu Val Ile Val Gln Phe Lys Glu Asp Val Thr Pro
1               5                   10                  15

Glu Arg Leu Glu Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 10
<211> LENGTH: 84
<212> TYPE: PRT
<213> ORGANISM: Zea mays
<220> FEATURE:
<221> NAME/KEY: misc_feature
<222> LOCATION: (50)..(51)
<223> OTHER INFORMATION: any amino acid

<400> SEQUENCE: 10

Val Val Lys His Ile Leu Leu Ala Ser Phe Lys Glu Glu Val Thr Gln
1               5                   10                  15

Glu Arg Leu Asp Glu Leu Ile Arg Gly Tyr Ala Ala Leu Val Gly Val
            20                  25                  30
```

```
Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Ile Lys Glu Tyr Ile Glu His Pro Ala His Val
65                  70                  75                  80

Glu Phe Ala Lys
```

<210> SEQ ID NO 11
<211> LENGTH: 98
<212> TYPE: PRT
<213> ORGANISM: Oryza sativa
<220> FEATURE:
<221> NAME/KEY: misc_feature
<222> LOCATION: (50)..(51)
<223> OTHER INFORMATION: any amino acid

<400> SEQUENCE: 11

```
Val Val Lys His Ile Leu Leu Ala Arg Phe Lys Glu Asp Val Ala Pro
1               5                   10                  15

Glu Arg Leu Asp Gln Leu Ile Arg Gly Tyr Ala Gly Leu Val Asp Leu
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Ile Glu His Pro Ala His Val
65                  70                  75                  80

Glu Phe Ala Asn Glu Phe Leu Pro Val Leu Glu Lys Thr Leu Ile Ile
            85                  90                  95

Asp Tyr
```

<210> SEQ ID NO 12
<211> LENGTH: 98
<212> TYPE: PRT
<213> ORGANISM: Triticum aestivum
<220> FEATURE:
<221> NAME/KEY: misc_feature
<222> LOCATION: (21)..()
<223> OTHER INFORMATION: any amino acid
<220> FEATURE:
<221> NAME/KEY: misc_feature
<222> LOCATION: (48)..(49)
<223> OTHER INFORMATION: any amino acid

<400> SEQUENCE: 12

```
Val Val Lys His Leu Val Leu Ala Arg Phe Lys Glu Glu Ala Thr Pro
1               5                   10                  15

Glu Ala Leu Asp Xaa Leu Ile Arg Arg Tyr Ala Gly Leu Val Asp Ala
            20                  25                  30

Val Pro Ser Met Lys Ala Phe His Trp Gly Thr Asp Val Thr Val Xaa
        35                  40                  45

Xaa Leu Asp Thr His Glu Gly Phe Thr His Val Phe Glu Ser Thr Phe
    50                  55                  60

Glu Ser Ala Glu Gly Val Lys Glu Tyr Ile Ala His Pro Ser His Val
65                  70                  75                  80

Glu Phe Val Asp Glu Phe Leu Ala Leu Ala Glu Lys Met Leu Ile Val
            85                  90                  95

Asp Tyr
```

<210> SEQ ID NO 13
<211> LENGTH: 109
<212> TYPE: PRT
<213> ORGANISM: Arabidopsis thaliana

<400> SEQUENCE: 13

Met Glu Glu Ala Lys Gly Pro Val Lys His Val Leu Leu Ala Ser Phe
1               5                   10                  15

Lys Asp Gly Val Ser Pro Glu Lys Ile Glu Leu Ile Lys Gly Tyr
            20                  25                  30

Ala Asn Leu Val Asn Leu Ile Glu Pro Met Lys Ala Phe His Trp Gly
        35                  40                  45

Lys Asp Val Ser Ile Glu Asn Leu His Gln Gly Tyr Thr His Ile Phe
    50                  55                  60

Glu Ser Thr Phe Glu Ser Lys Glu Ala Val Ala Glu Tyr Ile Ala His
65                  70                  75                  80

Pro Ala His Val Glu Phe Ala Thr Ile Phe Leu Gly Ser Leu Asp Lys
                85                  90                  95

Val Leu Val Ile Asp Tyr Lys Pro Thr Ser Val Ser Leu
            100                 105

<210> SEQ ID NO 14
<211> LENGTH: 47
<212> TYPE: PRT
<213> ORGANISM: Arabidopsis thaliana

<400> SEQUENCE: 14

Leu His Gln Gly Tyr Thr His Ile Leu Glu Ser Thr Phe Glu Ser Lys
1               5                   10                  15

Glu Ala Val Ala Glu Tyr Ile Ala His Pro Ala His Val Glu Phe Ala
            20                  25                  30

Thr Ile Phe Leu Gly Ser Leu Asp Lys Val Leu Val Ile Asp Tyr
        35                  40                  45

<210> SEQ ID NO 15
<211> LENGTH: 98
<212> TYPE: PRT
<213> ORGANISM: Glycine max
<220> FEATURE:
<221> NAME/KEY: misc_feature
<222> LOCATION: (50)..(51)
<223> OTHER INFORMATION: any amino acid

<400> SEQUENCE: 15

Val Val Lys His Val Leu Leu Ala Lys Phe Lys Asp Asp Val Thr Pro
1               5                   10                  15

Glu Arg Ile Glu Glu Leu Ile Lys Asp Tyr Ala Asn Leu Val Asn Leu
            20                  25                  30

Ile Pro Pro Met Lys Ser Phe His Trp Gly Lys Asp Val Ser Ala Glu
        35                  40                  45

Asn Xaa Xaa Leu His Gln Gly Phe Thr His Val Phe Glu Ser Thr Phe
    50                  55                  60

Glu Ser Pro Glu Gly Val Ala Glu Tyr Val Ala His Pro Ala His Val
65                  70                  75                  80

Glu Tyr Ala Asn Leu Phe Leu Ser Cys Leu Glu Lys Val Ile Val Ile
                85                  90                  95

Asp Tyr

```
<210> SEQ ID NO 16
<211> LENGTH: 98
<212> TYPE: PRT
<213> ORGANISM: Lycopersicon esculentum
<220> FEATURE:
<221> NAME/KEY: misc_feature
<222> LOCATION: (50)..(51)
<223> OTHER INFORMATION: any amino acid

<400> SEQUENCE: 16

Val Val Lys His Ile Leu Leu Ala Lys Phe Lys Asp Gly Ile Pro Pro
1               5                   10                  15

Glu Gln Ile Asp Gln Leu Ile Lys Gln Tyr Ala Asn Leu Val Asn Leu
            20                  25                  30

Val Glu Pro Met Lys Ala Phe Gln Trp Gly Lys Asp Val Ser Ile Glu
        35                  40                  45

Asn Xaa Xaa Leu His Gln Gly Phe Thr His Val Phe Glu Ser Thr Phe
50                  55                  60

Asp Ser Leu Glu Gly Val Ala Glu Tyr Ile Ala His Pro Val His Val
65                  70                  75                  80

Glu Tyr Ala Asn Thr Leu Leu Pro Gln Leu Glu Lys Phe Leu Ile Val
                85                  90                  95

Asp Tyr

<210> SEQ ID NO 17
<211> LENGTH: 93
<212> TYPE: PRT
<213> ORGANISM: Glycine max
<220> FEATURE:
<221> NAME/KEY: misc_feature
<222> LOCATION: (49)..(50)
<223> OTHER INFORMATION: any amino acid

<400> SEQUENCE: 17

His Val Leu Leu Pro Lys Leu Lys Asp Tyr Phe Thr Pro Glu Arg Ile
1               5                   10                  15

Glu Leu Met Val Asp Tyr Ala Asn Leu Val Asn Leu Met Pro Arg Met
            20                  25                  30

Lys Ser Phe His Ser Gly Arg Asp Val Ser Ala Glu Tyr Leu His Leu
        35                  40                  45

Xaa Xaa Gly Cys Thr His Val Tyr Glu Ser Thr Phe Asp Ser Pro Gly
50                  55                  60

Val Ala Glu Tyr Val Ala His Ala His Val Glu Tyr Ala Asn Gln
65                  70                  75                  80

Asp Leu Ser Cys Leu Glu Lys Val Ile Ala Ile Asp Tyr
                85                  90

<210> SEQ ID NO 18
<211> LENGTH: 108
<212> TYPE: PRT
<213> ORGANISM: Populus tremula x Populus tremuloides

<400> SEQUENCE: 18

Met Ala Thr Arg Thr Pro Lys Leu Val Lys His Thr Leu Ala Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45
```

```
Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
                100                 105
```

<210> SEQ ID NO 19
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: any amino acid
<220> FEATURE:
<221> NAME/KEY: misc_feature
<222> LOCATION: (49)..()
<223> OTHER INFORMATION: any amino acid

<400> SEQUENCE: 19

```
Lys His Leu Cys Leu Val Arg Phe Lys Glu Gly Val Val Glu Asp
1               5                   10                  15

Ile Xaa Xaa Xaa Ile Glu Glu Leu Thr Lys Leu Ala Ala Glu Leu Asp
                20                  25                  30

Thr Val Lys Phe Phe Gly Trp Gly Lys Asp Val Leu Asn Gln Glu Ala
            35                  40                  45

Xaa Leu Thr Gln Gly Phe Thr His Val Phe Ser Met Ser Phe Ala Ser
    50                  55                  60

Ala Glu Asp Leu Ala Ala Tyr Met Gly His Glu Lys His Ser Ala Phe
65                  70                  75                  80

Ala Ala Thr Phe Met Ala Val Leu Asp Lys Val Val Val Leu Asp Phe
                85                  90                  95
```

<210> SEQ ID NO 20
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: any amino acid
<220> FEATURE:
<221> NAME/KEY: misc_feature
<222> LOCATION: (49)..()
<223> OTHER INFORMATION: any amino acid

<400> SEQUENCE: 20

```
Lys His Leu Cys Leu Val Arg Phe Lys Glu Gly Val Val Glu Asp
1               5                   10                  15

Ile Xaa Xaa Xaa Ile Glu Glu Leu Thr Lys Leu Ala Ala Glu Leu Asp
                20                  25                  30

Thr Val Lys Phe Phe Gly Trp Gly Lys Asp Val Leu Asn Gln Glu Ala
            35                  40                  45

Xaa Leu Thr Gln Gly Phe Thr His Val Phe Ser Met Ser Phe Ala Ser
    50                  55                  60

Ala Glu Asp Leu Ala Ala Cys Met Gly His Glu Lys His Ser Ala Phe
65                  70                  75                  80

Ala Ala Thr Phe Met Ala Val Leu Asp Lys Val Val Val Leu Asp Phe
                85                  90                  95
```

<210> SEQ ID NO 21
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: any amino acid
<220> FEATURE:
<221> NAME/KEY: misc_feature
<222> LOCATION: (49)..()
<223> OTHER INFORMATION: any amino acid

<400> SEQUENCE: 21

Lys His Leu Cys Met Ala Lys Phe Lys Glu Gly Val Val Val Glu Asp
1               5                   10                  15

Ile Xaa Xaa Xaa Ile Gln Glu Leu Thr Lys Leu Ala Ala Glu Leu Asp
                20                  25                  30

Thr Val Lys Tyr Phe Gly Trp Gly Lys Asp Val Leu Asn Gln Glu Ala
            35                  40                  45

Xaa Leu Thr Gln Gly Phe Thr His Val Phe Val Met Thr Phe Ala Ser
50                  55                  60

Ala Glu Asp Leu Ala Ala Cys Met Gly His Glu Lys His Thr Ala Phe
65                  70                  75                  80

Ala Ala Thr Phe Met Ala Ala Leu Asp Lys Val Val Met Asp Phe
                85                  90                  95

<210> SEQ ID NO 22
<211> LENGTH: 97
<212> TYPE: PRT
<213> ORGANISM: Oryza sativa
<220> FEATURE:
<221> NAME/KEY: misc_feature
<222> LOCATION: (15)..(17)
<223> OTHER INFORMATION: any amino acid
<220> FEATURE:
<221> NAME/KEY: misc_feature
<222> LOCATION: (45)..()
<223> OTHER INFORMATION: any amino acid

<400> SEQUENCE: 22

Val Lys His Leu Cys Leu Val Lys Phe Lys Glu Glu Val Leu Xaa Xaa
1               5                   10                  15

Xaa Val Asp Asp Ile Leu Gln Gly Met Thr Lys Leu Val Ser Glu Met
                20                  25                  30

Asp Met Val Lys Ser Phe Glu Trp Gly Lys Asp Val Xaa Leu Asn Gln
            35                  40                  45

Glu Met Leu Thr Gln Gly Phe Thr His Val Ser Leu Thr Phe Ala
50                  55                  60

Ser Ser Glu Asp Leu Thr Thr Tyr Met Ser His Glu Arg His Gln Glu
65                  70                  75                  80

Phe Ala Gly Thr Phe Met Ala Ala Ile Asp Lys Val Val Val Asp
                85                  90                  95

Phe

<210> SEQ ID NO 23
<211> LENGTH: 104
<212> TYPE: PRT
<213> ORGANISM: Sorghum bicolor
<220> FEATURE:
<221> NAME/KEY: misc_feature
<222> LOCATION: (40)..(42)

```
<223> OTHER INFORMATION: any amino acid
<220> FEATURE:
<221> NAME/KEY: misc_feature
<222> LOCATION: (52)..()
<223> OTHER INFORMATION: any amino acid

<400> SEQUENCE: 23

Arg Arg Pro Thr Met Gly Glu Val Lys His Leu Cys Leu Val Lys Phe
1               5                   10                  15

Lys Glu Gly Val Val Glu Asp Val Leu Lys Gly Met Thr Asp Leu
            20                  25                  30

Val Ala Gly Met Asp Met Val Xaa Xaa Xaa Lys Ser Phe Glu Trp Gly
        35                  40                  45

Gln Asp Val Xaa Leu Asn Gln Glu Met Leu Thr Gln Gly Phe Thr His
    50                  55                  60

Val Phe Ser Leu Thr Phe Ala Phe Ala Asp Leu Ala Thr Tyr Met
65                  70                  75                  80

Gly His Asp Arg His Ala Ala Phe Ala Ala Thr Phe Met Ala Ala Leu
                85                  90                  95

Asp Lys Val Val Val Ile Asp Phe
            100

<210> SEQ ID NO 24
<211> LENGTH: 77
<212> TYPE: PRT
<213> ORGANISM: Zea mays
<220> FEATURE:
<221> NAME/KEY: misc_feature
<222> LOCATION: (25)..()
<223> OTHER INFORMATION: any amino acid

<400> SEQUENCE: 24

Glu Ser Thr Phe Glu Ser Thr Glu Gly Ile Lys Glu Tyr Ile Glu His
1               5                   10                  15

Pro Ala His Val Glu Phe Ala Lys Xaa Leu Asn Gln Glu Met Leu Thr
            20                  25                  30

Gln Gly Phe Thr His Val Phe Ser Leu Thr Phe Ala Thr Ala Ala Asp
        35                  40                  45

Leu Ala Ala Tyr Met Ala His Asp Ser His Thr Ala Phe Ala Ala Thr
    50                  55                  60

Phe Met Ala Ala Ile Asp Lys Val Leu Val Val Asp Phe
65                  70                  75

<210> SEQ ID NO 25
<211> LENGTH: 97
<212> TYPE: PRT
<213> ORGANISM: Lycopersicon esculentum
<220> FEATURE:
<221> NAME/KEY: misc_feature
<222> LOCATION: (32)..(34)
<223> OTHER INFORMATION: any amino acid
<220> FEATURE:
<221> NAME/KEY: misc_feature
<222> LOCATION: (44)..(45)
<223> OTHER INFORMATION: any amino acid

<400> SEQUENCE: 25

Lys His Leu Val Leu Val Lys Phe Lys Glu Asp Val Val Glu Asp
1               5                   10                  15

Ile Leu Lys Glu Leu Glu Lys Leu Val Gln Glu Met Asp Ile Val Xaa
            20                  25                  30

Xaa Xaa Lys Ser Phe Val Trp Gly Lys Asp Val Xaa Xaa Glu Ser His
```

```
                35                  40                  45
Glu Met Leu Arg Gln Gly Phe Thr His Ala Ile Ile Met Thr Phe Asn
    50                  55                  60

Ser Lys Glu Asp Tyr Gln Thr Phe Ala Asn His Pro Asn His Val Gly
65                  70                  75                  80

Phe Ser Ala Thr Phe Ala Thr Val Ile Asp Lys Ala Val Leu Leu Asp
                85                  90                  95

Phe

<210> SEQ ID NO 26
<211> LENGTH: 94
<212> TYPE: PRT
<213> ORGANISM: Solanum tuberosum
<220> FEATURE:
<221> NAME/KEY: misc_feature
<222> LOCATION: (29)..(31)
<223> OTHER INFORMATION: any amino acid
<220> FEATURE:
<221> NAME/KEY: misc_feature
<222> LOCATION: (41)..(42)
<223> OTHER INFORMATION: any amino acid
<220> FEATURE:
<221> NAME/KEY: misc_feature
<222> LOCATION: (75)..(76)
<223> OTHER INFORMATION: any amino acid

<400> SEQUENCE: 26

Leu Leu Val Lys Phe Lys Gln Asp Val Val Glu Glu Asp Val Leu Lys
1               5                   10                  15

Gln Ile Glu Gln Leu Val Asn Glu Ile Asp Leu Ile Xaa Xaa Xaa Lys
                20                  25                  30

Ser Phe Val Trp Gly Lys Asp Thr Xaa Xaa Glu Ser Asn Glu Met Val
            35                  40                  45

Thr Gln Gly Tyr Thr His Ala Met Ile Met Thr Phe Asn Ser Lys Glu
        50                  55                  60

Asp Tyr Glu Ala Cys Val Val Lys Glu Val Xaa Xaa Glu Phe Ser Ala
65                  70                  75                  80

Ile Phe Val Thr Val Val Glu Lys Ile Leu Val Leu Asn Phe
                85                  90

<210> SEQ ID NO 27
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: any amino acid
<220> FEATURE:
<221> NAME/KEY: misc_feature
<222> LOCATION: (43)..(44)
<223> OTHER INFORMATION: any amino acid

<400> SEQUENCE: 27

His Tyr Val Ile Val Lys Phe Lys Asp Gly Val Ala Xaa Xaa Xaa Val
1               5                   10                  15

Asp Asp Leu Ile Gln Gly Leu Glu Lys Met Val Phe Gly Ile Asp His
                20                  25                  30

Val Lys Ser Phe Glu Trp Gly Lys Asp Ile Xaa Xaa Glu Ser His Asp
            35                  40                  45

Met Leu Arg Gln Gly Phe Thr His Ala Phe Leu Met Thr Phe Asn Gly
        50                  55                  60
```

-continued

Lys Glu Glu Phe Asn Ala Phe Gln Thr His Pro Asn His Leu Glu Phe
65                  70                  75                  80

Ser Gly Val Phe Ser Pro Ala Ile Glu Lys Ile Val Val Leu Asp Phe
                85                  90                  95

<210> SEQ ID NO 28
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: any amino acid
<220> FEATURE:
<221> NAME/KEY: misc_feature
<222> LOCATION: (43)..(44)
<223> OTHER INFORMATION: any amino acid

<400> SEQUENCE: 28

His Tyr Val Ile Val Lys Phe Lys Asp Gly Val Ala Xaa Xaa Xaa Val
1               5                   10                  15

Asp Glu Leu Ile Gln Gly Leu Glu Lys Met Val Ser Gly Ile Asp His
                20                  25                  30

Val Lys Ser Phe Glu Trp Gly Lys Asp Ile Xaa Xaa Glu Ser His Asp
            35                  40                  45

Met Leu Arg Gln Gly Phe Thr His Val Phe Leu Met Ala Phe Asn Gly
        50                  55                  60

Lys Glu Glu Phe Asn Ala Phe Gln Thr His Pro Asn His Leu Glu Phe
65                  70                  75                  80

Thr Gly Val Phe Ser Pro Ala Ile Glu Lys Ile Val Val Leu Asp Phe
                85                  90                  95

<210> SEQ ID NO 29
<211> LENGTH: 97
<212> TYPE: PRT
<213> ORGANISM: Glycine max
<220> FEATURE:
<221> NAME/KEY: misc_feature
<222> LOCATION: (14)..(16)
<223> OTHER INFORMATION: any amino acid
<220> FEATURE:
<221> NAME/KEY: misc_feature
<222> LOCATION: (44)..(45)
<223> OTHER INFORMATION: any amino acid

<400> SEQUENCE: 29

Lys His Phe Val Ile Val Lys Phe Lys Glu Gly Val Ala Xaa Xaa Xaa
1               5                   10                  15

Val Asp Glu Leu Thr Lys Gly Met Glu Lys Leu Val Thr Glu Ile Gly
                20                  25                  30

Ala Val Lys Ser Phe Glu Trp Gly Gln Asp Ile Xaa Xaa Glu Ser Leu
            35                  40                  45

Asp Val Leu Arg Gln Gly Phe Thr His Ala Phe Leu Met Thr Phe Asn
        50                  55                  60

Lys Lys Glu Asp Phe Val Ala Phe Gln Ser His Pro Asn His Val Glu
65                  70                  75                  80

Phe Ser Thr Lys Phe Ser Ala Ala Ile Glu Asn Ile Val Leu Leu Asp
                85                  90                  95

Phe

<210> SEQ ID NO 30
<211> LENGTH: 43

```
<212> TYPE: PRT
<213> ORGANISM: Glycine max
<220> FEATURE:
<221> NAME/KEY: misc_feature
<222> LOCATION: (18)..(19)
<223> OTHER INFORMATION: any amino acid

<400> SEQUENCE: 30
```

Leu Val Ser Glu Ile His Ala Val Lys Ser Phe Glu Trp Gly Gln Asp
1               5                   10                  15

Ile Xaa Xaa Glu Ser Leu Asp Val Leu Arg Gln Gly Phe Thr His Ala
            20                  25                  30

Phe Leu Met Thr Phe Asn Lys Lys Arg Arg Leu
        35                  40

```
<210> SEQ ID NO 31
<211> LENGTH: 111
<212> TYPE: PRT
<213> ORGANISM: Arabidopsis thaliana

<400> SEQUENCE: 31
```

Met Ala Thr Ser Gly Phe Lys His Leu Val Val Lys Phe Lys Glu
1               5                   10                  15

Asp Thr Lys Val Asp Glu Ile Leu Lys Gly Leu Glu Asn Leu Val Ser
            20                  25                  30

Gln Ile Asp Thr Val Lys Ser Phe Glu Trp Gly Glu Asp Lys Glu Ser
        35                  40                  45

His Asp Met Leu Arg Gln Gly Phe Thr His Ala Phe Ser Met Thr Phe
    50                  55                  60

Glu Asn Lys Asp Gly Tyr Val Ala Phe Thr Ser His Pro Leu His Val
65                  70                  75                  80

Glu Phe Ser Ala Ala Phe Thr Ala Val Ile Asp Lys Ile Val Leu Leu
                85                  90                  95

Asp Phe Pro Val Ala Ala Val Lys Ser Ser Val Val Ala Thr Pro
            100                 105                 110

```
<210> SEQ ID NO 32
<211> LENGTH: 100
<212> TYPE: PRT
<213> ORGANISM: Glycine max
<220> FEATURE:
<221> NAME/KEY: misc_feature
<222> LOCATION: (39)..()
<223> OTHER INFORMATION: any amino acid
<220> FEATURE:
<221> NAME/KEY: misc_feature
<222> LOCATION: (55)..(56)
<223> OTHER INFORMATION: any amino acid

<400> SEQUENCE: 32
```

Lys Thr Val Glu His Ile Val Leu Phe Lys Val Lys Glu Glu Thr Glu
1               5                   10                  15

Pro Ser Lys Val Ser Asp Met Val Asn Gly Leu Gly Ser Leu Val Ser
            20                  25                  30

Leu Asp Pro Val Leu His Xaa Leu Ser Val Gly Pro Leu Leu Arg Asn
        35                  40                  45

Arg Ser Ser Ala Leu Thr Xaa Xaa Phe Thr His Met Leu His Ser Arg
    50                  55                  60

Tyr Lys Ser Lys Glu Asp Leu Glu Ala Tyr Ser Ala His Pro Ser His
65                  70                  75                  80

Val Ser Val Val Lys Gly Tyr Val Leu Pro Ile Ile Asp Asp Ile Met

```
                        85                  90                  95

Ser Val Asp Trp
            100

<210> SEQ ID NO 33
<211> LENGTH: 102
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (12)..()
<223> OTHER INFORMATION: any amino acid
<220> FEATURE:
<221> NAME/KEY: misc_feature
<222> LOCATION: (14)..()
<223> OTHER INFORMATION: any amino acid
<220> FEATURE:
<221> NAME/KEY: misc_feature
<222> LOCATION: (17)..(18)
<223> OTHER INFORMATION: any amino acid
<220> FEATURE:
<221> NAME/KEY: misc_feature
<222> LOCATION: (20)..()
<223> OTHER INFORMATION: any amino acid
<220> FEATURE:
<221> NAME/KEY: misc_feature
<222> LOCATION: (23)..()
<223> OTHER INFORMATION: any amino acid
<220> FEATURE:
<221> NAME/KEY: misc_feature
<222> LOCATION: (27)..()
<223> OTHER INFORMATION: any amino acid
<220> FEATURE:
<221> NAME/KEY: misc_feature
<222> LOCATION: (30)..(32)
<223> OTHER INFORMATION: any amino acid
<220> FEATURE:
<221> NAME/KEY: misc_feature
<222> LOCATION: (34)..()
<223> OTHER INFORMATION: any amino acid
<220> FEATURE:
<221> NAME/KEY: misc_feature
<222> LOCATION: (36)..(37)
<223> OTHER INFORMATION: any amino acid
<220> FEATURE:
<221> NAME/KEY: misc_feature
<222> LOCATION: (42)..()
<223> OTHER INFORMATION: any amino acid
<220> FEATURE:
<221> NAME/KEY: misc_feature
<222> LOCATION: (48)..(49)
<223> OTHER INFORMATION: any amino acid
<220> FEATURE:
<221> NAME/KEY: misc_feature
<222> LOCATION: (51)..(54)
<223> OTHER INFORMATION: any amino acid
<220> FEATURE:
<221> NAME/KEY: misc_feature
<222> LOCATION: (77)..(78)
<223> OTHER INFORMATION: any amino acid
<220> FEATURE:
<221> NAME/KEY: misc_feature
<222> LOCATION: (87)..(88)
<223> OTHER INFORMATION: any amino acid
<220> FEATURE:
<221> NAME/KEY: misc_feature
<222> LOCATION: (90)..()
<223> OTHER INFORMATION: any amino acid
<220> FEATURE:
<221> NAME/KEY: misc_feature
<222> LOCATION: (92)..(93)
<223> OTHER INFORMATION: any amino acid

<400> SEQUENCE: 33
```

Val Lys His Leu Val Leu Val Lys Phe Lys Glu Xaa Val Xaa Pro Glu
1               5                   10                  15

Xaa Xaa Asp Xaa Leu Ile Xaa Gly Tyr Ala Xaa Leu Val Xaa Xaa Xaa
            20                  25                  30

Asp Xaa Val Xaa Xaa Met Lys Ser Phe Xaa Trp Gly Lys Asp Val Xaa
        35                  40                  45

Xaa Glu Xaa Xaa Xaa Xaa Leu His Gln Gly Phe Thr His Val Phe Glu
    50                  55                  60

Ser Thr Phe Glu Ser Lys Glu Gly Val Ala Glu Tyr Xaa Xaa His Pro
65              70                  75                  80

Ala His Val Glu Phe Ala Xaa Xaa Phe Xaa Leu Xaa Xaa Leu Glu Lys
                85                  90                  95

Val Leu Val Ile Asp Phe
            100

<210> SEQ ID NO 34
<211> LENGTH: 428
<212> TYPE: DNA
<213> ORGANISM: Populus deltoides

<400> SEQUENCE: 34
atggcaacca gaactccaaa gcttgtgaag cacacattgt tgactcggtt caaggatgag      60
atcacacgag aacaaatcga caactacatt aatgactata ccaatctgct cgatctcatt     120
ccaaccatga gagtttcaa ttggggcacg gatttgggca tggagtctgc ggagctaaac     180
cgaggataca ctcatgcctt tgaatctaca tttgagagca agtcaggttt gcaagagtac     240
ctcgattctg ctgctcttgc tgcatttgca gaaggatttt tgcctacttt gtcacagcgt     300
cttgtgatag actactttct ctactaaatg ctcaggagta cgacttcgg ccgggctatt      360 tcatgggaat aaagtaatgt aatgtgcaat aaatgctggt tttgaaccac tgaatgttcg     420
tgtcttga                                                              428

<210> SEQ ID NO 35
<211> LENGTH: 112
<212> TYPE: PRT
<213> ORGANISM: Populus deltoides

<400> SEQUENCE: 35

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Thr Met Lys Ser Phe Thr Phe
        35                  40                  45

Asn Trp Gly Thr Asp Leu Gly Met Glu Ser Ala Glu Leu Asn Arg Gly
    50                  55                  60

Tyr Thr His Ala Phe Glu Ser Thr Phe Glu Ser Lys Ser Gly Leu Gln
65              70                  75                  80

Glu Tyr Leu Asp Ser Ala Ala Leu Ala Ala Phe Ala Glu Gly Phe Leu
                85                  90                  95

Pro Thr Leu Ser Gln Arg Leu Val Ile Asp Phe Thr Tyr Phe Leu Tyr
            100                 105                 110

<210> SEQ ID NO 36
<211> LENGTH: 9
<212> TYPE: PRT
<213> ORGANISM: Artificial Sequence -continued
<220> FEATURE:
<223> OTHER INFORMATION: conserved consensus sequences

<400> SEQUENCE: 36

His Ala Phe Glu Ser Thr Phe Glu Ser
1               5

<210> SEQ ID NO 37
<211> LENGTH: 3
<212> TYPE: PRT
<213> ORGANISM: Artificial Sequence
<220> FEATURE:
<223> OTHER INFORMATION: conserved consensus sequences

<400> SEQUENCE: 37

Val Lys His
1

<210> SEQ ID NO 38
<211> LENGTH: 3
<212> TYPE: PRT
<213> ORGANISM: Artificial Sequence
<220> FEATURE:
<223> OTHER INFORMATION: conserved consensus sequences

<400> SEQUENCE: 38

Lys Ser Phe
1

<210> SEQ ID NO 39
<211> LENGTH: 497
<212> TYPE: DNA
<213> ORGANISM: Populus tremula x Populus tremuloides
<220> FEATURE:
<221> NAME/KEY: misc_feature
<222> LOCATION: (21)..()
<223> OTHER INFORMATION: any nucleotide
<220> FEATURE:
<221> NAME/KEY: misc_feature
<222> LOCATION: (50)..()
<223> OTHER INFORMATION: any nucleotide
<220> FEATURE:
<221> NAME/KEY: misc_feature
<222> LOCATION: (75)..()
<223> OTHER INFORMATION: any nucleotide
<220> FEATURE:
<221> NAME/KEY: misc_feature
<222> LOCATION: (108)..()
<223> OTHER INFORMATION: any nucleotide
<220> FEATURE:
<221> NAME/KEY: misc_feature
<222> LOCATION: (128)..()
<223> OTHER INFORMATION: any nucleotide
<220> FEATURE:
<221> NAME/KEY: misc_feature
<222> LOCATION: (147)..()
<223> OTHER INFORMATION: any nucleotide
<220> FEATURE:
<221> NAME/KEY: misc_feature
<222> LOCATION: (182)..()
<223> OTHER INFORMATION: any nucleotide
<220> FEATURE:
<221> NAME/KEY: misc_feature
<222> LOCATION: (270)..()
<223> OTHER INFORMATION: any nucleotide

<400> SEQUENCE: 39
tcagagagag aaagagaaga ntggaacaga actccaaagc ttgtgaagan acattgtgac      60
tcggtcaagg atgantcaca cagaacagat cgacaataca ttaatganat accaatctgc    120
tcgatccntc attccaagct gaaganttca ttggggcacg gatctgggct ggagtctgcg    180

```
gntaaaccga ggatacactc agcctttgat ctactttgag agcagtctgg tttgcaagag      240
tactcgatct gctgctcttg ctgcattgcn gaagggtttg cctactttgt cacagcgtct      300
tgtgatagac tactttctct actaaacgct cagggtaacg acttcggccg ggtattcatg      360
gataagtatg tatgtccata atgctggttt gaccactgat gtccgtgtct gattctgttg      420
tgctagtgag ggatgctgct atccttaaaa taagcctggg ttgagtgtgt ttccactttt      480
cccgataatt cggtcag                                                     497
```

```
<210> SEQ ID NO 40
<211> LENGTH: 366
<212> TYPE: DNA
<213> ORGANISM: Populus tremula x Populus tremuloides
<220> FEATURE:
<221> NAME/KEY: misc_feature
<222> LOCATION: (54)..()
<223> OTHER INFORMATION: any nucleotide
<220> FEATURE:
<221> NAME/KEY: misc_feature
<222> LOCATION: (59)..()
<223> OTHER INFORMATION: any nucleotide
<220> FEATURE:
<221> NAME/KEY: misc_feature
<222> LOCATION: (63)..()
<223> OTHER INFORMATION: any nucleotide
<220> FEATURE:
<221> NAME/KEY: misc_feature
<222> LOCATION: (72)..()
<223> OTHER INFORMATION: any nucleotide
<220> FEATURE:
<221> NAME/KEY: misc_feature
<222> LOCATION: (79)..()
<223> OTHER INFORMATION: any nucleotide
<220> FEATURE:
<221> NAME/KEY: misc_feature
<222> LOCATION: (83)..()
<223> OTHER INFORMATION: any nucleotide
<220> FEATURE:
<221> NAME/KEY: misc_feature
<222> LOCATION: (99)..()
<223> OTHER INFORMATION: any nucleotide
<220> FEATURE:
<221> NAME/KEY: misc_feature
<222> LOCATION: (114)..()
<223> OTHER INFORMATION: any nucleotide
<220> FEATURE:
<221> NAME/KEY: misc_feature
<222> LOCATION: (117)..()
<223> OTHER INFORMATION: any nucleotide
<220> FEATURE:
<221> NAME/KEY: misc_feature
<222> LOCATION: (121)..()
<223> OTHER INFORMATION: any nucleotide
<220> FEATURE:
<221> NAME/KEY: misc_feature
<222> LOCATION: (138)..()
<223> OTHER INFORMATION: any nucleotide
<220> FEATURE:
<221> NAME/KEY: misc_feature
<222> LOCATION: (141)..()
<223> OTHER INFORMATION: any nucleotide
<220> FEATURE:
<221> NAME/KEY: misc_feature
<222> LOCATION: (144)..()
<223> OTHER INFORMATION: any nucleotide
<220> FEATURE:
<221> NAME/KEY: misc_feature
<222> LOCATION: (153)..()
<223> OTHER INFORMATION: any nucleotide
<220> FEATURE:
```

```
<221> NAME/KEY: misc_feature
<222> LOCATION: (178)..()
<223> OTHER INFORMATION: any nucleotide
<220> FEATURE:
<221> NAME/KEY: misc_feature
<222> LOCATION: (200)..()
<223> OTHER INFORMATION: any nucleotide
<220> FEATURE:
<221> NAME/KEY: misc_feature
<222> LOCATION: (212)..()
<223> OTHER INFORMATION: any nucleotide
<220> FEATURE:
<221> NAME/KEY: misc_feature
<222> LOCATION: (221)..()
<223> OTHER INFORMATION: any nucleotide
<220> FEATURE:
<221> NAME/KEY: misc_feature
<222> LOCATION: (231)..()
<223> OTHER INFORMATION: any nucleotide
<220> FEATURE:
<221> NAME/KEY: misc_feature
<222> LOCATION: (245)..()
<223> OTHER INFORMATION: any nucleotide
<220> FEATURE:
<221> NAME/KEY: misc_feature
<222> LOCATION: (252)..()
<223> OTHER INFORMATION: any nucleotide
<220> FEATURE:
<221> NAME/KEY: misc_feature
<222> LOCATION: (266)..()
<223> OTHER INFORMATION: any nucleotide
<220> FEATURE:
<221> NAME/KEY: misc_feature
<222> LOCATION: (274)..()
<223> OTHER INFORMATION: any nucleotide
<220> FEATURE:
<221> NAME/KEY: misc_feature
<222> LOCATION: (281)..()
<223> OTHER INFORMATION: any nucleotide
<220> FEATURE:
<221> NAME/KEY: misc_feature
<222> LOCATION: (306)..()
<223> OTHER INFORMATION: any nucleotide
<220> FEATURE:
<221> NAME/KEY: misc_feature
<222> LOCATION: (323)..()
<223> OTHER INFORMATION: any nucleotide

<400> SEQUENCE: 40
aacccagcaa ctcccaaagc ttgtgcaagc tacgacattg ttgcactcgg ttcnaaggna      60
tgnagcatca cnacgtagna acnagcatcg cacgaactna cattcaatgc actnatnacc    120
naatctgctc gcatctcnat nccnaagcga tgnaagcagt ttccaattgg ggcgaggnat    180
ctgggcatgg agtctgcggn taacaccgag gnatacactc natgcctttg naatctcaca    240
tttgnagcag cnaagtctgg tttgcnaagc agtnacctcg nattctgctg ctcttgctgc    300
atttgnaaca gggttttttgc ctnactttgt ccacagcgtc ttgtgataga ttactttctc   360
tactaa                                                               366
```